(12) United States Patent
Manku et al.

(10) Patent No.: US 10,544,088 B2
(45) Date of Patent: Jan. 28, 2020

(54) PHARMACEUTICALLY ACCEPTABLE SALTS OF FATTY ACIDS

(71) Applicant: DS Biopharma Limited, Dublin (IE)

(72) Inventors: Mehar Manku, Birmingham (GB); David Coughlan, Dublin (IE); Bill Downes, Dublin (IE)

(73) Assignee: DS Biopharma Limited (IE)

( * ) Notice: Subject to any disclaimer, the term of this patent is extended or adjusted under 35 U.S.C. 154(b) by 0 days.

(21) Appl. No.: 15/828,700

(22) Filed: Dec. 1, 2017

(65) Prior Publication Data

US 2018/0118655 A1    May 3, 2018

Related U.S. Application Data

(63) Continuation of application No. 14/543,638, filed on Nov. 17, 2014, now Pat. No. 10,017,453.

(60) Provisional application No. 61/904,600, filed on Nov. 15, 2013.

(51) Int. Cl.
| | | |
|---|---|---|
| *C07C 229/26* | (2006.01) | |
| *C07C 59/42* | (2006.01) | |
| *C07D 295/027* | (2006.01) | |
| *C07C 215/10* | (2006.01) | |
| *A61K 31/202* | (2006.01) | |
| *C07C 241/04* | (2006.01) | |

(52) U.S. Cl.
CPC .......... *C07C 229/26* (2013.01); *A61K 31/202* (2013.01); *C07C 59/42* (2013.01); *C07C 215/10* (2013.01); *C07D 295/027* (2013.01); *C07C 241/04* (2013.01)

(58) Field of Classification Search
CPC .... A61K 31/202; A61K 31/205; C07C 59/42; C07C 229/26; C07C 215/10
See application file for complete search history.

(56) References Cited

U.S. PATENT DOCUMENTS

| | | |
|---|---|---|
| 3,055,923 A | 9/1962 | Ginger |
| 5,696,166 A | 12/1997 | Yanni |
| 6,359,158 B1 | 3/2002 | Falck |
| 7,666,447 B2 | 2/2010 | Rockway |
| 7,893,106 B2 | 2/2011 | Arterburn et al. |
| 8,293,790 B2 | 10/2012 | Manku et al. |
| 8,536,223 B2 | 9/2013 | Kelliher et al. |
| 8,729,126 B2* | 5/2014 | Kelliher ............... A61K 31/202 424/278.1 |
| 9,050,308 B2 | 6/2015 | Maines et al. |
| 9,056,086 B2 | 6/2015 | Manku et al. |

(Continued)

FOREIGN PATENT DOCUMENTS

| | | |
|---|---|---|
| EP | 1852114 | 11/2007 |
| EP | 2762143 | 8/2014 |

(Continued)

OTHER PUBLICATIONS

Benno, "Diversified Approach to Acne Care by Using Natural Raw Materials," Fragrance Journal, 35(5):36-41 (May 2007) (with English translation).

(Continued)

*Primary Examiner* — Yate' K Cutliff
(74) *Attorney, Agent, or Firm* — Perkins Coie LLP

(57) ABSTRACT

The present disclosure provides pharmaceutically acceptable stable salt forms of 15-lipoxygenase products, such as 15-HETrE lysine salt, compositions comprising same and methods of making and using same.

3 Claims, 21 Drawing Sheets
(19 of 21 Drawing Sheet(s) Filed in Color)

(56) References Cited

U.S. PATENT DOCUMENTS

| | | | |
|---|---|---|---|
| 9,682,055 B2 | 6/2017 | Manku et al. | |
| 9,889,106 B2 | 2/2018 | Kelliher et al. | |
| 10,105,333 B2 | 10/2018 | Manku et al. | |
| 10,231,945 B2 | 3/2019 | Coughlan et al. | |
| 2002/0052000 A1 | 5/2002 | Parthasarathy | |
| 2002/0055538 A1 | 5/2002 | Serhan et al. | |
| 2005/0239889 A1 | 10/2005 | Gosselin | |
| 2007/0105954 A1 | 5/2007 | Puri | |
| 2010/0233724 A1 | 9/2010 | Watkins et al. | |
| 2011/0059885 A1 | 3/2011 | Lea et al. | |
| 2011/0105510 A1 | 5/2011 | Ishikawa | |
| 2012/0142773 A1* | 6/2012 | Kelliher | A61K 31/202 514/547 |
| 2012/0213824 A1* | 8/2012 | Kelliher | A61K 31/202 424/278.1 |
| 2012/0232147 A1* | 9/2012 | Manku | A61K 31/202 514/560 |
| 2012/0264705 A1 | 10/2012 | Manku et al. | |
| 2012/0264824 A1 | 10/2012 | Mizuguchi et al. | |
| 2013/0101533 A1* | 4/2013 | Manku | A61K 31/202 424/60 |
| 2013/0102575 A1* | 4/2013 | Manku | A61K 31/202 514/171 |
| 2013/0267598 A1 | 10/2013 | Manku et al. | |
| 2013/0274338 A1 | 10/2013 | Manku et al. | |
| 2013/0331448 A1 | 12/2013 | Manku et al. | |
| 2014/0079631 A1 | 3/2014 | Serhan et al. | |
| 2015/0079164 A1 | 3/2015 | Fraser et al. | |

FOREIGN PATENT DOCUMENTS

| | | | |
|---|---|---|---|
| JP | H04507397 | 12/1992 | |
| JP | H05186342 | 7/1993 | |
| JP | H05201924 | 8/1993 | |
| JP | H06128154 | 5/1994 | |
| JP | H07126160 | 5/1995 | |
| JP | AH10500111 | 1/1998 | |
| JP | 2000191525 | 7/2000 | |
| JP | A2003513949 | 4/2003 | |
| JP | A2003525880 | 9/2003 | |
| JP | 2004528360 | 9/2004 | |
| JP | 2005179211 | 7/2005 | |
| JP | 2008167721 | 7/2008 | |
| JP | 2008-543865 | 12/2008 | |
| RU | 94002337 | 8/1996 | |
| RU | 2205004 | 5/2003 | |
| WO | WO 01/34549 | 5/2001 | |
| WO | WO 2001/34549 A1 * | 5/2001 | C07C 59/42 |
| WO | WO 2003/063793 | 8/2003 | |
| WO | WO2004072013 | 8/2004 | |
| WO | WO 2010/125330 A1 * | 11/2010 | A61K 31/202 |
| WO | WO2010125330 | 11/2010 | |
| WO | WO2010125340 | 11/2010 | |
| WO | WO2001034549 | 5/2011 | |
| WO | WO 2013/057284 | 4/2013 | |
| WO | WO2013057284 | 4/2013 | |
| WO | WO2013057287 | 4/2013 | |
| WO | WO2013082265 | 6/2013 | |
| WO | WO2013112876 | 8/2013 | |
| WO | WO2013124479 | 8/2013 | |
| WO | WO 2013/170006 | 11/2013 | |
| WO | WO2013170006 | 11/2013 | |
| WO | WO2014022816 | 2/2014 | |
| WO | WO2014118097 | 8/2014 | |
| WO | WO 2015/106215 | 7/2015 | |
| WO | WO 2016/090030 | 6/2016 | |
| WO | WO 2017/118911 | 7/2017 | |

OTHER PUBLICATIONS

Miller et al., Guinea pig epidermis synthesizes 15-hydroxy-8,11,13-eicosatrienoic acid (15OH-20:3n-6) from dihomogammalinolenic acid: a potent lipoxygenase inhibitor derived from dietary primrose oil, Clinical Research 35(3):704A (1989).

Ziboh et al., "Significance of lipoxygenase-derived monohydroxy fatty acids in cutaneous biology," Prostaglandins & other Lipid Mediators 63(1-2):3-13 (Dec. 2000).

Cho et al., "A novel 15-hydroxyeicosatienoic acid-substituted diacylglycerol (15-HETrE-DAG) selectively inhibits epidermal protein kinase C-[beta]," BBA, Lipids and Lipid Metabolism, VO. 1349, No. 1, pp. 67-71 (1997).

Conrow et al., "Manufacture of (5Z,8Z,11Z,13E)(15S)-15-Hydroxyeicosa-5,8,11,13-tetraenoic Acid Sodium Salt of Clinical Trials,:" Org. Proc. Res. & Dev. 15:301-304 (2011).

Elshof et al. "Biocatalytic hydroxylation of linoleic acid in a double-fed batch system with lipoxygenase and cystine," European Journ. Lipid Sci. and Tech., vol. 100, Nr. 6, S. pp. 246-251 (1998).

Elshof et al. "Biocatalytic large-scale production of 13(S)-hydroperoxy-9(Z), 11(E)-octadecadienoic acid from hydrolysed safflower oil by a crude soybean-flour extract as lipoxygenase source," Rec. Trav. Chim Pays-Bas, 115, 11-12, p. 499-504 (1996).

Flachs et al., "Synergistic induction of lipid catabolism and anti-inflammatory lipids in white fat of dietary obese mice in response to calorie restriction and n-3 fatty acids", 2011, 54:2626-2638.

Johnson et al., "Dietary Supplementation with γ-Linolenic Acid Alters Fatty Acid Content and Eicosanoid Production in Healthy Humans," The Journal of Nutrition. (1997), 127:1435-1444.

Kawamura, A. et al.; "Dietary Supplemental of Gamma-Linolenic Acid Improves Skin Parameters in Subjects with Dry Skin and Atopic Dermatitis"; Journal of oleo Science; vol. 60, No. 12, pp. 597-607, 2011.

Kawashima et al., "Subchronic (13-week) oral toxicity study of dihomo-γ-linolenic acid (DGLA) oil in rats," Food and Chemical Toxicology (2009), 7 pages.

Kendall et al., "Distribution of Bioactive Lipid Mediators in Human Skin," The Journ. of Investigative Dermatology. (2015), 00, 1-11.

Lin, Rong, ed., Pharmaceutical Salts, Water-Insoluble Drug Formulation, Chapter 15, CRC Press, pp. 417-435 (19 pages) (2008).

Miller et al., "Dietary Supplementation with Ethyl Ester Concentrates of Fish Oil (N-3) and Borage Oil (N-6) Polyunsaturated Fatty Acids Induces Epidermal Generation of Local Putative Anti-Inflammatory Metabolites," The Journ. of Invest. Dermatol., vol. 96, No. 1, pp. 98-103 (1991).

Miller et al., "Guinea Pig Epidermis Generates Putative Anti-Inflammatory Metabolites from Fish Oil Polyunsaturated Acids," Lipids, vol. 24, No. 12 (1989).

Miller, C. C. et al.; Induction of Epidermal Hyperproliferation by Topical n-3 Polyunsaturated Fatty Acids on Guinea Pig Skin Linked to Decreased Levels of 13-Hydroxyoctadecadienoic Acid (13-Hode); The Journal of Investigative Dermatology, vol. 94, No. 3, Mar. 1990, 7 pages.

PCT Application No. PCT/IB2014/003027, International Search Report and Written Opinion, dated Apr. 28, 2015, 12 pages.

PCT Application No. PCT/US2015/63488, International Search Report and Written Opinion, dated Feb. 3, 2016, 9 pages.

Swarbrick et al., "Salt Forms of Drugs and Absorption," Encyclopedia of Pharmaceutical Technology 13, Marcel Dekker, Ny, pp. 453-499 (48 pages) (1996).

Benno, "Diversified Approach to Acne Care by Using Natural Raw Materials," Fragrance Journal, 35(5):36-41 (2007) (with English translation).

International Search Report and Written Opinion dated Jun. 6, 2016 for International Application No. PCT/IB2016/000202.

Vang K, et al., "15-lipoxygenase metabolites of gamma-linolenic acid/eicosapentaenoic acid suppress growth and arachidonic acid metabolism in human prostatic adenocarcinoma cells: Possible implications of dietary fatty acids", Prostaglandins Leukotrienes and essential fatty acids, Churchill Lingstone, Edinburgh, vol. 72, No. 5, pp. 363-372 (2005).

Cho et al., "A novel 15-hydroxyeicosatienoic acid-substituted diacylglycerol (15-HETrE-DAG) selectively inhibits epidermal protein kinase C-[beta],"Biochimica ET Biophysica Acta (BBA)—Lipids and Lipid Metabolism, 1349(1):67-71 (publication date: Nov. 8, 1997).

(56) References Cited

OTHER PUBLICATIONS

Conrow et al., "Manufacture of (5Z,8Z,11Z,13E)(15S)-15-Hydroxyeicosa-5,8,11,13-tetraenoic Acid Sodium Salt of Clinical Trials,:" Org. Proc. Res. & Dev. 15:301-304 (epublication date: Dec. 2, 2010).

Das, "A defect in the activities of $\Delta^6$ and $\Delta^5$ desaturases and pro-resolution bioactive lipids in the pathobiology of non-alcoholic fatty liver disease," World Journal of Diabetes 2(11):176-188 (publication date: Nov. 15, 2011).

Elshof et al. "Biocatalytic hydroxylation of linoleic acid in a double-fed batch system with lipoxygenase and cystine," European Journ. Lipid Sci. And Tech., vol. 100, Nr. 6, S. pp. 246-251 (publication date: Jan. 28, 1999).

Elshof et al. "Biocatalytic large-scale production of 13(S)-hydroperoxy-9(Z), 11(E)-octadecadienoic acid from hydrolysed safflower oil by a crude soybean-flour extract as lipoxygenase source," Rec. Trav. Chim Pays-Bas, 115, 11-12, p. 499-504 (epublication date: Sep. 2, 2010).

Ishii et al., "Eicosapentaenoic acid ameliorates steatohepatitis and hepatocellular carcinoma in hepatocyte-specific Pten-deficient mice", Journal of Hepatology, 2009, pp. 562-571 (publication date: Mar. 1, 2009, epublication date: Dec. 27, 2008).

Kawashima et al., "Subchronic (13-week) oral toxicity study of dihomo-y-linolenic acid (DGLA) oil in rats," Food and Chemical Toxicology, 7 pages (publication date: Jun. 2009, epublication date: Mar. 9, 2009).

Liu et al., Water-Insoluble Drug Formulation, CRC Press, Chapter 15, "Pharmaceutical Salts," pp. 417-435 (19 pages) (publication date: Jan. 18, 2008).

Masterton et al., "Review article: omega-3 fatty acids—a promising novel therapy for non-alcoholic fatty liver disease," Alimentary Pharmacology & Therapeutics, 31(7):679-692 (publication date: Apr. 30, 2010, epublication date: Mar. 1, 2010).

Nguyen et al., "Mechanisms for anti-inflammatory effects of 1-[15(S)-hydroxyeicosapentaenoyl] lysophosphatidylcholine, administered intraperitoneally, in zymosan A—induced peritonitis," British Journal of Pharmacology 162(5):1119-1135 (publication date: Mar. 2011, epublication date: Nov. 22, 2010).

Tanaka, Naoki et al., "Highly Purified Eicosapentaenoic Acid Treatment Improves Nonalcoholic Steatohepatitis," Journal of Clinical Gastroenterology, vol. 42, No. 4, pp. 413-418 (publication date: Apr. 1, 2008).

Ziboh et al., "Significance of lipoxygenase-derived monohydroxy fatty acids in cutaneous biology," Prostaglandins & other Lipid Mediators 63(1-2):3-13 (publication date: Nov. 2000).

Dignity Sciences Limited, "Oral DS107G in Moderate to Severe Atopic Dermatitis," ClinicalTrials.gov (Study start date: Jan. 2015).

Iversen et al.,"Effect of dihomogammalinolenic acid and its 15-lipoxygenase metabolite on eicosanoid metabolism by human mononuclear leukocytes in vitro: selective inhibition of the 5-lipoxygenase pathway," Arch Dermatol Res 284(4):222-226 (publication date: Aug. 1992).

Jancin et al., "Bioactive lipid shows promise in atopic dermatitis," Dermatology News (publication date: Nov. 9, 2016).

Miller et al., "Guinea Pig Epidermis Generates Putative Anti-Inflammatory Metabolites from Fish Oil Polyunsaturated Acids," Lipids 24(12):998-1003 (publication date: Dec. 1989).

Miller et al., "Guinea pig epidermis synthesizes 15-hydroxy-8,11,13-eicosatrienoic acid (15-OH-20:3n6) from dihomogammalinolenic acid (DGLA): a potent lipoxygenase inhibitor derived from dietary primrose oil," Clinical Research 35(3):704A (publication date: Apr. 1987).

Reddy et al., "Conversion of Dihomo-γ-Linolenic Acid to Mono- and Dihydroxy Acids by Potato Lipoxygenase: Evidence for the Formation of 8,9-Leukotriene A3," Archives of Biochemistry and Biophysics 279(2):211-217 (publication date: May 15, 1990).

Simon et al., "Gamma-Linolenic Acid Levels Correlate with Clinical Efficacy of Evening Primrose Oil in Patients with Atopic Dermatitis," Advances in Therapy 31(2):180-188 (publication date: Feb. 2014, epublictaion date: Jan. 17, 2014).

Wheelock et al, "Allergic Asthmatics exhibit altered response in oxylipin profile as compared to healthy and asthmatic controls after allergen provocation," American Journal of Respiratory and Critical Care Medicine, 183:1 (2011) (Abstract only).

Yin et al., "Identification of Novel Autoxidation Products of the ω-3 Fatty Acid Eicosapentaenoic Acid in Vitro and in Vivo," Journal of Biological Chemistry 282(41):29890-29901 (publication date: Oct. 12, 2007, epublication date: Aug. 21, 2007).

\* cited by examiner

PHARMACEUTICALLY ACCEPTABLE SALTS OF FATTY ACIDS

PRIORITY CLAIM

This application claims priority to U.S. Provisional Patent Application Ser. No. 61/904,600, filed Nov. 15, 2013, the entire contents of which are incorporated herein by reference and relied upon.

FIELD

The disclosure generally relates to pharmaceutically acceptable stable salt forms of 15-lipoxygenase products.

BACKGROUND

Enzymes are highly selective catalysts, greatly accelerating both the rate and specificity of biochemical reactions. In enzymatic reactions, the molecules at the beginning of the process, called substrates, are converted into different molecules, called products.

Lipoxygenases are enzymes that catalyze the oxidation of polyunsaturated fatty acids. 15-lipoxygenase (15-LOX) is one such enzyme that catalyzes the oxidation of substrates such as linolenic acid, dihomo-gamma linolenic acid, eicosapentaenoic acid and arachidonic acid to the respective products 13-HODE, 15-HETrE, 15-OHEPA and 15-HETE.

15-LOX is responsible for the conversion of arachidonic acid to various biologically active metabolites including 15-hydroxy-5,8,11,13-eicosatetraenoic acid (15-HETE). 15-HETE has been implicated in the pathogenesis of airway and allergic diseases such as asthma by contributing to bronchoconstriction, mucus secretion, and eosinophil migration. While 15-HETE has been implicated in proinflammatory reactions, other 15-LOX products, such as 15-OHEPA, 15-HETrE and 13-HODE, have been shown to have anti-inflammatory effects and may be medically useful.

Examples of potential medically useful indications for 15-LOX products, incorporated by reference, include, but are not limited to acne therapy (U.S. Pat. No. 8,293,790), erythema therapy (US patent application publication 2013/0101533), anti-microbials (US patent application publication 2012/0264705), fatty liver therapy (GB1300628.3), neuropathy therapy (WO2010/125330A1) and treatment for skin inflammation (U.S. Pat. No. 8,536,223).

The products of 15-LOX metabolism are unstable at room temperature and need to be stored at temperatures of −20° C. or less. Due to this instability, 15-LOX products have not been formulated for medical use. As shown below, an issue with these compounds is the tendency for the 15-LOX derived hydroxyl group to form fatty acid dimers by forming ester bonds with the carboxyl group of the fatty acid.

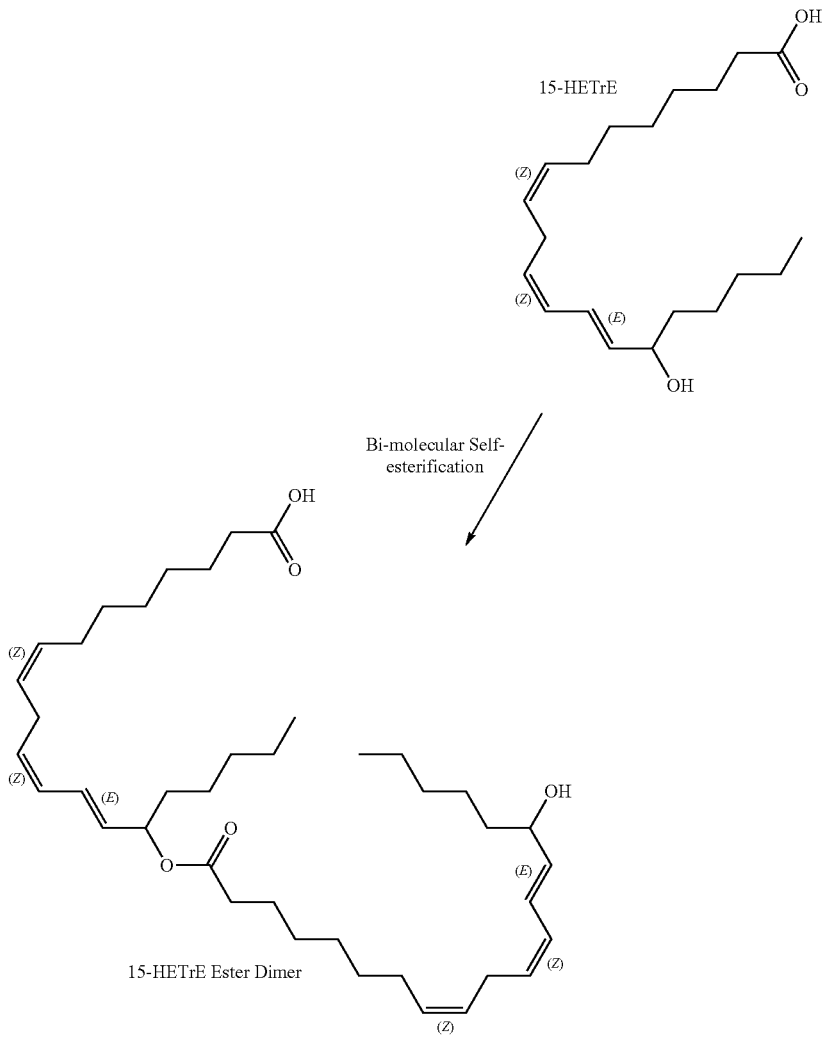

Because of the instability and dimer formation, their potential to be developed as a medicine has been a challenge. Pharmaceutically acceptable stable forms of 15-LOX products are described herein.

SUMMARY

The present disclosure provides compositions comprising stable, pharmaceutically useful salts of 15-lipoxygenase fatty acid products.

The invention also provides pharmaceutical compositions comprising any of the compounds described herein and a pharmaceutically acceptable carrier.

In some embodiments the, the fatty acids are 15-HETrE, 15-OHEPA or 13-HODE. In another embodiment the salt forms are sodium or lysine salts of 15-HETrE, 15-OHEPA or 13-HODE. In a specific embodiment, the invention is a lysine salt of 15-HETrE.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

DETAILED DESCRIPTION

Figure 1:
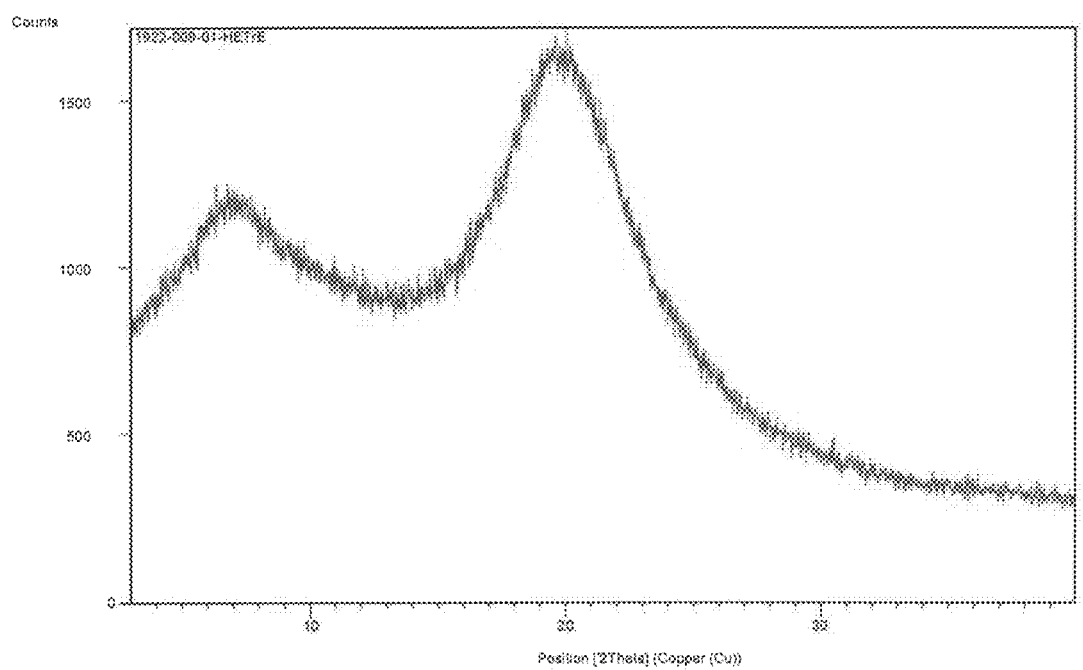
FIG. 1 shows the X-ray powder diffraction pattern of 15-HETrE.

13-HODE is formed by the action of 15-LOX on linoleic acid. Linoleic acid is oxidized to 13-hydroperoxyoctadeca-9Z,11E-dienoic acid (13-HODE). As used herein, the term "13-HODE" refers to 13-HODE in its free acid form.

15-Hydroxy-eicosa-8(Z),11(Z),13(E)-trienoic acid ("15-HETrE" or "HETrE") is a 15-LOX derivative of dihomo-gamma linolenic acid (DGLA). 15-HETrE can be synthesized from DGLA according to methods in the art. As used herein, the term "15-HETrE" refers to 15-HETrE in its free acid form (e.g, 15-hydroxy-eicosa-8(Z),11(Z),13(E)-trienoic acid).

15-Hydroxy-eicosa-5(Z),8(Z),11(Z),13(E),17(Z)-pentaenoic acid ("15-OHEPA") is a 15-LOX derivative of EPA. 15-OHEPA can be synthesized from EPA according to methods known in the art. As used herein, the term "15-OHEPA" refers to 15-OHEPA in its free acid form (e.g, 15-hydroxy-eicosa-5,8,11,13,17-pentaenoic acid).

As used herein, the term "pharmaceutically useful" refers to compounds and/or compositions that are chemically and physically compatible (e.g., substantially miscible and/or nonreactive) with other pharmaceutical components, or to pharmaceutical compositions that are generally stable under common storage conditions (e.g., room temperature or refrigerated) for a length of time sufficient to provide a commercially viable shelf life.

In various embodiments, the invention provides pharmaceutical compositions, for example topically deliverable compositions, comprising one or more of 13-HODE, 15-OHEPA, 15-HETrE or mixtures thereof.

In one embodiment, the present disclosure provides topical pharmaceutical compositions comprising, for example, an amount (e.g., a therapeutically effective amount) of a salt form of 13-HODE, 15-OHEPA, 15-HETrE, or a combination thereof. In one embodiment, the pharmaceutical composition comprises about 0.1 wt. % to about 20 wt. % of the 13-HODE, 15-OHEPA, 15-HETrE, or a combination thereof, for example about 0.1 wt. %, about 0.2 wt. %, about 0.3 wt. %, about 0.4 wt. %, about 0.5 wt. %, about 0.6 wt. %, about 0.7 wt. %, about 0.8 wt. %, about 0.9 wt. %, about 1 wt. %, about 1.1 wt. %, about 1.2 wt. %, about 1.3 wt. %, about 1.4 wt. %, about 1.5 wt. %, about 1.6 wt. %, about 1.7 wt. %, about 1.8 wt. %, about 1.9 wt. %, about 2 wt. %, about 2.1 wt. %, about 2.2 wt. %, about 2.3 wt. %, about 2.4 wt. %, about 2.5 wt. %, about 2.6 wt. %, about 2.7 wt. %, about 2.8 wt. %, about 2.9 wt. %, about 3 wt. %, about 3.1 wt. %, about 3.2 wt. %, about 3.3 wt. %, about 3.4 wt. %, about 3.5 wt. %, about 3.6 wt. %, about 3.7 wt. %, about 3.8 wt. %, about 3.9 wt. %, about 4 wt. %, about 4.1 wt. %, about 4.2 wt. %, about 4.3 wt. %, about 4.4 wt. %, about 4.5 wt. %, about 4.6 wt. %, about 4.7 wt. %, about 4.8 wt. %, about 4.9 wt. %, about 5 wt. %, about 5.1 wt. %, about 5.2 wt. %, about 5.3 wt. %, about 5.4 wt. %, about 5.5 wt. %, about 5.6 wt. %, about 5.7 wt. %, about 5.8 wt. %, about 5.9 wt. %, about 6 wt. %, about 6.1 wt. %, about 6.2 wt. %, about 6.3 wt. %, about 6.4 wt. %, about 6.5 wt. %, about 6.6 wt. %, about 6.7 wt. %, about 6.8 wt. %, about 6.9 wt. %, about 7 wt. %, about 7.1 wt. %, about 7.2 wt. %, about 7.3 wt. %, about 7.4 wt. %, about 7.5 wt. %, about 7.6 wt. %, about 7.7 wt. %, about 7.8 wt. %, about 7.9 wt. %, about 8 wt. %, about 8.1 wt. %, about 8.2 wt. %, about 8.3 wt. %, about 8.4 wt. %, about 8.5 wt. %, about 8.6 wt. %, about 8.7 wt. %, about 8.8 wt. %, about 8.9 wt. %, about 9 wt. %, about 9.1 wt. %, about 9.2 wt. %, about 9.3 wt. %, about 9.4 wt. %, about 9.5 wt. %, about 9.6 wt. %, about 9.7 wt. %, about 9.8 wt. %, about 9.9 wt. %, about 10 wt. %, about 10.1 wt. %, about 10.2 wt. %, about 10.3 wt. %, about 10.4 wt. %, about 10.5 wt. %, about 10.6 wt. %, about 10.7 wt. %, about 10.8 wt. %, about 10.9 wt. %, about 11 wt. %, about 11.1 wt. %, about 11.2 wt. %, about 11.3 wt. %, about 11.4 wt. %, about 11.5 wt. %, about 11.6 wt. %, about 11.7 wt. %, about 11.8 wt. %, about 11.9 wt. %, about 12 wt. %, about 12.1 wt. %, about 12.2 wt. %, about 12.3 wt. %, about 12.4 wt. %, about 12.5 wt. %, about 12.6 wt. %, about 12.7 wt. %, about 12.8 wt. %, about 12.9 wt. %, about 13 wt. %, about 13.1 wt. %, about 13.2 wt. %, about 13.3 wt. %, about 13.4 wt. %, about 13.5 wt. %, about 13.6 wt. %, about 13.7 wt. %, about 13.8 wt. %, about 13.9 wt. %, about 14 wt. %, about 14.1 wt. %, about 14.2 wt. %, about 14.3 wt. %, about 14.4 wt. %, about 14.5 wt. %, about 14.6 wt. %, about 14.7 wt. %, about 14.8 wt. %, about 14.9 wt. %, about 15 wt. %, about 15.1 wt. %, about 15.2 wt. %, about 15.3 wt. %, about 15.4 wt. %, about 15.5 wt. %, about 15.6 wt. %, about 15.7 wt. %, about 15.8 wt. %, about 15.9 wt. %, about 16 wt. %, about 16.1 wt. %, about 16.2 wt. %, about 16.3 wt. %, about 16.4 wt. %, about 16.5 wt. %, about 16.6 wt. %, about 16.7 wt. %, about 16.8 wt. %, about 16.9 wt. %, about 17 wt. %, about 17.1 wt. %, about 17.2 wt. %, about 17.3 wt. %, about 17.4 wt. %, about 17.5 wt. %, about 17.6 wt. %, about 17.7 wt. %, about 17.8 wt. %, about 17.9 wt. %, about 18 wt. %, about 18.1 wt. %, about 18.2 wt. %, about 18.3 wt. %, about 18.4 wt. %, about 18.5 wt. %, about 18.6 wt. %, about 18.7 wt. %, about 18.8 wt. %, about 18.9 wt. %, about 19 wt. %, about 19.1 wt. %, about 19.2 wt. %, about 19.3 wt. %, about 19.4 wt. %, about 19.5 wt. %, about 19.6 wt. %, about 19.7 wt. %, about 19.8 wt. %, about 19.9 wt. %, or about 20 wt. % of the 13-HODE, 15-OHEPA, 15-HETrE, or a combination thereof.

Any pharmaceutically acceptable excipient known to those of skill in the art may be used in pharmaceutical compositions according to the present disclosure. Any excipient selected for use in the therapeutic and cosmetic compositions should be pharmaceutically and/or cosmetically acceptable and appropriate for the form in which the therapeutic composition will be used, e.g., cream, gel, milk, oil, lotion, and the like. Preferably, the excipient has an affinity for the skin, is well tolerated, and stable when used in an amount adequate to provide the desired consistency and ease of application. By way of example only, a pharmaceutical composition according to the present disclosure may comprise one or more of: surfactants, preservatives, flavoring agents, co-solvents, viscosity aids, suspension aids, and lipophilic phases.

In another aspect, the present invention provides a pharmaceutical composition comprising a therapeutically effective amount of a salt form of 15-HETrE, 15-OHEPA or 13-HODE. The salt form of 15-HETrE, 15-OHEPA or 13-HODE may be the sole significant active ingredient in that composition and in the methods and uses as stated herein. The salt form of 15-HETrE, 15-OHEPA or 13-HODE may be the sole active ingredient. Alternatively, the salt form of 15-HETrE, 15-OHEPA or 13-HODE may be combined for co-formulation or co-administration with other agents for treating a disease or disorder. If an additional active agent is to be used, the salt form of 15-HETrE, 15-OHEPA or 13-HODE can be co-formulated as a single dosage unit or can be formulated as two to a plurality of dosage units for coordinated, combination or concomitant administration.

In various embodiments, the invention provides pharmaceutical compositions, for example orally deliverable compositions, comprising the salt form of 15-HETrE, 15-OHEPA or 13-HODE. In one embodiment, the compositions comprise a therapeutically effective amount of the salt form of 15-HETrE, 15-OHEPA or 13-HODE. In one embodiment, the pharmaceutical composition comprises about 0.1% to about 99.9%, about 1% to about 95%, or about 5% to about 90% by weight of the salt form of 15-HETrE, 15-OHEPA or 13-HODE, for example about 1%, about 2%, about 3%, about 4%, about 5%, about 6%, about 7%, about 8%, about 9%, about 10%, about 11%, about 12%, about 13%, about 14%, about 15%, about 16%, about 17%, about 18%, about 19%, about 20%, about 21%, about 22%, about 23%, about 24%, about 25%, about 26%, about 27%, about 28%, about 29%, about 30%, about 31%, about 32%, about 33%, about 34%, about 35%, about 36%, about 37%, about 38%, about 39%, about 40%, about 41%, about 42%, about 43%, about 44%, about 45%, about 46%, about 47%, about 48%, about 49%, about 50%, about 51%, about 52%, about 53%, about 54%, about 55%, about 56%, about 57%, about 58%, about 59%, about 60%, about 61%, about 62%, about 63%, about 64%, about 65%, about 66%, about 67%, about 68%, about 69%, about 70%, about 71%, about 72%, about 73%, about 74%, about 75%, about 76%, about 77%, about 78%, about 79%, about 80%, about 81%, about 82%, about 83%, about 84%, about 85%, about 86%, about 87%, about 88%, about 89%, about 90%, about 91%, about 92%, about 93%, about 94%, about 95%, about 96%, about 97%, about 98%, about 99%, about 99.5%, or about 99.9% by weight of the salt form of 15-HETrE, 15-OHEPA or 13-HODE.

In one embodiment, the pharmaceutical composition comprises about at least about 70%, %, at least about 71%, at least about 72%, at least about 73%, at least about 74%, at least about 75%, at least about 76%, at least about 77%, at least about 78%, at least about 79%, at least about 80%, at least about 81%, at least about 82%, at least about 83%, at least about 84%, at least about 85%, at least about 86%, at least about 87%, at least about 88%, at least about 89%, at least about 90%, at least about 91%, at least about 92%, at least about 93%, at least about 94%, at least about 95%, at least about 96%, at least about 97%, at least about 98%, at least about 99%, at least about 99.5%, or about 99.9%, by weight, of the salt form of 15-HETrE, 15-OHEPA or 13-HODE.

In one embodiment, the pharmaceutical composition comprises at least about 50%, at least about 60%, at least about 70%, at least about 80% or at least about 90%, by weight of the salt form of 15-HETrE, 15-OHEPA or 13-HODE.

In another embodiment, the salt form of 15-HETrE, 15-OHEPA or 13-HODE is present in a composition of the invention in an amount of about 1 mg to about 10,000 mg, about 25 mg to about 7500 mg, about 25 mg to about 5000 mg, about 50 mg to about 5000 mg, about 50 mg to about 3000 mg, about 75 mg to about 2500 mg, or about 100 mg to about 1000 mg, for example about 1 mg, about 2 mg, about 3 mg, about 4 mg, about 5 mg, about 6 mg, about 7 mg, about 8 mg, about 9 mg, about 10 mg, about 11 mg, about 12 mg, about 13 mg, about 14 mg, about 15 mg, about 16 mg, about 17 mg, about 18 mg, about 19 mg, about 20 mg, about 21 mg, about 22 mg, about 23 mg, about 24 mg, about 25 mg, about 50 mg, about 75 mg, about 100 mg, about 125 mg, about 150 mg, about 175 mg, about 200 mg, about 225 mg, about 250 mg, about 275 mg, about 300 mg, about 325 mg, about 350 mg, about 375 mg, about 400 mg, about 425 mg, about 450 mg, about 475 mg, about 500 mg, about 525 mg, about 550 mg, about 575 mg, about 600 mg, about 625 mg, about 650 mg, about 675 mg, about 700 mg, about 725 mg, about 750 mg, about 775 mg, about 800 mg, about 825 mg, about 850 mg, about 875 mg, about 900 mg, about 925 mg, about 950 mg, about 975 mg, about 1000 mg, about 1025 mg, about 1050 mg, about 1075 mg, about 1100 mg, about 1025 mg, about 1050 mg, about 1075 mg, about 1200 mg, about 1225 mg, about 1250 mg, about 1275 mg, about 1300 mg, about 1325 mg, about 1350 mg, about 1375 mg, about 1400 mg, about 1425 mg, about 1450 mg, about 1475 mg, about 1500 mg, about 1525 mg, about 1550 mg, about 1575 mg, about 1600 mg, about 1625 mg, about 1650 mg, about 1675 mg, about 1700 mg, about 1725 mg, about 1750 mg, about 1775 mg, about 1800 mg, about 1825 mg, about 1850 mg, about 1875 mg, about 1900 mg, about 1925 mg, about 1950 mg, about 1975 mg, about 2000 mg, about 2025 mg, about 2050 mg, about 2075 mg, about 2100 mg, about 2125 mg, about 2150 mg, about 2175 mg, about 2200 mg, about 2225 mg, about 2250 mg, about 2275 mg, about 2300 mg, about 2325 mg, about 2350 mg, about 2375 mg, about 2400 mg, about 2425 mg, about 2450 mg, about 2475 mg, about 2500 mg, 2525 mg, about 2550 mg, about 2575 mg, about 2600 mg, about 2625 mg, about 2650 mg, about 2675 mg, about 2700 mg, about 2725 mg, about 2750 mg, about 2775 mg, about 2800 mg, about 2825 mg, about 2850 mg, about 2875 mg, about 2900 mg, about 2925 mg, about 2950 mg, about 2975 mg, about 3000 mg, about 3025 mg, about 3050 mg, about 3075 mg, about 3100 mg, about 3125 mg, about 3150 mg, about 3175 mg, about 3200 mg, about 3225 mg, about 3250 mg, about 3275 mg, about 3300 mg, about 3325 mg, about 3350 mg, about 3375 mg, about 3400 mg, about 3425 mg, about 3450 mg, about 3475 mg, about 3500 mg, about 3525 mg, about 3550 mg, about 3575 mg, about 3600 mg, about 3625 mg, about 3650 mg, about 3675 mg, about 3700 mg, about 3725 mg, about 3750 mg, about 3775 mg, about 3800 mg, about 3825 mg, about 3850 mg, about 3875 mg, about 3900 mg, about 3925 mg, about 3950 mg, about 3975 mg, about 4000 mg, about 4025 mg, about 4050 mg, about 4075 mg, about 4100 mg, about 4125 mg, about 4150 mg, about 4175 mg, about 4200 mg, about 4225 mg, about 4250 mg, about 4275 mg, about 4300 mg, about 4325 mg, about 4350 mg, about 4375 mg, about 4400 mg, about 4425 mg, about 4450 mg, about 4475 mg, about 4500 mg, about 4525 mg, about 4550 mg, about 4575 mg, about 4600 mg, about 4625 mg, about 4650 mg, about 4675 mg, about 4700 mg, about 4725 mg, about 4750 mg, about 4775 mg, about 4800 mg, about 4825 mg, about 4850 mg, about 4875 mg, about 4900 mg, about 4925 mg, about 4950 mg, about 4975 mg, about 5000 mg, about 5025 mg, about 5050 mg, about 5075 mg, about 5100 mg, about 5125 mg, about 5150 mg, about 5175 mg, about 5200 mg, about 5225 mg, about 5250 mg, about 5275 mg, about 5300 mg, about 5325 mg, about 5350 mg, about 5375 mg, about 5400 mg, about 5425 mg, about 5450 mg, about 5475 mg, about 5500 mg, about 5525 mg, about 5550 mg, about 5575 mg, about 5600 mg, about 5625 mg, about 5650 mg, about 5675 mg, about 5700 mg, about 5725 mg, about 5750 mg, about 5775 mg, about 5800 mg, about 5825 mg, about 5850 mg, about 5875 mg, about 5900 mg, about 5925 mg, about 5950 mg, about 5975 mg, about 6000 mg, about 6025 mg, about 6050 mg, about 6075 mg, about 6100 mg, about 6125 mg, about 6150 mg, about 6175 mg, about 6200 mg, about 6225 mg, about 6250 mg, about 6275 mg, about 6300 mg, about 6325 mg, about 6350 mg, about 6375 mg, about 6400 mg, about 6425 mg, about 6450 mg, about 6475 mg, about 6500 mg, about 6525 mg, about 6550 mg, about 6575 mg, about 6600 mg, about 6625 mg, about 6650 mg, about 6675 mg, about 6700 mg, about 6725 mg, about 6750 mg, about 6775 mg, about 6800 mg, about 6825 mg, about 6850 mg, about 6875 mg, about 6900 mg, about 6925 mg, about 6950 mg, about 6975 mg, about 7000 mg, about 7025 mg, about 7050 mg, about 7075 mg, about 7100 mg, about 7125 mg, about 7150 mg, about 7175 mg, about 7200 mg, about 7225 mg, about 7250 mg, about 7275 mg, about 7300 mg, about 7325 mg, about 7350 mg, about 7375 mg, about 7400 mg, about 7425 mg, about 7450 mg, about 7475 mg, about 7500 mg, about 7525 mg, about 7550 mg, about 7575 mg, about 7600 mg, about 7625 mg, about 7650 mg, about 7675 mg, about 7700 mg, about 7725 mg, about 7750 mg, about 7775 mg, about 7800 mg, about 7825 mg, about 7850 mg, about 7875 mg, about 7900 mg, about 7925 mg, about 7950 mg, about 7975 mg, about 8000 mg, about 8025 mg, about 8050 mg, about 8075 mg, about 8100 mg, about 8125 mg, about 8150 mg, about 8175 mg, about 8200 mg, about 8225 mg, about 8250 mg, about 8275 mg, about 8300 mg, about 8325 mg, about 8350 mg, about 8375 mg, about 8400 mg, about 8425 mg, about 8450 mg, about 8475 mg, about 8500 mg, about 8525 mg, about 8550 mg, about 8575 mg, about 8600 mg, about 8625 mg, about 8650 mg, about 8675 mg, about 8700 mg, about 8725 mg, about 8750 mg, about 8775 mg, about 8800 mg, about 8825 mg, about 8850 mg, about 8875 mg, about 8900 mg, about 8925 mg, about 8950 mg, about 8975 mg, about 9000 mg, about 9025 mg, about 9050 mg, about 9075 mg, about 9100 mg, about 9125 mg, about 9150 mg, about 9175 mg, about 9200 mg, about 9225 mg, about 9250 mg, about 9275 mg, about 9300 mg, about 9325 mg, about 9350 mg, about 9375 mg, about 9400 mg, about 9425 mg, about 9450 mg, about 9475 mg, about 9500 mg, about 9525 mg, about 9550 mg, about 9575 mg, about 9600 mg, about 9625 mg, about 9650 mg, about 9675 mg, about 9700 mg, about 9725 mg, about 9750 mg, about 9775 mg, about 9800 mg, about 9825 mg, about 9850 mg, about 9875 mg, about 9900 mg, about 9925 mg, about 9950 mg, about 9975 mg, or about 10,000 mg.

In one embodiment, the salt form of 15-HETrE, 15-OHEPA or 13-HODE present in a composition of the invention comprises at least 90% by weight of the salt form of 15-HETrE, 15-OHEPA or 13-HODE. Compositions containing the salt form of 15-HETrE, 15-OHEPA or 13-HODE can comprise even higher purity, for example at least 91% by weight, at least 92% by weight, at least 93% by weight, at least 94% by weight, at least 95% by weight, at least 96% by weight or at least 97% by weight of the salt form of 15-HETrE, 15-OHEPA or 13-HODE.

In one embodiment, the present disclosure provides a salt of a 15-lipoxygenase product. In some embodiments, the salt is a pharmaceutically acceptable salt. In some embodiments, the salt comprises a lysine salt of the 15-lipoxygenase product. In some embodiments, the salt comprises a sodium salt of the 15-lipoxygenase product. In some embodiments, the salt comprises an ornithine salt of the 15-lipoxygenase product. In some embodiments, the salt comprises a piperazine salt of the 15-lipoxygenase product. In some embodiments, the salt comprises a meglumine salt of the 15-lipoxygenase product. In some embodiments, the salt further comprising the 15-lipoxygenase product in free acid form. In some embodiments, the salt is selected from the group consisting of: sodium, lysine, ornithine, piperazine, meglumine, and combinations thereof. In some embodiments, the salt is a sodium salt. In some embodiments, the salt is a lysine salt. In some embodiments, the salt is ornithine. In some embodiments, the salt is a piperazine salt. In some embodiments, the salt is a meglumine salt. In some embodiments, the 15-lipoxygenase product is selected from the group consisting of: 13-HODE, 15-HETrE, 15-OHEPA, 15-HETE, and combinations thereof. In some embodiments, the 15-lipoxygenase product is 13-HODE. In some embodiments, the 15-lipoxygenase product is 15-HETrE. In some embodiments, the 15-lipoxygenase product is 15-OHEPA. In some embodiments, the 15-lipoxygenase product is 15-HETE.

In some embodiments, the present disclosure provides a salt of 13-hydroperoxyoctadeca-9Z,11E-dienoic acid. In some embodiments, the salt is a sodium salt. In some embodiments, the salt is a lysine salt. In some embodiments, the salt is an ornithine salt. In some embodiments, the salt is a piperazine salt. In some embodiments, the salt is a meglumine salt.

In some embodiments, the present disclosure provides a salt of 15-hydroxy-eicosa-8(Z),11(Z),13(E)-trienoic acid. In some embodiments, the salt is a sodium salt. In some embodiments, the salt is a lysine salt. In some embodiments, the salt is an ornithine salt. In some embodiments, the salt is a piperazine salt. In some embodiments, the salt is a meglumine salt.

In some embodiments, the present disclosure provides a salt of 15-hydroxy-eicosa-5(Z),8(Z),11(Z),13(Z),17(Z)-pentaenoic acid. In some embodiments, the salt is a sodium salt. In some embodiments, the salt is a lysine salt. In some embodiments, the salt is an ornithine salt. In some embodiments, the salt is a piperazine salt. In some embodiments, the salt is a meglumine salt.

In some embodiments, the present disclosure provides a salt of 15-hydroxy-5,8,11,13-eicosatetraenoic acid. In some embodiments, the salt is a sodium salt. In some embodiments, the salt is a lysine salt. In some embodiments, the salt is an ornithine salt. In some embodiments, the salt is a piperazine salt. In some embodiments, the salt is a meglumine salt.

In some embodiments, the present disclosure provides a composition comprising a salt of 13-hydroperoxyoctadeca-9Z, 11E-dienoic acid, 15-hydroxy-eicosa-8(Z),11(Z),13(E)-trienoic acid, 15-hydroxy-eicosa-5(Z),8(Z),11(Z),13(Z),17 (Z)-pentaenoic acid, and/or 15-hydroxy-5,8,11,13-eicosatetraenoic acid. In some embodiments, the salt comprises or is a sodium salt. In some embodiments, the salt comprises or is a lysine salt. In some embodiments, the salt comprises or is an ornithine salt. In some embodiments, the salt comprises or is a piperazine salt. In some embodiments, the salt comprises or is a meglumine salt.

In some embodiments, the present disclosure provides a pharmaceutical composition comprising a salt form of a 15-lipoxygenase product. In some embodiments, the salt form of the 15-lipoxygenase product comprises the salt of any one or more of 13-hydroperoxyoctadeca-9Z, 11E-dienoic acid, 15-hydroxy-eicosa-8(Z), 11(Z),13 (E)-trienoic acid, 15-hydroxy-eicosa-5(Z),8(Z),11(Z),13(Z),17(Z)-pentaenoic acid, and/or 15-hydroxy-5,8,11,13-eicosatetraenoic acid. In some embodiments, the pharmaceutical composition further comprises an excipient.

In some embodiments, after storage for at least about 4 weeks, the pharmaceutical composition comprises at least about 98%, at least about 99%, or about 100% of the initial amount of the salt form of the 15-lipoxygenase product. In some embodiments, after storage for at least about 10 weeks, the pharmaceutical composition comprises at least about 90%, at least about 91%, at least about 92%, at least about 93%, at least about 94%, at least about 95%, at least about 96%, at least about 97%, at least about 98%, at least about 99%, or about 100% of an initial amount of the salt form of the 15-lipoxygenase product. In some embodiments, after storage for at least about 24 weeks, the pharmaceutical composition comprises at least about 86%, at least about 87%, at least about 88%, at least about 89%, at least about 90%, at least about 91%, at least about 92%, at least about 93%, at least about 94%, at least about 95%, at least about 96%, at least about 97%, at least about 98%, at least about 99%, or about 100% of an initial amount of the salt form of the 15-lipoxygenase product. In any of the foregoing embodiments, the pharmaceutical composition may be stored at 2-8° C., at 20° C., at 25° C., or at 40° C. In some embodiments, the pharmaceutical composition is stored at 60% RH or at 75% RH.

In some embodiments, the pharmaceutical composition comprises a therapeutically effective amount of the salt of the 15-lipoxygenase product. In some embodiments, the therapeutically effective amount of the salt form of the 15-lipoxygenase product is about 0.1 wt. % to about 20 wt. %.

In some embodiments, the pharmaceutical composition is in a form suitable for topical administration.

In some embodiments, the salt form of the 15-lipoxygenase product is the sole significant active ingredient or the sole active ingredient in the pharmaceutical composition. In other embodiments, the pharmaceutical composition further comprises an additional active agent.

In some embodiments, the salt form of the 15-lipoxygenase product and the additional active agent are co-formulated as a single dosage unit. In some embodiments, the salt form of the 15-lipoxygenase product and the additional active agent are formulated as at least two dosage units for coordinated, combined or concomitant administration.

The invention includes a therapeutic method for treating or ameliorating a disease or disorder responsive to a 15-LOX product in a subject in need thereof comprising administering to a subject in need thereof an effective amount of an salt form of a 15-LOX product disclosed herein.

Administration methods include administering an effective amount of a compound or composition of the invention at different times during the course of therapy or concurrently in a combination form. The methods of the invention include all known therapeutic treatment regimens.

"Effective amount" means that amount of drug substance (i.e. salt forms of 15-LOX products of the present invention) that elicits the desired biological response in a subject. Such response includes alleviation of the symptoms of the disease or disorder being treated. The effective amount of a disclosed salt form of a 15-LOX product in such a therapeutic method is from about 0.001 mg/kg/day to about 100 mg/kg/day, 0.01 mg/kg/day to about 10 mg/kg/day, preferably from about 0.5 mg/kg/day to 5 mg/kg/day.

The invention includes the use of a disclosed salt form of a 15-LOX product for the preparation of a composition for treating or ameliorating a chronic disorder or disease or infection in a subject in need thereof, wherein the composition comprises a mixture of one or more of the disclosed salt forms of a 15-LOX product and an optional pharmaceutically acceptable carrier.

"Pharmaceutically acceptable carrier" means compounds and compositions that are of sufficient purity and quality for use in the formulation of a composition of the invention that, when appropriately administered to an animal or human, do not produce an adverse reaction, and that are used as a vehicle for a drug substance (i.e. salt forms of a 15-LOX product of the present invention). "Pharmaceutically acceptable carrier" shall also include material that (i) is compatible with the other ingredients of the composition without rendering the composition unsuitable for its intended purpose, and (ii) is suitable for use with subjects as provided herein without undue adverse side effects (such as toxicity, irritation, and allergic response). Side effects are "undue" when their risk outweighs the benefit provided by the composition. Non-limiting examples of pharmaceutically acceptable carriers include, without limitation, any of the standard pharmaceutical carriers such as phosphate buffered saline solutions, sterile isotonic saline, water, and emulsions such as, for example, oil/water emulsions and microemulsions.

"Pharmaceutically acceptable diluent" means compounds and compositions that are of sufficient purity and quality for use in the formulation of a composition of the invention that, when appropriately administered to an animal or human, do not produce an adverse reaction, and that are used as a diluting agent for a drug substance (i.e. salt forms of a 15-LOX product of the present invention).

Accordingly, in some embodiments the present disclosure provides a method of treating a disease or disorder in subject in need thereof, the method comprising administering to the subject a pharmaceutical composition as disclosed herein. In some embodiments, the disease or disorder is selected from the group consisting of: acne, erythema, infection, fatty liver, neuropathy, and skin inflammation. In some embodiments, the pharmaceutical composition is administered to the subject in an amount sufficient to provide a therapeutically effective amount of the salt form of the 15-lipoxygenase product. In some embodiments, the therapeutically effective amount is about 0.001 mg/kg/day to about 100 mg/kg/day.

In some embodiments, the present disclosure provides a method of making the 15-LOX compound (e.g., 13-HODE, 15-HETrE, or 15-OHEPA). In some embodiments, the method comprises contacting the corresponding 15-LOX precursor compound (e.g., linoleic acid, DGLA or EPA) with lipoxygenase (e.g., a composition comprising lipoxygenase) in the presence of oxygen. In some embodiments, the oxygen is present at a pressure greater than atmospheric pressure (e.g., 2-3 bar), optionally in the presence of a reducing agent (e.g., cysteine) to form the 15-LOX compound. In some embodiments, a salt formation step is carried out comprising mixing a salt formation agent and the 15-LOX compound. In some embodiments the salt forming step is carried out under oxygen-free or substantially oxygen-free conditions. In some embodiments the salt forming step is carried out in the same or different vessel than the step of contacting the 15-LOX precursor compound with lipoxygenase. In some embodiments, the method further comprises filtering the resulting 15-LOX compound salt. In some embodiments, the method does not include chromatographic purification of the 15-LOX compound salt.

In some embodiments, the method comprises contacting DGLA with a stoichiometric excess of lipoxygenase under a blanket of pressurized oxygen (e.g., at about 2 bar, about 2.5 bar or about 3 bar) in the presence of a stoichiometric excess of cysteine at a basic pH (e.g., about 9-10) and stirred until consumption of DGLA is complete. In some embodiments, the method further comprises acidification to about pH 3-4 (e.g., by adding an appropriate amount of solid citric acid) and isolating 15-HETrE free acid contained in the filtrate. In some embodiments, the 15-HETrE free acid isolated from the filtrate is then subjected to a salt formation step, for example by exposure to a salt-forming agent such as L-lysine under oxygen-free or substantially oxygen free conditions in the same or separate vessel. In some embodiments, the resulting salt (e.g. lysine salt) is washed with a solvent (e.g., MtBE) once to about 4 times. In some embodiments, the resulting 15-HETrE lysine salt has a purity of at least 90%, at least about 92.% or at least 95% without the use of a chromatographic purification technique.

EXAMPLES

Example 1: Salts of 15-HETrE

Twenty four co-formers and acids were used to screen for stable forms of 15-HETrE but most yielded oils or gels. Salts with improved handling properties were isolated from the screen: sodium, ornithine, lysine, meglumine and piperazine, but all were poorly crystalline. Four of the five salts are sticky solids but the lysine salt exists as a powder and was chemically stable at ambient temperature under vacuum for 8 days.

TABLE 1

Co-formers/acids used for salt and co-crystal screen of 15-(S)-HETrE

| bases (salt formers) | neutral cocrystal formers | acids with desirable properties (oral & topical) |
|---|---|---|
| arginine | urea | 4-hydroxybenzoic |
| choline | nicotinamide | ascorbic |
| lysine | cysteine | azelaic (nonanedioic) |
| meglumine | allantoin | benzoic |
| ornithine | — | citric |
| tromethamine (TRIS) | — | gallic |
| NaHCO$_3$ | — | glycolic (hydroxyacetic) |
| DABCO[1] | — | malic (L) |
| imidazole[1] | — | succinic (butanedioic) |
| piperazine | — | tartaric (L) |

[1]These co-formers are not pharmaceutically acceptable, but were examined to see if handling could be improved for manufacture.

Example 2: Characterization of 15-HETrE Oil

Figure 2:
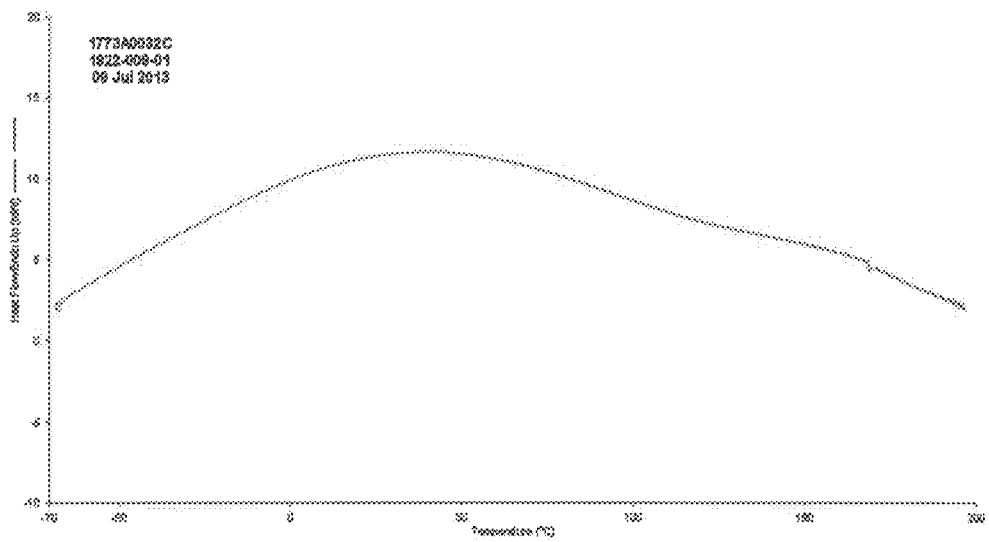
FIG. 2 shows the differential scanning calorimetry (DSC) thermogram of 15-HETrE from −70° C. to 200° C. at a rate of 10° C./min.
Figure 3:
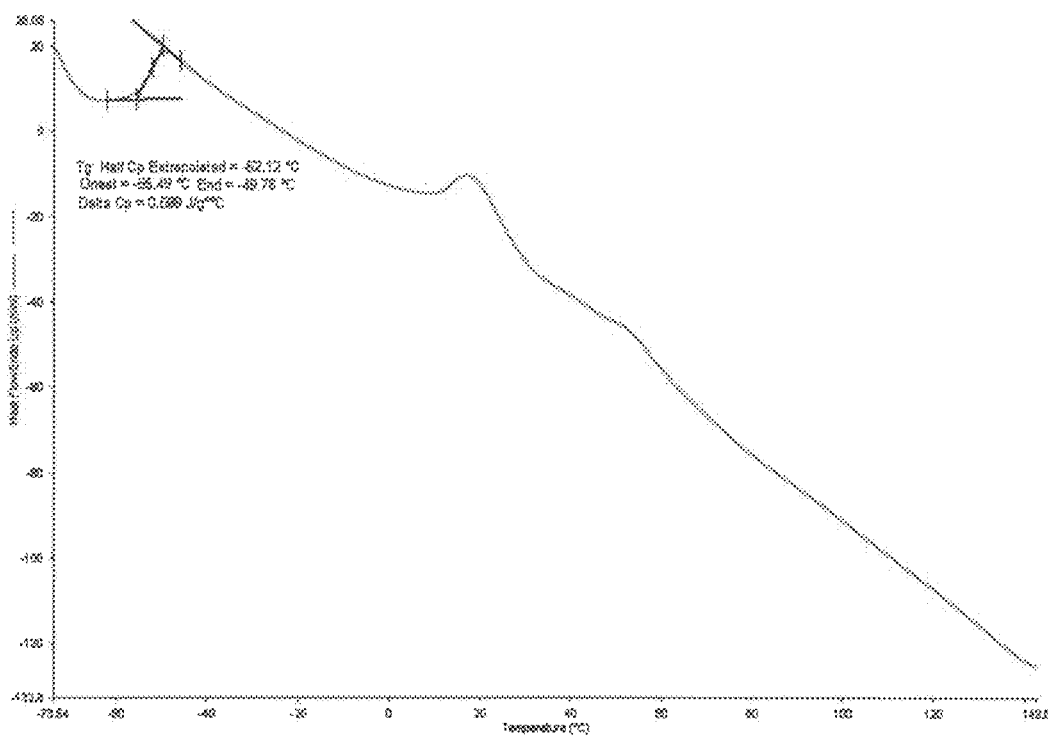
FIG. 3 shows the hyper-differential scanning calorimetry (Hyper DSC) thermogram of 15-HETrE from −75° C. to 150° C. at a rate of 200° C./min.
Figure 4:
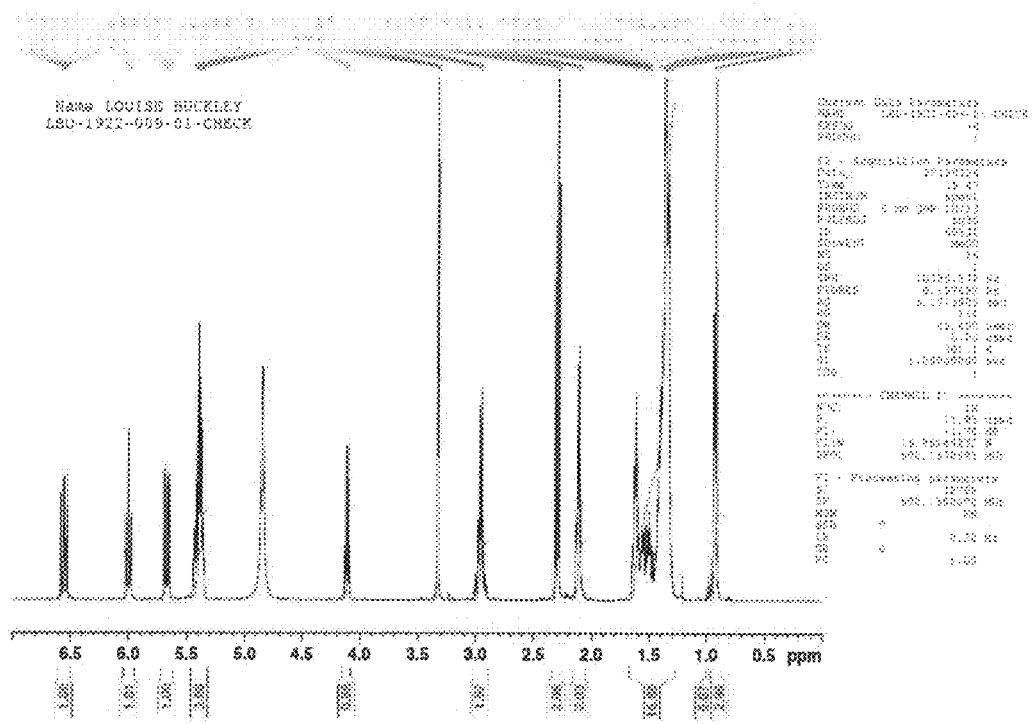
FIG. 4 shows the proton-NMR spectrum of HETrE in $d_4$-methanol at 500 MHz.
Figure 5:
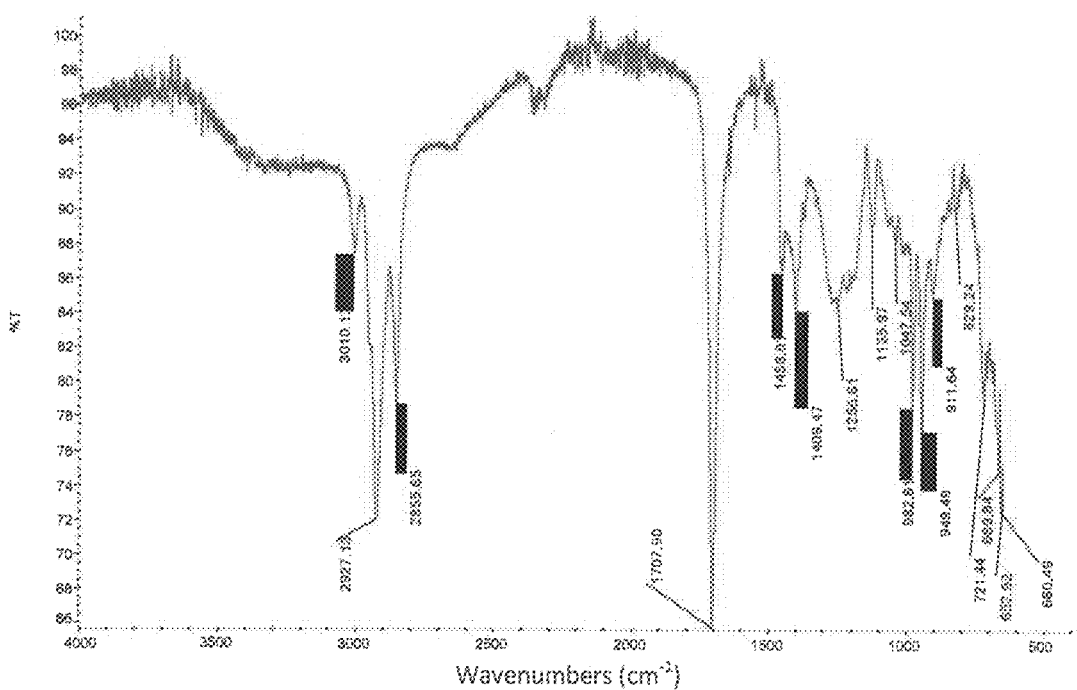
FIG. 5 shows the FT-IR spectrum of 15-HETrE.

15-HETrE was viscous oil and was confirmed by XRPD analysis to be X-ray amorphous (FIG. 1). No thermal events were observed during differential scanning calorimetry (DSC) analysis of the material (FIG. 2). A possible glass transition (Tg) of 15-HETrE was noted by hyper DSC analysis at −52° C. Further thermal events were noted at higher temperature but their causes are unknown without further analysis (FIG. 3). $^1$H-NMR spectroscopy of the material showed that it was concordant with molecular structure (FIG. 4). The FT-IR spectrum of 15-HETrE is displayed in FIG. 5. The carbonyl stretch of the free acid is visible at 1707 cm$^{-1}$.

Example 3: Solubility Screen of as-Received 15-HETrE

The solubility of 15-HETrE was estimated in ten solvents using the aliquot addition method. 15-HETrE was found to be miscible in all solvents tested, displaying high solubility in all cases. However, when combined with 1,1,1,3,3,3-hexafluoroisopropyl acrylate ("HFIPA"), rapid color change from clear, colorless to blood red to deep purple/black was observed. This is believed to be due to degradation of 15-HETrE, therefore HFIPA was not used in any further studies of 15-HETrE. The solubility data are shown in Table 2 below.

TABLE 2

Estimated solubilities of 15-HETrE in a range of solvents.

| Solvent | Abbreviation | Solubility Range mg/dl |
|---|---|---|
| Acetonitrile | ACN | 93-278 |
| THF | — | 332-996 |
| Acetone | — | 312-936 |
| Dioxane | — | 166-498 |
| DCM | — | 117-352 |
| Ethyl acetate | EtOAc | 189-566 |
| DMF | — | 123-368 |

TABLE 2-continued

Estimated solubilities of 15-HETrE in a range of solvents.

| Solvent | Abbreviation | Solubility Range mg/dl |
|---|---|---|
| Ethanol | EtOH | 126-378 |
| Methanol | MeOH | 212-636 |

The experiments yielded gels or oils. Analysis of these materials by XRPD has shown them to be composed of X-ray amorphous materials or X-ray amorphous material and co-former. Four co-formers provided materials that were solid or semi-solid and possess improved handling properties over the starting material: NaHCO$_3$, ornithine, lysine and piperazine.

Example 4: 15-HETrE Sodium Salt

Material prepared according to Example 1 using NaHCO$_3$ and 15-HETrE was isolated as an off white waxy solid after evaporation of the ethanol/water co-solvent system. Dissolution in ethanol followed by evaporation improved the handleability of the material. Disordered material was also isolated by slurrying with MTBE.

Figure 6:
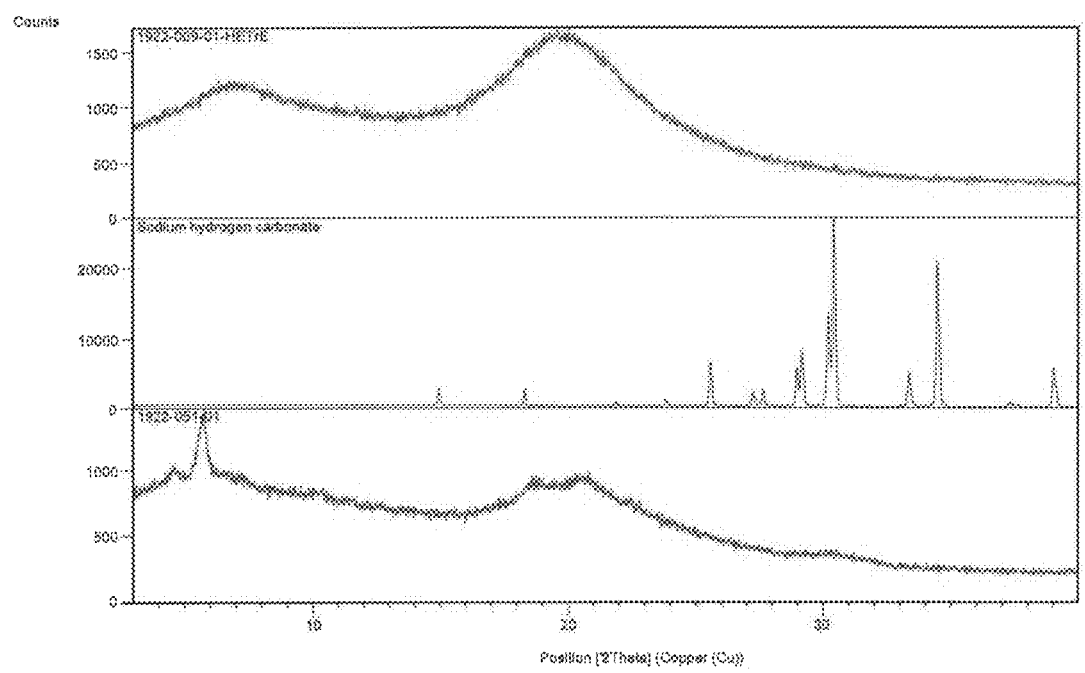
FIG. 6 shows a comparison of the X-ray powder diffraction patterns of 15-HETrE in free acid form (top panel) with sodium hydrogen carbonate (middle panel) and 15-HETrE sodium salt (bottom panel).

The material was found to be composed of very disordered crystalline material when analyzed by XRPD (FIG. 6). Some amorphous content may also be present.

Figure 7:
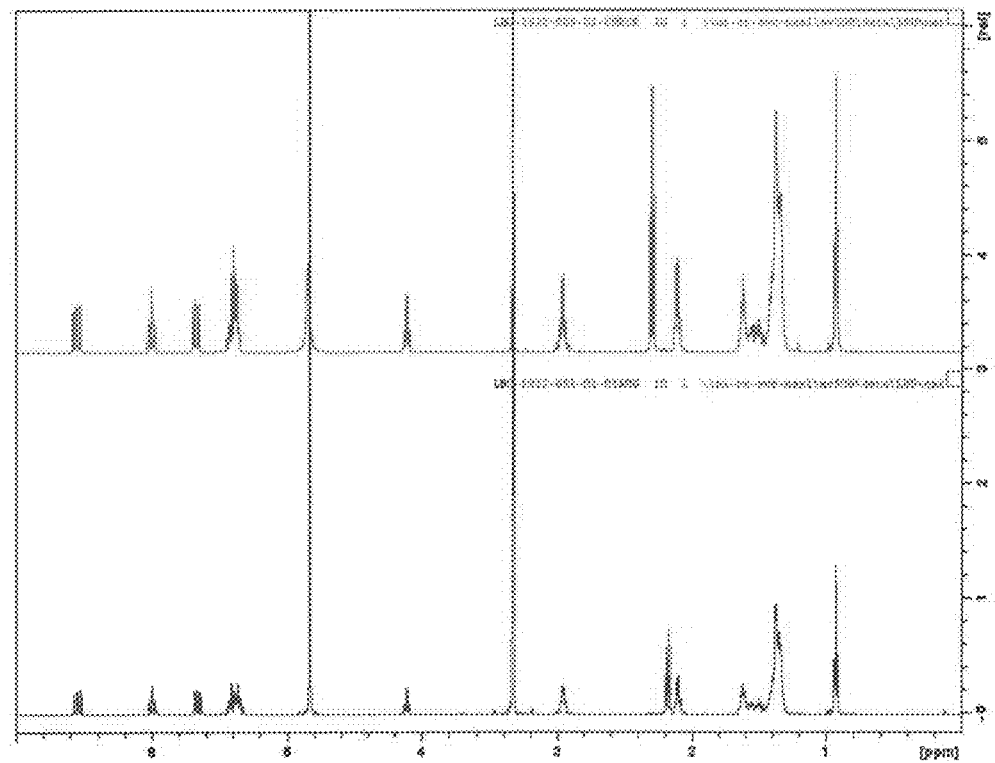
FIG. 7 shows a comparison of the proton NMR spectra of 15-HETrE in free acid form (top spectrum) and 15-HETrE sodium salt (bottom spectrum).

Peak shifting observed in the $^1$H-NMR spectrum of the material suggested sodium salt formation (FIG. 7).

Figure 8:
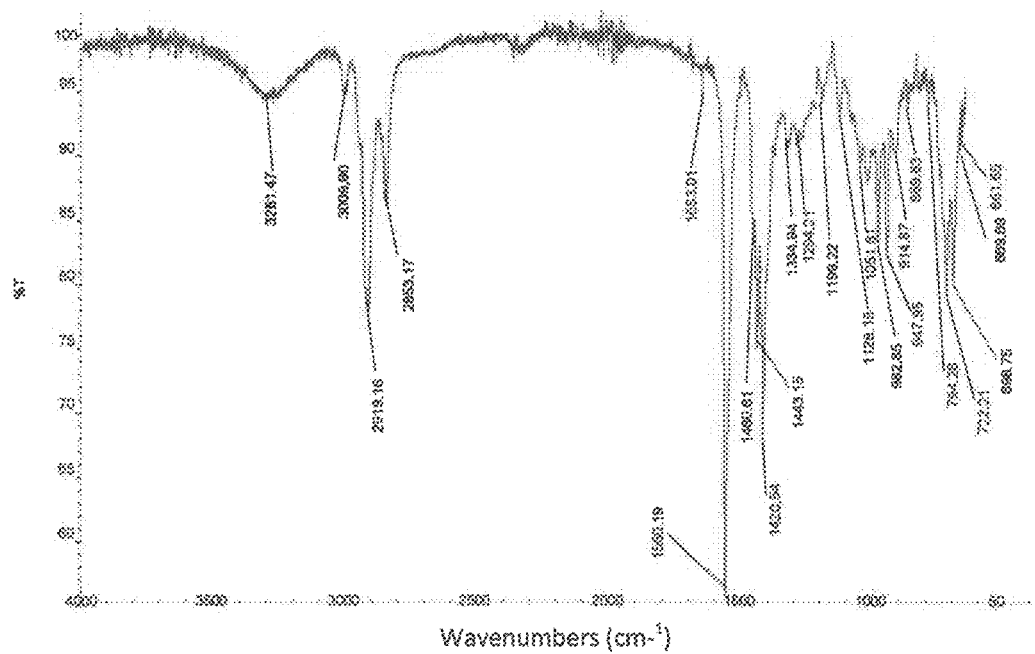
FIG. 8 shows the FT-IR spectrum of 15-HETrE sodium salt.

FT-IR analysis of a sample of the sodium salt did not show the carbonyl stretch present in the free acid at 1707 cm$^{-1}$, suggesting salt formation (FIG. 8).

Figure 9:
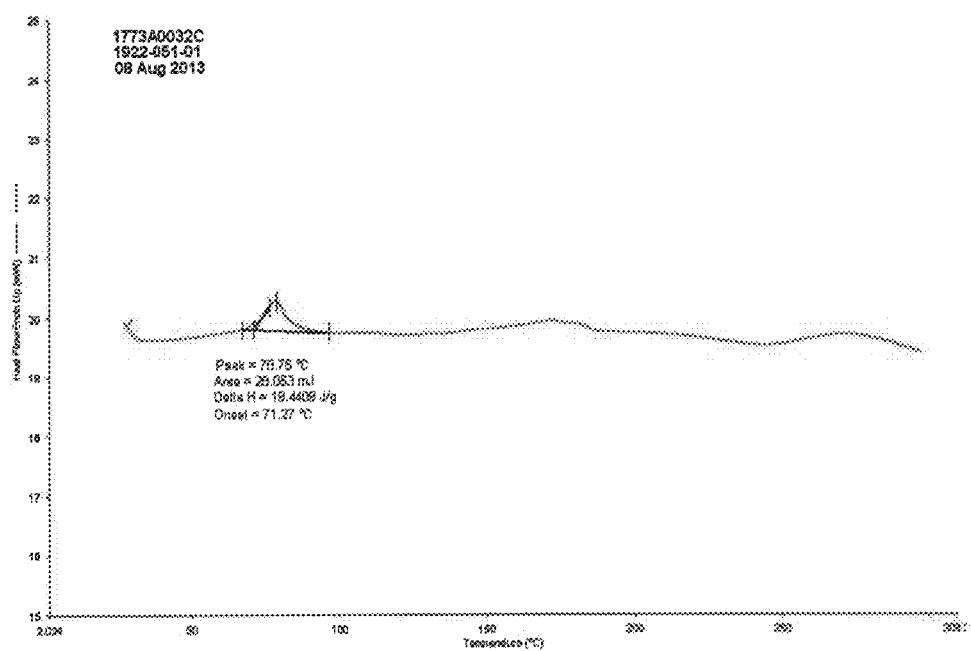
FIG. 9 shows the differential scanning calorimetry (DSC) thermogram of 15-HETrE sodium salt.

DSC analysis of the 15-HETrE sodium salt showed a small endotherm with an onset temperature of 71.3° C. (FIG. 9). This endotherm was not observed during the thermal analysis of the free acid (see, e.g., FIGS. 2-3).

Example 5: 15-HETrE Lysine Salt

Material prepared according to Example 1 using lysine and 15-HETrE The material was isolated as an off white powdery solid from the evaporation of the ethanol/water co-solvent system. Dissolution in ethanol followed by evaporation improved the handleability of the material.

Figure 10:
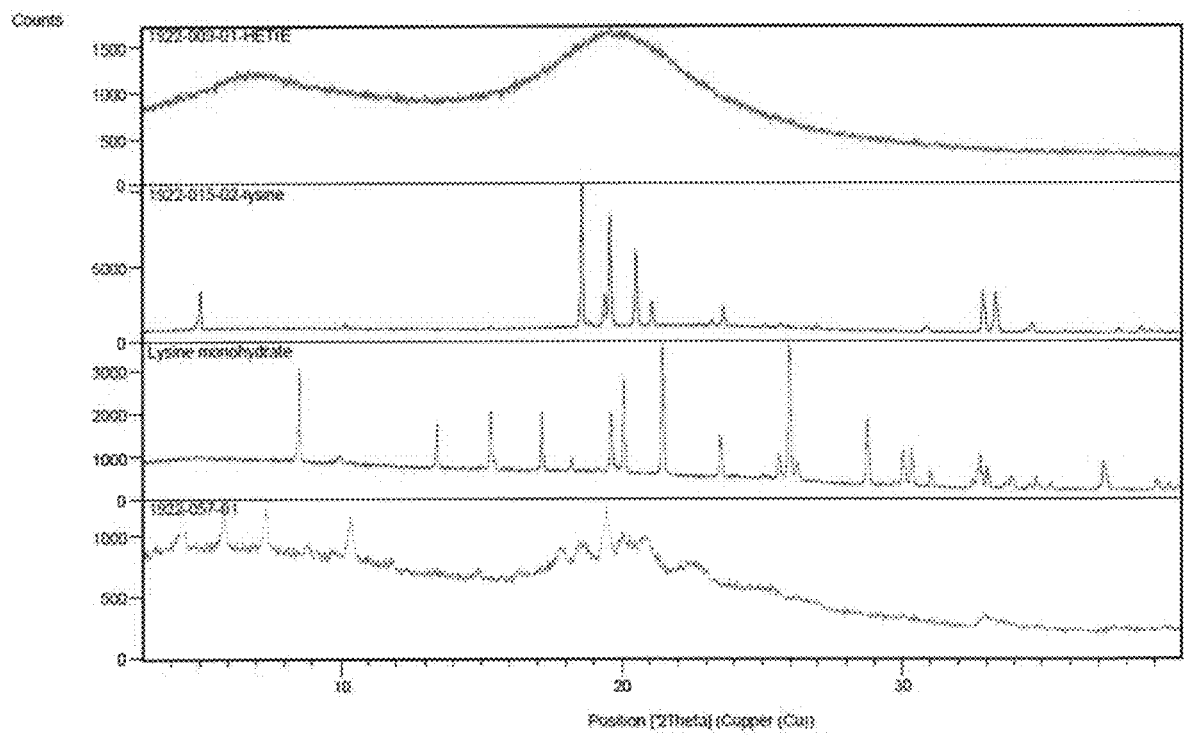
FIG. 10 shows a comparison of the X-ray powder diffraction patterns of 15-HETrE free acid (top panel), lysine prepared by salt cracking (second panel down), lysine monohydrate (third panel down), and 15-HETrE lysine salt (bottom panel).

The material was composed of disordered crystalline material when analyzed by XRPD (FIG. 10). Equally spaced diffraction peaks at low angle suggest the formation of a mesophase such as a liquid crystal.

The same XRPD pattern was observed from a number of experiments including evaporation, grinding and sonication (neat and with solvent).

Figure 11:
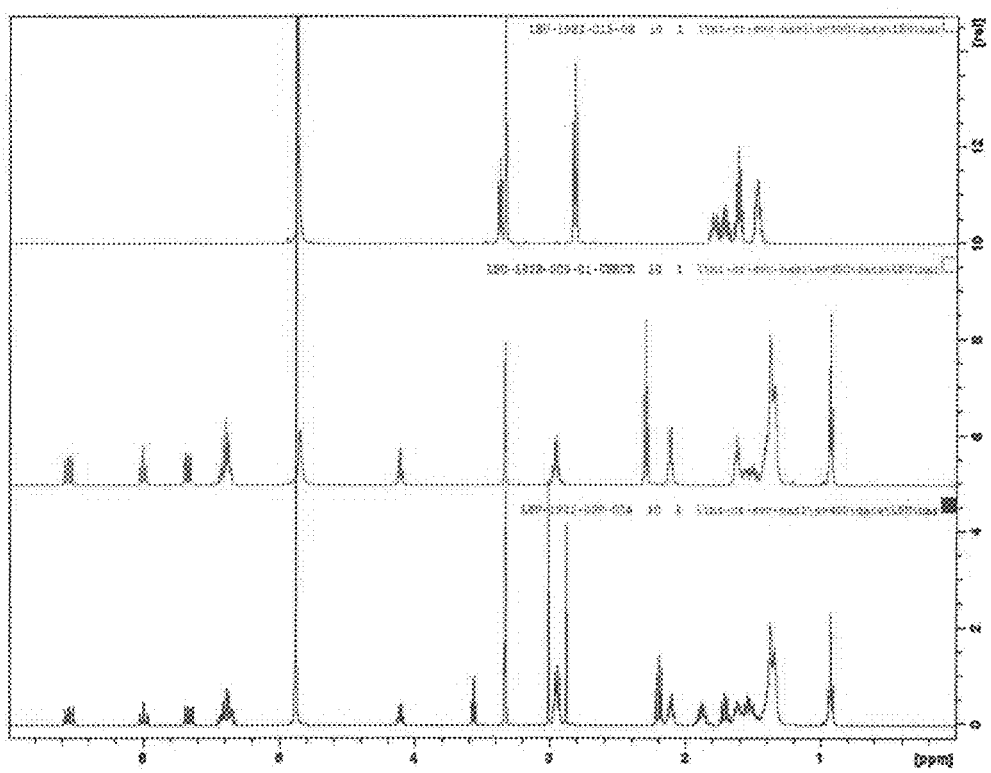
FIG. 11 shows a comparison of the proton NMR spectra for lysine (top spectrum), 15-HETrE free acid (middle spectrum) and 15-HETrE lysine salt (bottom spectrum).

Peak shifting of 15-HETrE and lysine observed in the $^1$H-NMR spectrum of the material indicated possible salt formation (FIG. 11). The ratio of 15-HETrE:lysine was 0.9:1.

Figure 12:
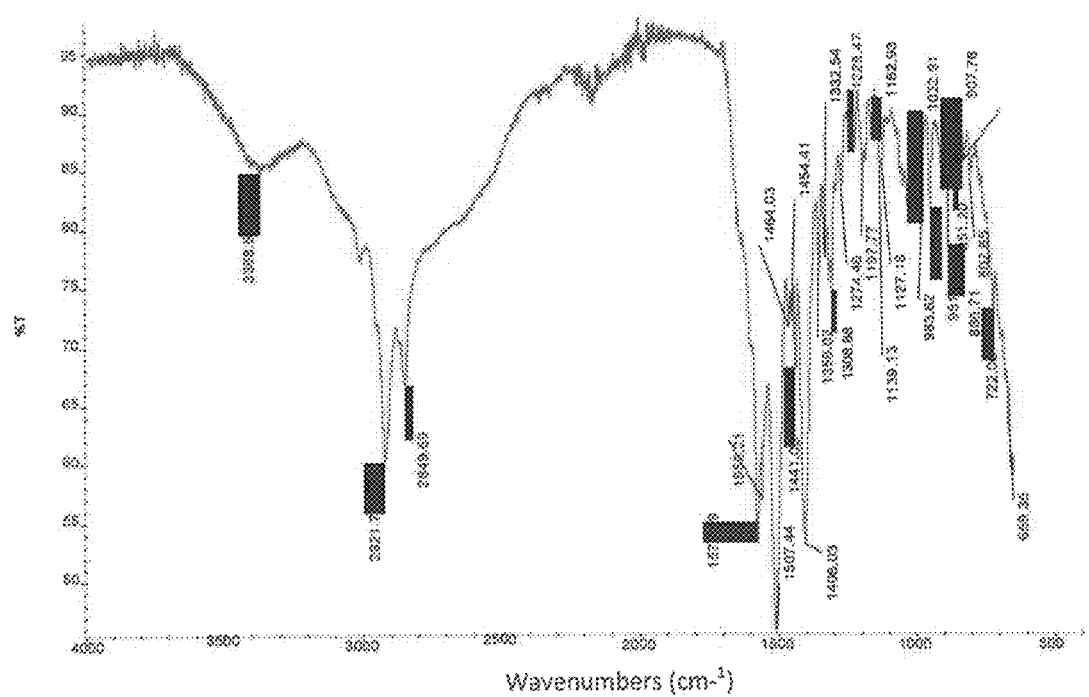
FIG. 12 shows the FT-IR spectrum of 15-HETrE lysine salt.

FT-IR analysis of a sample of the lysine salt shows that the strong carbonyl stretch, present in the free acid at 1707 cm$^{-1}$, had vanished suggesting salt formation (FIG. 12).

Figure 13:
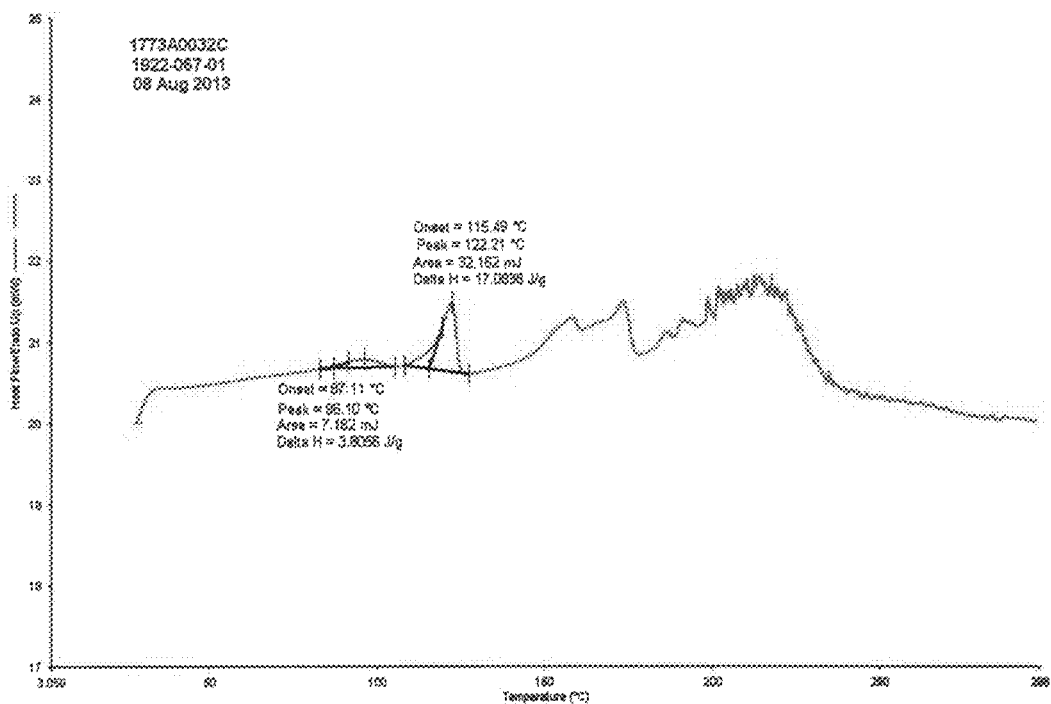
FIG. 13 shows the differential scanning calorimetry (DSC) thermogram of 15-HETrE lysine salt.

DSC analysis of the 15-HETrE lysine salt showed two small endotherms with onset temperatures of 87.1° C. and 115.5° C. respectively (FIG. 13). These endotherms were not observed during the thermal analysis of the free acid (see, e.g., FIGS. 2-3).

Example 6: 15-HETrE Ornithine Salt

Figure 14:
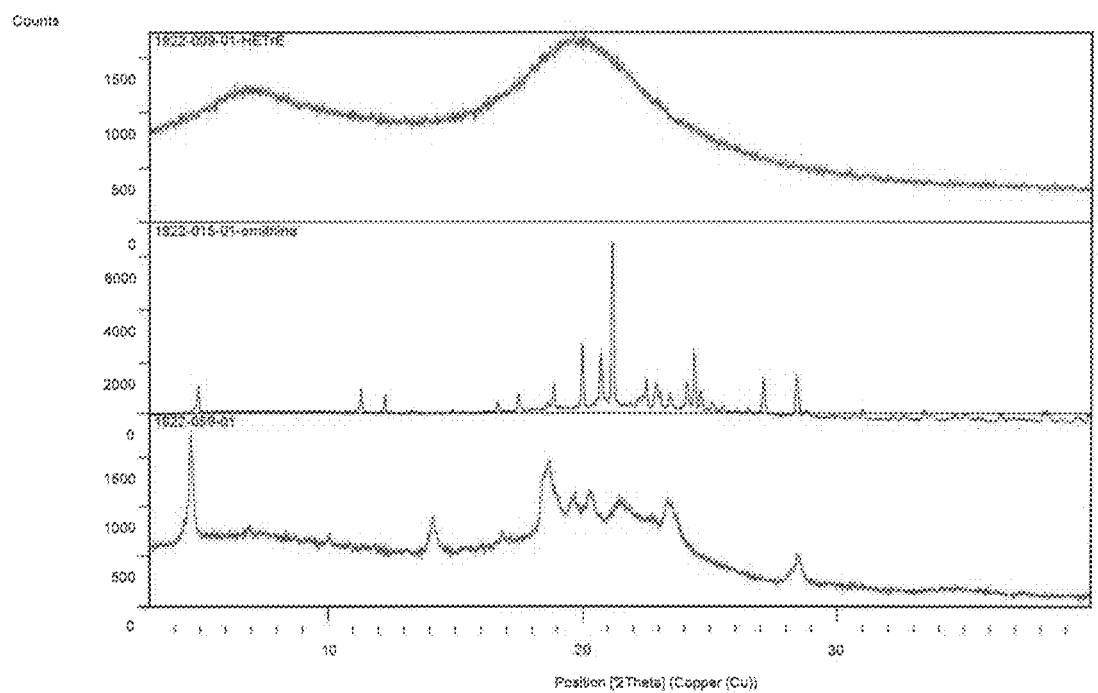
FIG. 14 shows a comparison of the X-ray powder diffraction patterns of 15-HETrE free acid (top panel), ornithine prepared by salt cracking (middle panel), and 15-HETrE ornithine salt (bottom panel).

Material prepared according to Example 1 using ornithine and 15-HETrE was isolated as an off white waxy/oily solid after evaporation of the ethanol/water co-solvent system. Dissolution in ethanol followed by evaporation improved the handleability of the material. The material was composed of very disordered crystalline material when analyzed by XRPD, and may contain some amorphous content (FIG. 14).

The same XRPD pattern was observed from a number of experiments including evaporation, grinding, precipitation and sonication (neat and with solvent).

Figure 15:
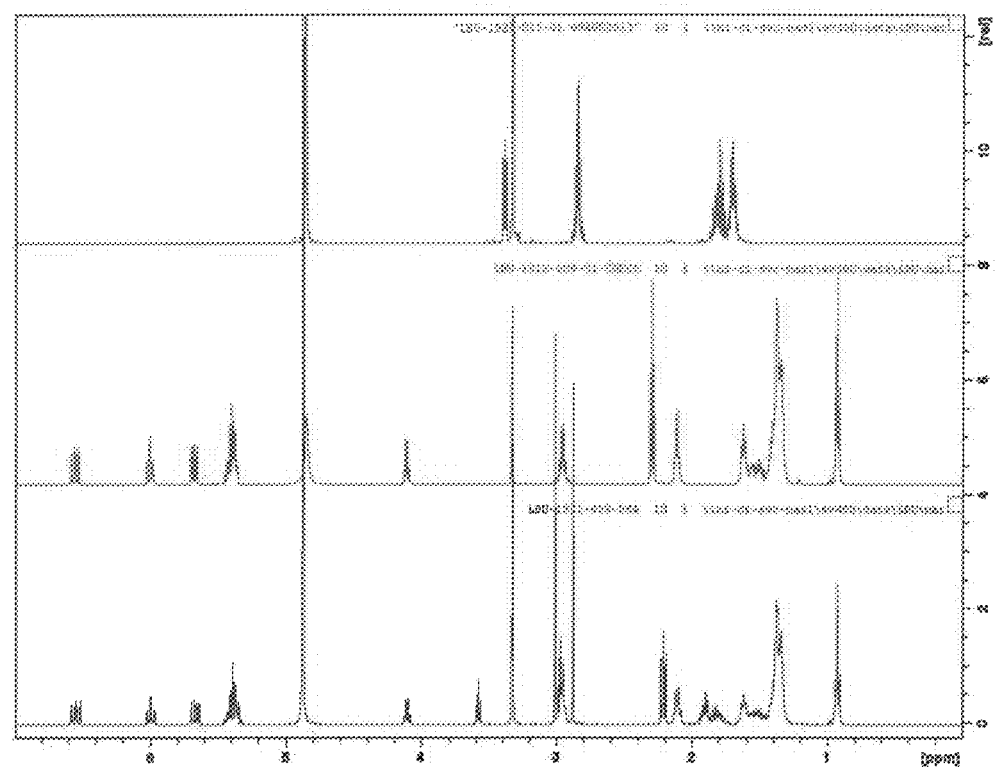
FIG. 15 shows a comparison of the proton NMR spectra for ornithine (top spectrum), 15-HETrE free acid (middle spectrum) and 15-HETrE ornithine salt (bottom spectrum).

Peak shifting of both 15-HETrE and ornithine was observed in the 1H-NMR spectrum indicating probable salt formation (FIG. 15). The ratio of HETrE:ornithine was measured as 1:0.8.

Figure 16:
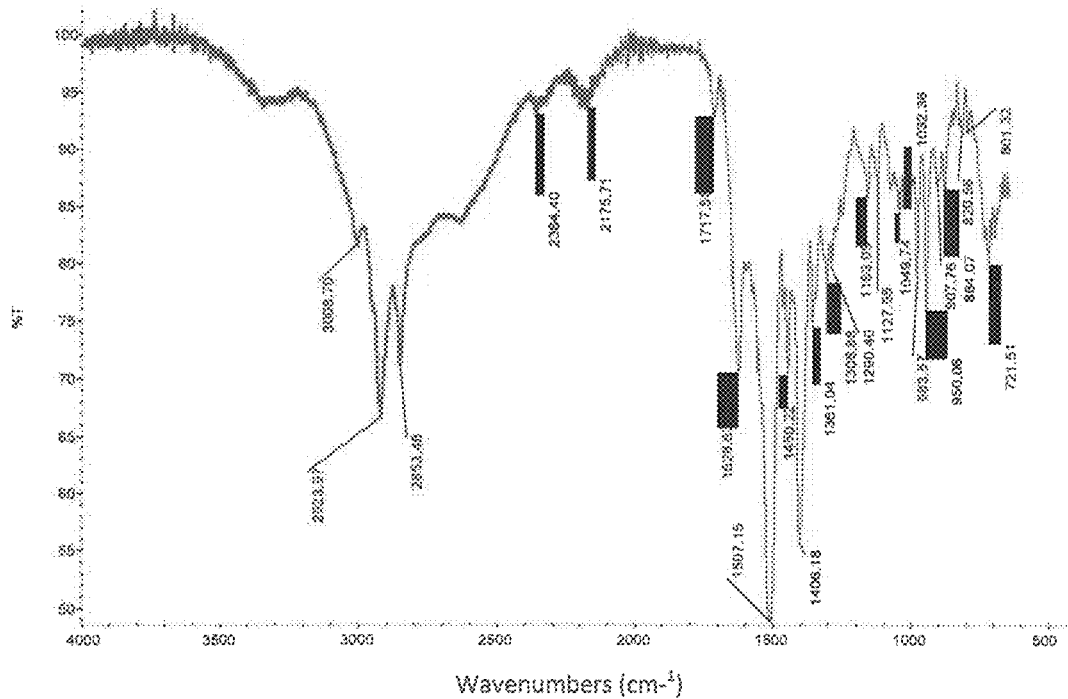
FIG. 16 shows the FT-IR spectrum of 15-HETrE ornithine salt.

FT-IR analysis of a sample of the ornithine salt shows that the strong carbonyl stretch, present in the free acid at 1707 cm$^{-1}$, had vanished suggesting salt formation (FIG. 16).

Figure 17:
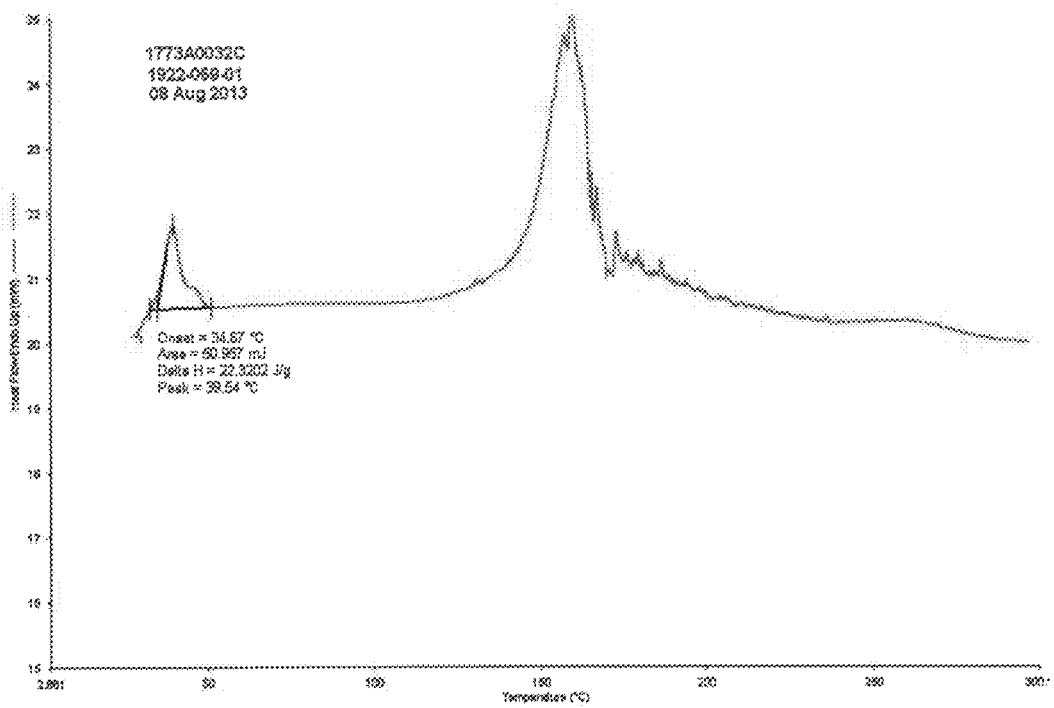
FIG. 17 shows the differential scanning calorimetry (DSC) thermogram of 15-HETrE ornithine salt from 30° C. to 300° C. at a rate of 10° C./min.

DSC analysis of the 15-HETrE lysine salt showed two endotherms with onset temperatures of 34.7° C. and ~120° C. respectively (FIG. 17). The first endotherm may be due to the melt of the material while the second larger endotherm may be due to decomposition of the material. These endotherms were not observed during the thermal analysis of the free acid (see, e.g, FIGS. 2-3).

Example 7: HETrE Piperazine Salt

Yellow, semi-solid material was isolated from the sonication of neat piperazine and 15-HETrE, followed by evaporation of the 1:1 isobutyl acetate and ethanol co-solvent system.

Figure 18:
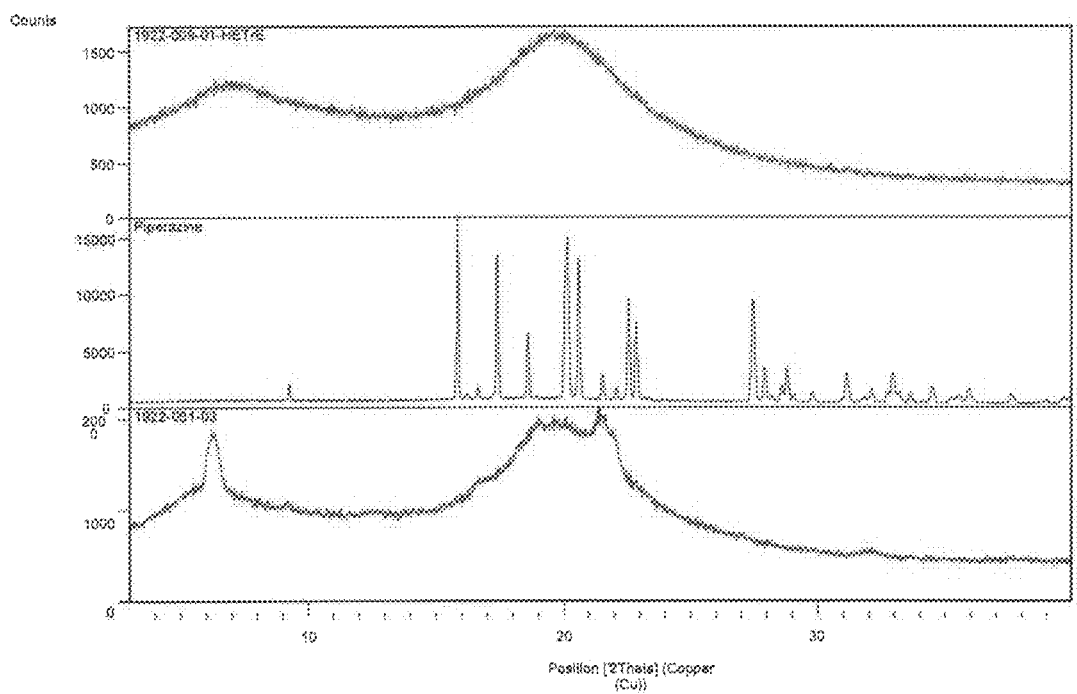
FIG. 18 shows a comparison of the X-ray powder diffraction patterns of 15-HETrE free acid (top panel), piperazine (middle panel), and 15-HETrE piperazine salt (bottom panel).

XRPD analysis showed that the salt was composed of very disordered crystalline material (FIG. 18). Some amorphous content may also be present.

Figure 19:
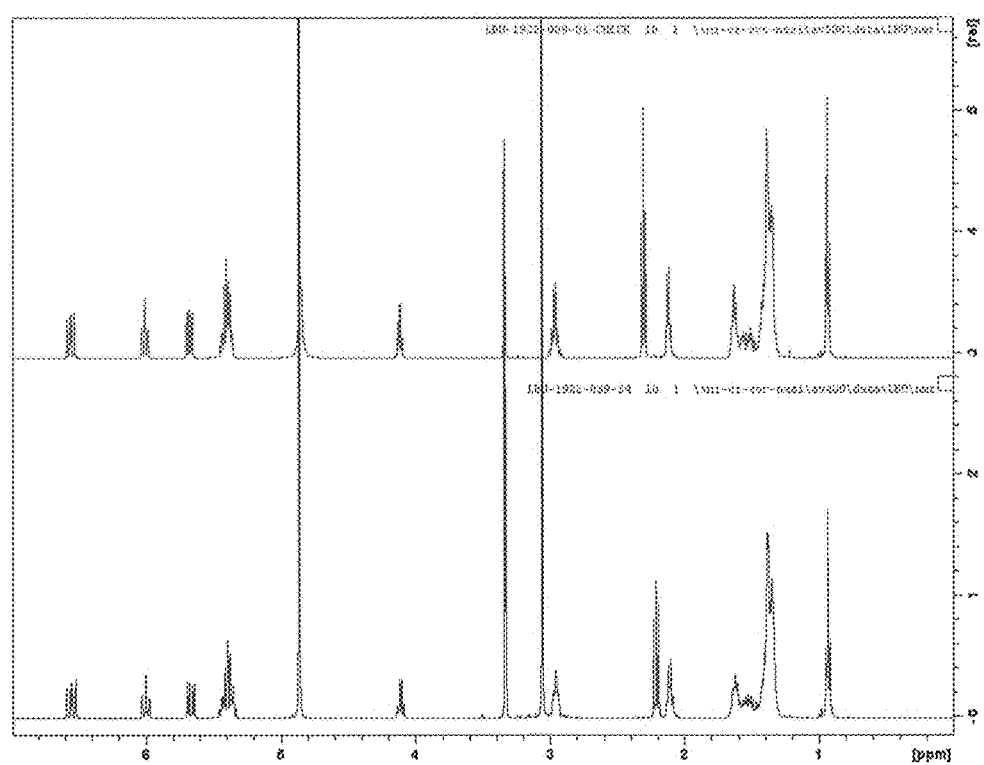
FIG. 19 shows a comparison of the proton NMR spectra for 15-HETrE free acid (top spectrum) and 15-HETrE piperazine salt (bottom spectrum).
Figure 20A:
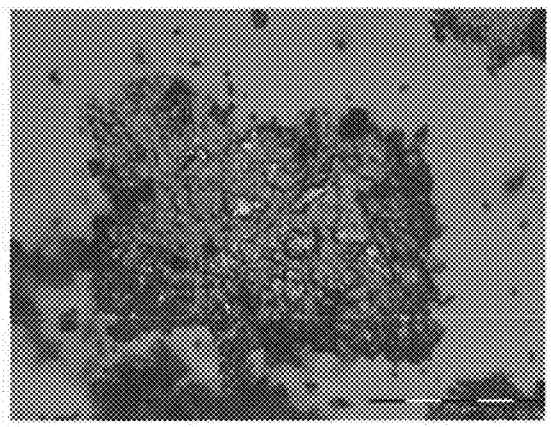
FIGS. 20A-H show 10× magnified images of 15-HETrE lysine salt with first order red plate (FIG. 20A) and with crossed-polarized light (FIG. 20B). 15-HETrE sodium salt with first order red plate (FIG. 20C) and with crossed-polarized light (FIG. 20D). 15-HETrE ornithine salt with first order red plate (FIG. 20E) and with crossed-polarized light (FIG. 20F). and 15-HETrE piperazine salt with first order red plate (FIG. 20G) and with crossed-polarized light (FIG. 20H).
Figure 20B:
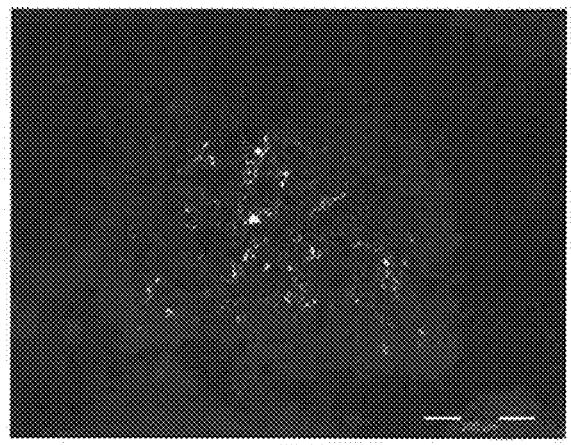
Figure 20C:
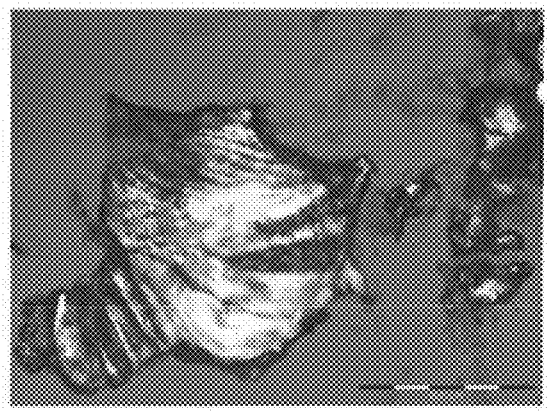
Figure 20D:
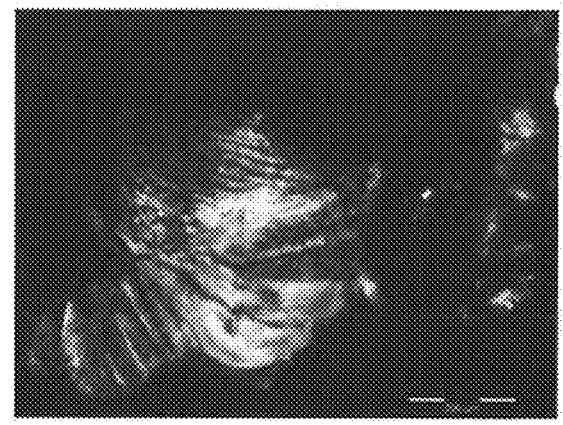
Figure 20E:
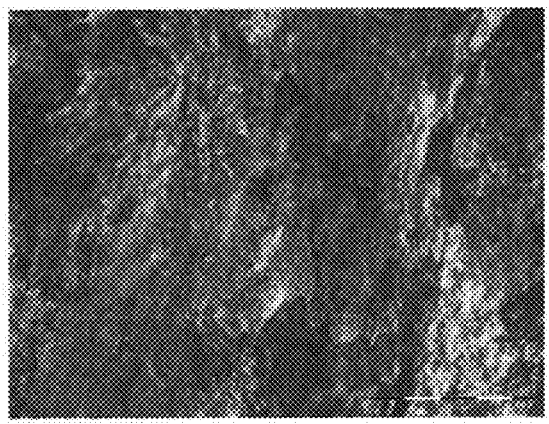
Figure 20F:
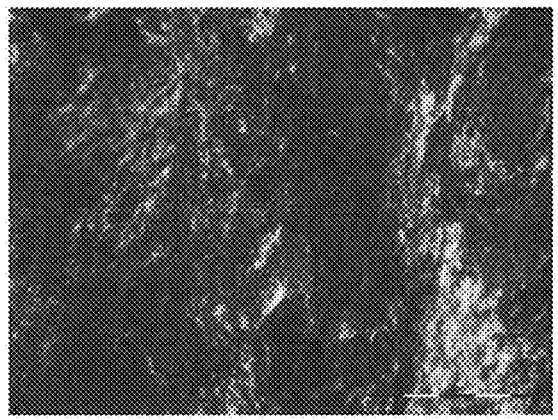
Figure 20G:
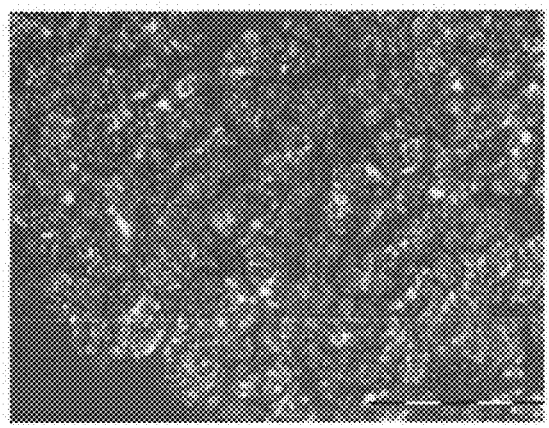
Figure 20H:
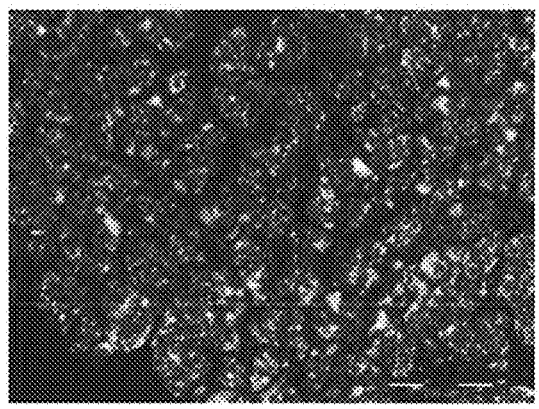

Peak shifting was observed in the $^1$H-NMR spectrum of the suspected salt suggesting salt formation (FIG. 19). The ratio of 15-HETrE:piperazine was 1:0.66.

Example 8: Properties of Sodium, Lysine, Ornithine and Piperazine Salts of 15-HETrE Properties of 15-HETrE salts prepared according to Examples 4-7 were compared against each other and against 15-HETrE free acid API. The sodium, ornithine and piperazine salts were each sticky or waxy solids, but the lysine salt could be made as a powder and was chemically stable at ambient temperature under vacuum for 8 days.

Table 3 compares the properties of each salt that were evaluated during the screen and includes crystallinity, appearance, solvent content by NMR, chemical stability, preparation method and stoichiometry by NMR analysis.

The lysine salt represents the best candidate for development as it could be prepared as a handleable powder and was made by a variety of methods. Salt formation was confirmed by $^1$H-NMR and FT-IR spectroscopy and the salt exhibited an equimolar stoichiometry.

TABLE 3

Table of properties of solids isolated from the salt/cocrystal screen

| Compound | Crystallinity | Appearance | Solvent Content | 8 Day Stability 40/75% RH | Prep method | Stoichiometry (base:API) |
|---|---|---|---|---|---|---|
| HETrE lysine salt | Very disordered | Off white powder | Trace THF or EtOH | 97% purity | Evaporation, slurry, sonication | 1:1 |
| HETrE sodium salt | Very disordered | Off white waxy solid | trace EtOH | 95% purity | Evaporation or slurry | Cannot be determined by NMR |
| HETrE ornithine salt | Very disordered | Off white waxy solid, yellow coloration on storage | Trace THF or EtOH | 96% purity | Evaporation, slurry, sonication | 0.9:1 |
| HETrE piperazine salt | Very disordered | Yellow sticky semi-solid | Trace EtOH | Not tested | Evaporation or sonication | 0.7:1 |
| HETrE API | amorphous | oil | — | — | — | — |

The sodium salt was used for further study as a backup candidate as it was a waxy solid and was made by a number of different methods. Stoichiometry could not be determined by NMR spectroscopy.

The ornithine salt was not recommended for further study as it was quite sticky and displayed a yellow coloration over time. The piperazine salt exhibited the poorest handling properties and was a sticky, semi-solid material that appears to flow on exposure to air at ambient temperature, probably due to uptake of moisture.

Photomicroscopic images of each salt are displayed in FIGS. 20A-H. Images of each salt were captured under crossed-polarized light with and without a 1st order red filter, which enhances contrast between crystalline and amorphous content. The length of the scale bar represents 200 μm. The bright colors are evidence of crystallinity.

Example 9: 15-HETrE Lysine Salt Scale Up

A slurry method was found as an alternative to the previously used rotary evaporation method to prepare the lysine salt using EtOAc as solvent, but failed to generate the salt when scaled up. Addition of 9% MeOH to EtOAc generated the salt on a 800 mg scale, with a purity of 96%. Stability studies have commenced for the lysine salt (20° C./60% RH air/N$_2$ and 40° C./75% RH air/N$_2$, open/closed vials).

An alternative method to prepare 15-HETrE sodium salt by slurrying and avoid need for rotary evaporation could not be found. If water was used, the base dissolved but the resulting salt was also highly soluble and thus did not precipitate. If water was excluded, base did not dissolve and therefore did not react with 15-HETrE. Scale up and characterization was completed for 15-HETrE sodium salt using rotary evaporation from 10% aqueous EtOH, then EtOH. The recovered material had a yellow coloration. Purity as measured by UPLC analysis was ~81%.

Example 10: Characterization of the Scaled Up 15-HETrE-Lysine Salt

Figure 21:
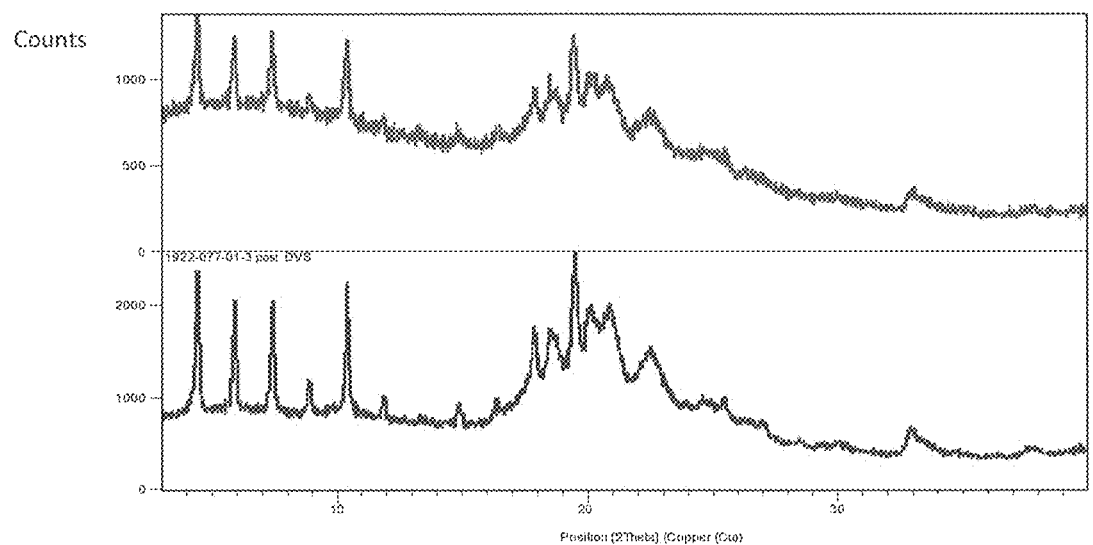
FIG. 21 shows a comparison of X-ray powder diffraction patterns for 15-HETrE lysine salt before (top panel) and after (bottom panel) dynamic vapor sorption (DVS) analysis.

15-HETrE-Lysine salt prepared according to Example 9 was analyzed by XRPD and found to consist of disordered crystalline material (FIG. 21).

Figure 22:
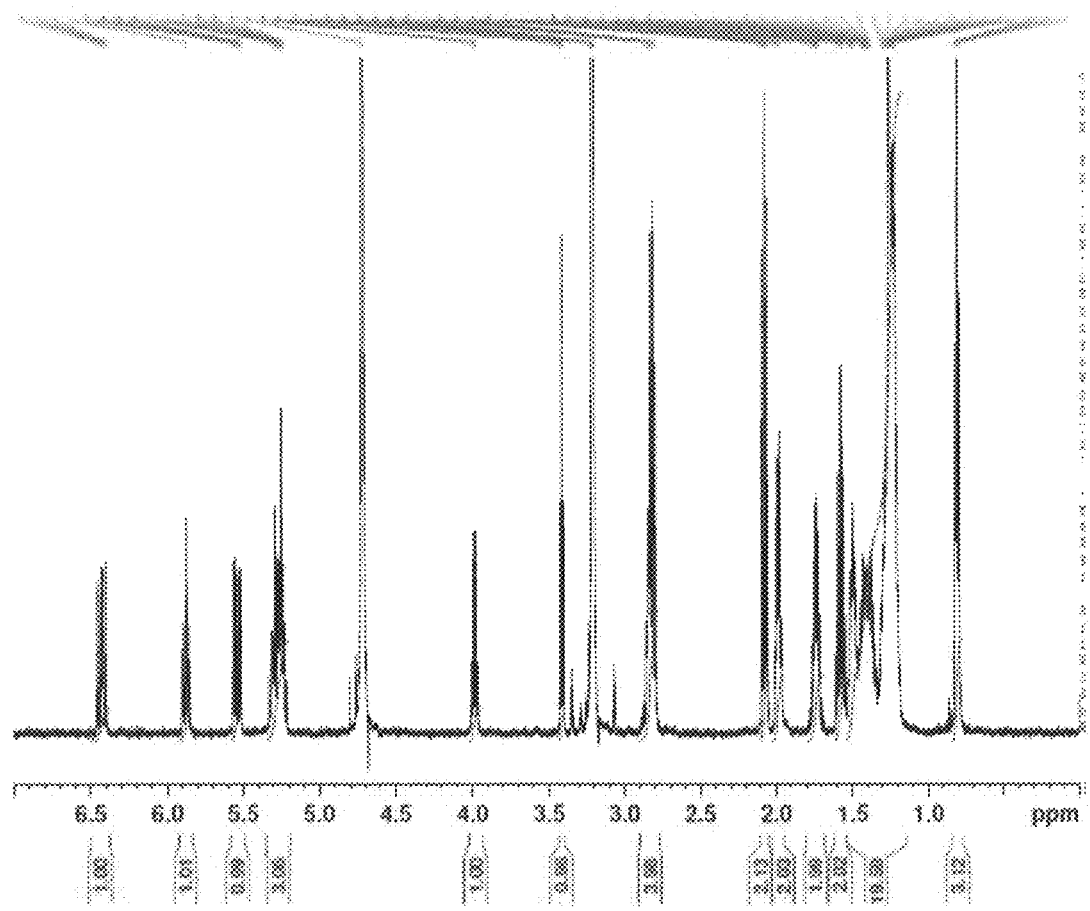
FIG. 22 shows the proton NMR spectrum of 15-HETrE lysine salt in $d_4$-methanol.

Salt formation was confirmed by $^1$H-NMR spectroscopy (solvent: $d_4$-MeOD), as evidenced by peak shifting of both lysine and 14-HETrE protons (FIG. 22). The ratio of HETrE: lysine was measured as 1:1.

Figure 23:
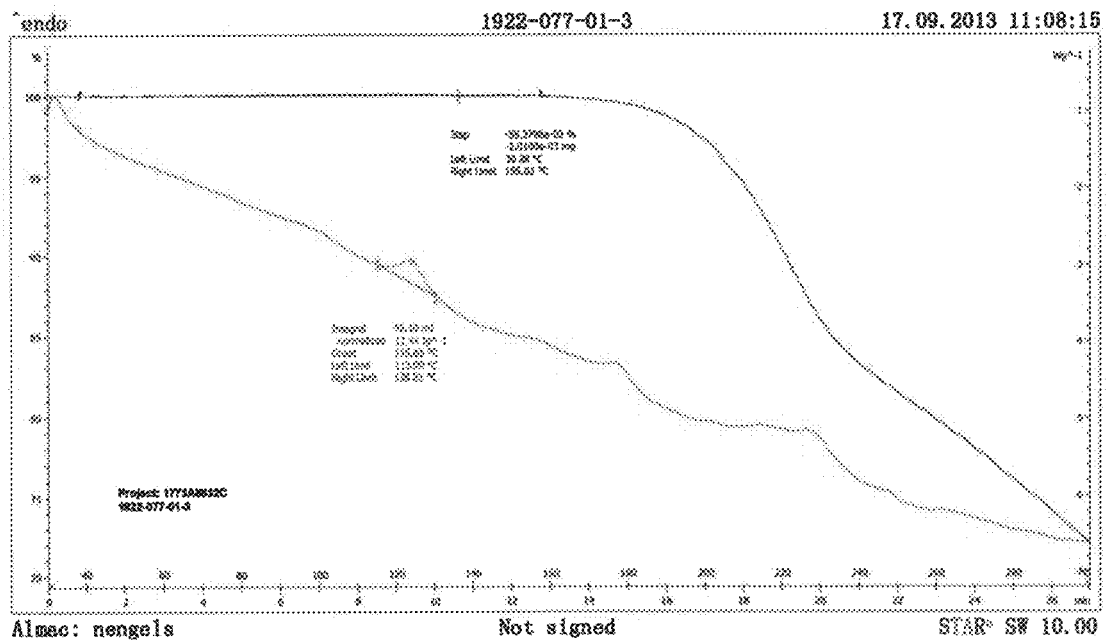
FIG. 23 shows a thermogravimetric/differential thermal analysis ("TG/DTA") thermogram of 15-HETrE lysine salt.

TG/DTA analysis of the 15-HETrE-Lysine salt exhibited negligible weight loss <160° C. indicating that the salt was anhydrous. A small endotherm at 116° C. (onset) was noted but the cause is unknown (FIG. 23).

Figure 24:
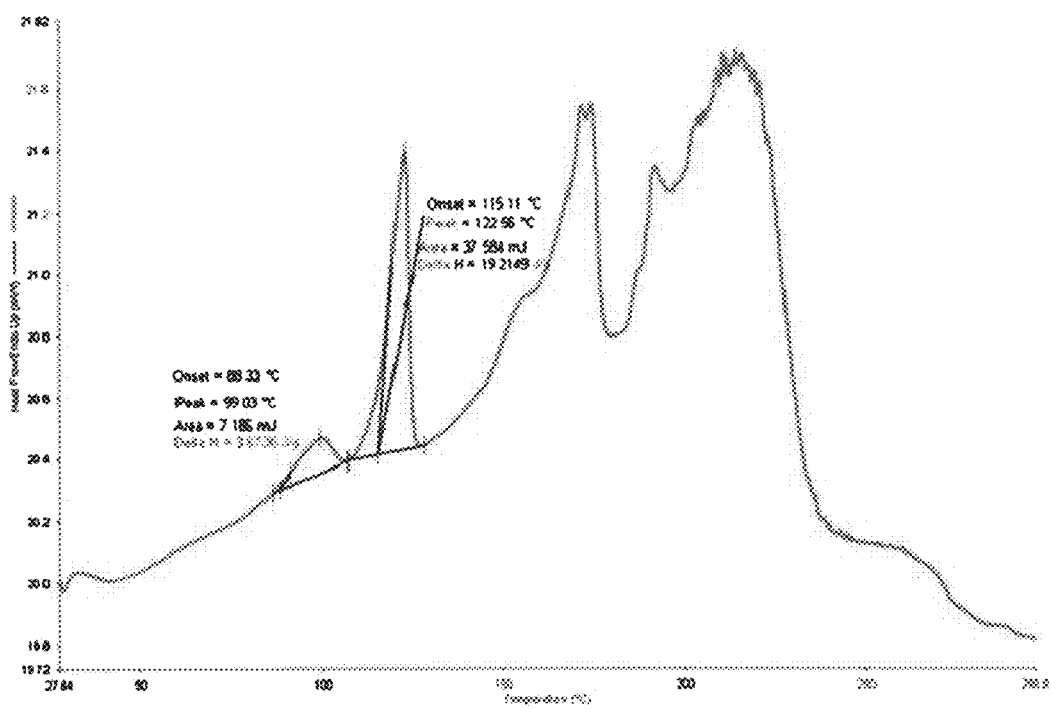
FIG. 24 shows the differential scanning calorimetry (DSC) thermogram of 15-HETrE lysine salt from 30° C. to 300° C. at a rate of 10° C./min.
Figures 25A, 25B, 25C, 25D:
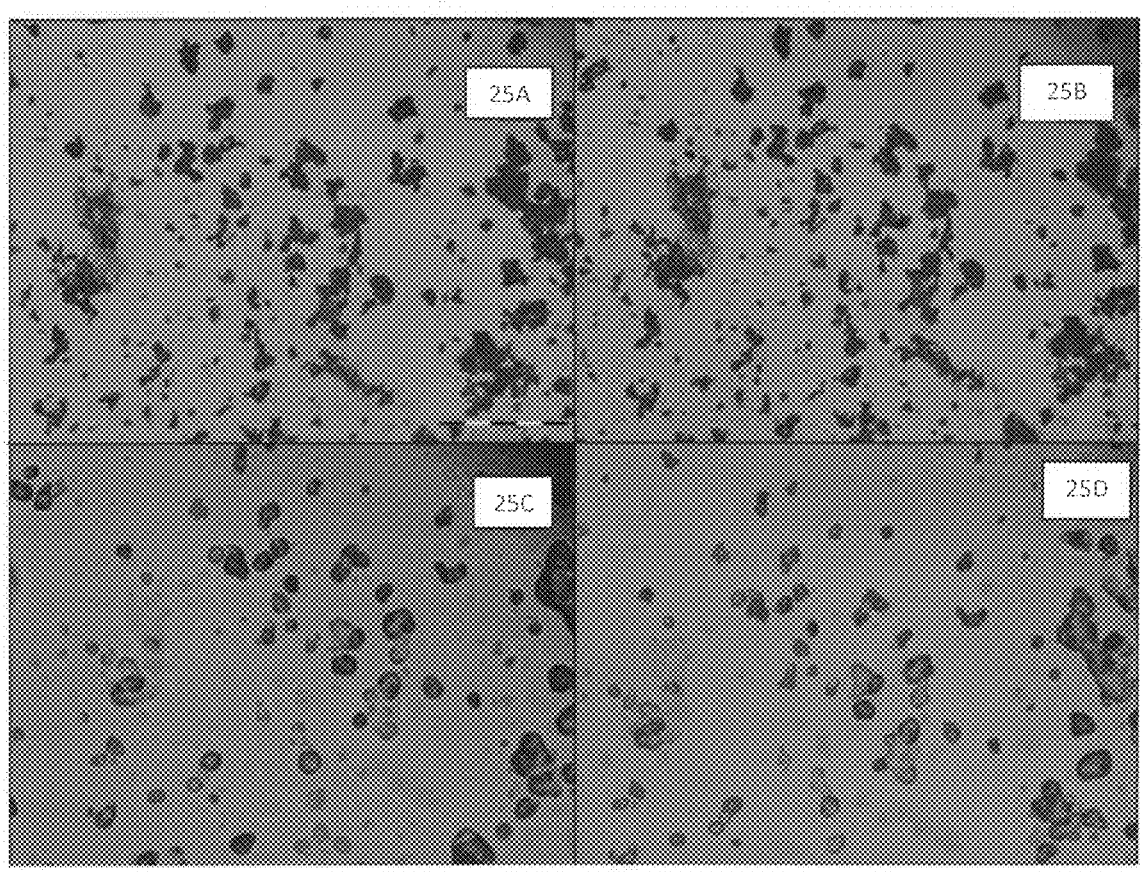
FIG. 25A shows hotstage microscopy images of 15-HETrE lysine salt at 30° C.
FIG. 25B shows hotstage microscopy images of 15-HETrE lysine salt at 120° C.
FIG. 25C shows hotstage microscopy images of 15-HETrE lysine salt at 200° C.
FIG. 25D shows hotstage microscopy images of 15-HETrE lysine salt at ambient temperature after melt.

The DSC thermogram displayed a number of small endotherms with onsets at 88° C. and 115° C., followed by broader endotherms, which may be associated with melt and decomposition events (FIG. 24).

Hot stage microscopy of the salt between 30° C. and 200° C. showed no observable melt until approximately 140° C., but the material had not completely melted at 200° C. (FIGS. 25A-D).

Figure 26:
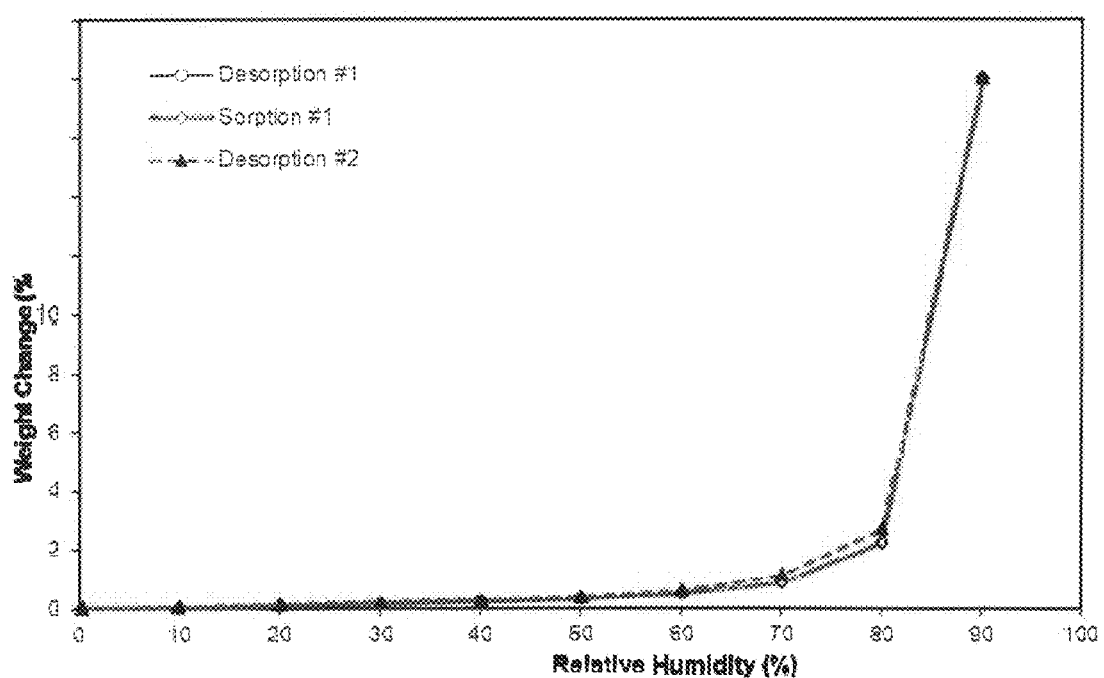
FIG. 26 shows the dynamic vapor sorption (DVS) isotherm of 15-HETrE lysine salt.

Hyper DSC analysis of the material indicated that the glass transition ($T_g$) temperature was 16° C. (half $C_p$ value, FIG. 26).

DVS analysis of the 15-HETrE lysine salt showed less than 1% weight gain below 70% RH but gained an additional 1% between 70-80% RH (FIG. 26) and indicates that the material was hygroscopic according to the European Pharmacopeia classification. The weight gain above 80% RH was sufficiently large to suggest that the sample deliquesced. Post DVS XRPD analysis of the sample showed that it was consistent with that of the input material (FIG. 21).

Figure 27:
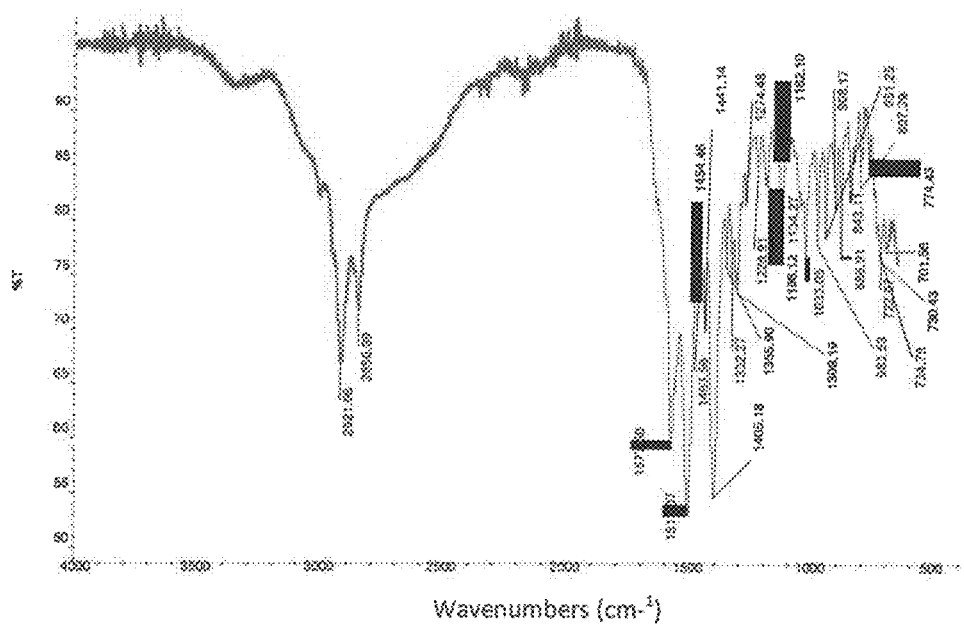
FIG. 27 shows the FT-IR spectrum of 15-HETrE lysine salt.

FIG. 27 shows the FT-IR spectrum of the 15-HETrE lysine salt prepared according to Example 9.

Example 11: Scale Up and Operability Study of 15-HETrE Lysine Salt

Initially the 15-HETrE lysine salt was isolated by rotary evaporation in order to remove residual solvent and reduce stickiness of the solids. However, a small number of experiments were carried out to find a more suitable method that could be used to prepare the salts as dry solids on a larger scale.

Slurry experiments were set up to form the lysine salt under different conditions. Solvents were added according to Table 4 below, Solvent:antisolvent ratios were 1:3.

TABLE 4

Slurry experiments to prepare HETrE lysine salt

| Sample No. | Solvent/ antisolvent | Observations | XRPD |
| --- | --- | --- | --- |
| 1946-035-01 | EtOAc | off white powder | same as previous lysine salts |
| 1946-035-02 | Acetone-EtOAc | off white powder | same as previous lysine salts, some new peaks |
| 1946-035-03 | EtOH-MTBE | off white powder with yellow waxy solid | same as previous lysine salts |
| 1946-035-04 | IPA-EtOAc | off white powder with yellow waxy solid | same as previous lysine salts |
| 1946-043-01 | EtOAc | white solid in solution | same as previous lysine salts |
| 1946-047-01 | EtOAc | yellow/peach solid | HETrE lysine salt + free lysine |
| 1946-055-01 | EtOAc | white/cream solid | HETrE lysine salt |
| 1946-055-02 | EtOAc-EtOH | white/cream solid | HETrE lysine salt + free lysine |
| 1946-055-03 | EtOAc-acetone | white/cream solid | HETrE lysine salt |
| 1946-055-04 | EtOAc-IPA | white/cream solid | HETrE lysine salt |
| 1946-055-05 | EtOAc-MeOH | white/cream solid | HETrE lysine salt |
| 1946-059-01 | EtOAc | cloudy solution | N/A |
| 1946-059-02 | EtOH | white/cream solid | HETrE lysine salt |
| 1946-059-03 | 10:1 EtOAc:MeOH | white/cream solid | HETrE lysine salt |
| 1946-059-04 | Acetone | yellow/brown solution | N/A |
| 1946-059-05 | IPA | white/cream solid | HETrE lysine salt |
| 1946-063-01 | 10:1 EtOAc:MeOH | pale yellow solid | HETrE lysine salt |
| 1946-067-01 | 10:1 EtOAc:MeOH | pale yellow solid | HETrE lysine salt |

The 15-HETrE lysine slurries yielded off white powders with some waxy yellow solids. The XRPD pattern matched previous 15-HETrE lysine salt patterns. Sample 1946-035-01 in EtOAc was selected for scale up to 100 mg, followed by 1 g scale.

The material scaled up successfully at 100 mg, however, issues were encountered when preparing the salt on a 1 g scale.

The reaction took much longer than previously observed to go to completion (6 days vs. 1 day).

The material appeared to be very fine and could not be easily filtered. The 15-HETrE lysine salt was isolated via centrifugation, decanted and dried under vacuum. The material was isolated as a yellow solid but was contaminated with residual lysine.

Further experiments were conducted to find an alternative solvent and EtOAc-MeOH (9:1) was found to be most suitable as salt formation occurred within 1 hour of addition. Other solvent combinations generated the salt but required several hours or overnight mixing. Scale up on 250 mg then 800 mg scales were successful and salt was formed within several hours, filtered and dried.

Purity by UPLC was 96% for the 800 mg scale batch and 97% for the 250 mg scale batch.

Figure 28:
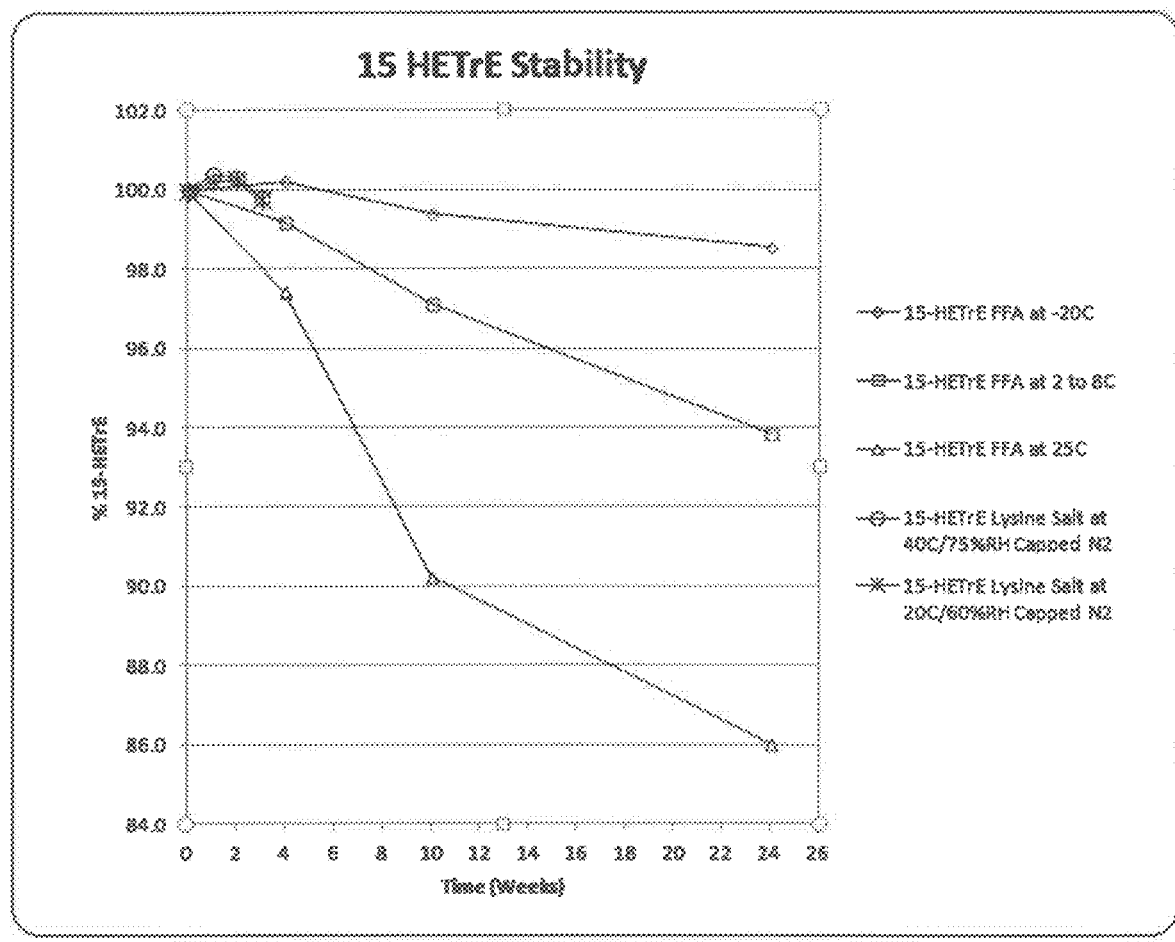
FIG. 28 shows the stability of 15-HETrE free acid ("15-HETrE FFA") when stored for up to 24 weeks at −20° C., at 2-8° C., and at 25° C., and 15-HETrE lysine salt when stored capped under nitrogen gas at 40° C. and 75% RH ("15-HETrE Lysine Salt 40/75") and at 20° C. and 60% RH ("15-HETrE Lysine Salt 20/60").

FIG. 28 shows the stability of the 15-HETrE-lysine salt compared to 15-HETrE free fatty acid at various conditions. Free 15-HETrE is unstable and degrades at all conditions with the exception of −20° C. The 15-HETrE-lysine salt is stable at 20° C. and 40% humidity as well as at 40° C. and 75% humidity, making the lysine salt useful for pharmaceutical applications. 15-HETrE lysine salt was prepared on a larger scale for the crystallization screen as a white powder. XRPD analysis indicated that it was disordered and was very similar to previous analyses.

evidenced by peak shifting of 15-HETrE protons (FIG. 10). Stoichiometry could not be determined by $^1$H-NMR spectroscopy.

TG/DTA analysis of the 15-HETrE sodium salt displayed a continuous gradual weight loss above ambient temperature, which is not unusual for very disordered materials and is probably due to loss of volatile components.

DSC thermogram displayed a complex series of small thermal events, the causes of which are unknown.

A distinct glass transition ($T_g$) signal was not observed from the hyper DSC thermogram.

DVS analysis of the 15-HETrE-sodium salt showed that the sample gained less than 1% weight below 40% RH but exponentially increased in weight gain thereafter and deliquesced at high RH. This indicates that the material is very hygroscopic according to the European Pharmacopeia classifications. Post DVS XRPD analysis was not conducted as the material deliquesced.

FIG. 15 shows the FT-IR spectrum for 15-HETrE sodium salt prepared according to this Example.

Initially the 15-HETrE sodium salt was isolated by rotary evaporation in order to remove residual solvent and reduce stickiness of the solids. However, a small number of experi-

TABLE 5

Crystallization screen of 15-HETrE lysine salt

| Sample No. (1922-) | Solvent/ antisolvent | Conditions | Observations |
| --- | --- | --- | --- |
| 077-01 | EtOH-water | Rotary evap | Large scale prep |
| 087-01 | 1:1:1 MeOH:ACN:Dioxane | evaporation | off white powder |
| 087-02 | 20:1 Dioxane:water | evaporation | off white powder, slightly sticky powder, some birefringence |
| 087-03 | 3:1:3 MIBK:Acetone:MeOH | evaporation | orange tinged powdery solid, slightly sticky with clumps, little birefringence |
| 091-01 | EtOAc | vapor stress | slightly sticky powder, minor birefringence |
| 091-02 | acetone | vapor stress | slightly sticky powder, minor birefringence |
| 091-03 | DCM | vapor stress | slightly sticky powder, minor birefringence |
| 083-01 | MTBE | slurry (RT) | off white waxy solid. Mesophase, birefringence film |
| 083-02 | isobutyl acetate | slurry (RT) | white paste |
| 083-03 | cyclohexane | slurry (RT) | white paste-mesophase. Film, some birefringence |
| 083-02A | Et$_2$O/MTBE | slurry (RT) | white solid |
| 083-03A | EtOH/EtOAc | slurry (RT) | Birefringent gel with white solid |
| 083-03A | — | Vac drying | birefringent white sticky solid |
| 083-04 | Et$_2$O | slurry (RT) | yellow waxy solid. Mesophase. Spherulites. Film, some birefringence |
| 083-04A | Dioxane/EtOAc | slurry (RT) | Yellow sticky solid + solution |
| 083-04A | — | Vac drying | Birefringent yellow solid |
| 087-01A | ACN/EtOAc | slurry (RT) | pale yellow gel |
| 087-02A | Acetone/EtOAc | slurry (RT) | pale yellow gel with solid |
| 087-02A | — | Vac drying | pale yellow solid |
| 087-03A | Cyclohexane/EtOAc | slurry (RT) | pale yellow solid with solution |
| 087-03A | — | vac drying | pale yellow solid |
| 091-01A | DCM/EtOAc | slurry (RT) | pale yellow solid with solution |
| 091-02A | MeOH/EtOAc | slurry (RT) | pale yellow solid with some crystals |
| 091-03A | Et$_2$O/EtOAc | slurry (RT) | white solid in solution |

Example 12: Scale Up and Operability Study of 15-HETrE Sodium Salt

The 15-HETrE sodium salt was a highly disordered by XRPD analysis (FIG. 9) and was a waxy solid.

Analysis of the material by $^1$H-NMR spectroscopy (solvent: d$_4$-MeOD), indicated salt formation had occurred, as ments were carried out to find a more suitable method that could be used to prepare the salts as dry solids on a larger scale.

Slurry experiments were set up to form the sodium salt under different conditions. Solvents were added according to the table below, Solvent: antisolvent ratios were 1:3.

For non-aqueous slurries, the base was added as a solid but did not dissolve. Addition of base as an aqueous solution was also tried but precipitation of salt did not occur and solvent had to be evaporated. Therefore, a suitable slurry method was not found to prepare HETrE sodium salt.

Scale up was carried out using rotary evaporation on a gram scale and generated the salt but the solid exhibited a yellow coloration.

Purity as measured by UPLC was ~81%.

TABLE 6

Attempts to prepare 15-HETrE sodium salt by a slurry method

| Sample No. | Solvent/antisolvent | Observations |
|---|---|---|
| 1946-035-05 | EtOAc[1] | cloudy solution |
| 1946-035-06 | Acetone-EtOAc[1] | cloudy solution |
| 1946-035-07 | EtOH-MTBE[1] | cloudy solution |
| 1946-035-08 | IPA-EtOAc[1] | cloudy solution |
| 1946-035-09 | MTBE-EtOH | cloudy solution |
| 1946-035-10 | heptane-EtOH | cloudy solution |
| 1946-035-11 | cyclohexane-EtOH | cloudy solution |

TABLE 6-continued

Attempts to prepare 15-HETrE sodium salt by a slurry method

| Sample No. | Solvent/antisolvent | Observations |
|---|---|---|
| 1946-035-12 | IPOAc-EtOH | cloudy solution |
| 1946-035-05A | acetone | solution, not dissolved |
| 1946-035-06A | ACN | solution, not dissolved, yellow solid |
| 1946-035-07A | DMF | cloudy yellow solution, not dissolved |
| 1946-035-08A | DMSO | pale yellow solution, not dissolved |
| 1946-035-09A | EtOH | cloudy solution, not dissolved |
| 1946-035-10A | IPA | cloudy solution, not dissolved |
| 1946-035-11A | MeOH | cloudy solution, not dissolved |
| 1946-035-12A | THF | cloudy solution, not dissolved |
| 1946-035-05B | Acetone-$H_2O$ | solution, pale yellow, not dissolved |
| 1946-035-12B | THF-$H_2O$ | solution, pale yellow, not dissolved |
| 1946-045-01 | Acetone[2] | solution, yellow |
| 1946-045-02 | THF[2] | solution, slightly yellow |

Note[1]:
560 μL additional MTBE added to try form precipitate.
Note[2]:
saturated aqueous $NaHCO_3$ was added to slurry.

TABLE 7

Crystallization screen of HETrE sodium salt

| Sample No. (1922-) | Solvent/antisolvent | Conditions | Observations |
|---|---|---|---|
| 075-01 | EtOH-water | Rotary evap | Large scale prep |
| 085-01 | 1:1:1 MeOH:ACN:Dioxane | evaporation | mesophase. Spherulites, slightly sticky particles, some birefingence |
| 085-03 | 3:1:1 MIBK:Acetone:MeOH | evaporation | mesophase - looks like small needles in mesophase |
| 085-02 | 20:1 Dioxane:water | evaporation | mesophase, slightly sticky particles, some birefringence |
| 089-01 | EtOAc | vapour stress | slightly sticky with some birefringence, powder |
| 089-02 | acetone | vapour stress | slightly sticky with some birefringence |
| 089-03 | DCM | vapour stress | slightly sticky with some birefringence |
| 079-01 | MTBE | slurry (RT) | off white waxy solid - bright colors, birefringence film |
| 079-02 | Isobutyl acetate | Slurry (RT) | white gel, paste bright colors |
| 079-02A | EtOH-MTBE | slurry (RT) | white gel |
| 079-03 | cyclohexane | slurry (RT) | white paste at bottom. Solid round sides, sticky powder |
| 079-03A | Dioxane- MTBE | slurry (RT) | yellow solid, gel |
| 079-04 | $Et_2O$ | slurry (RT) | white/clear waxy solid, birefringent, birefringence film |
| 085-01A | ACN- MTBE | slurry (RT) | Birefringent waxy solid |
| 085-01A | — | vacuum drying | birefringent waxy solid |
| 085-02A | Acetone- MTBE | slurry (RT) | Birefringent waxy solid |
| 085-02A | — | vacuum drying | birefringent waxy solid |
| 089-01A | Cyclohexane-MTBE | slurry (RT) | Birefringent, waxy solid off- white |
| 089-01A | — | vacuum drying | Birefringent, waxy solid off-white |
| 089-02A | DCM- MTBE | slurry (RT) | Birefringent, waxy white solid |
| 089-02A | — | vacuum drying | Birefringent, waxy white solid |
| 089-03A | MeOH- MTBE | slurry (RT) | Yellow sticky solid, some Birefringence |
| 089-03A | — | vacuum drying | Yellow sticky solid, some Birefringence |

Figure 29:
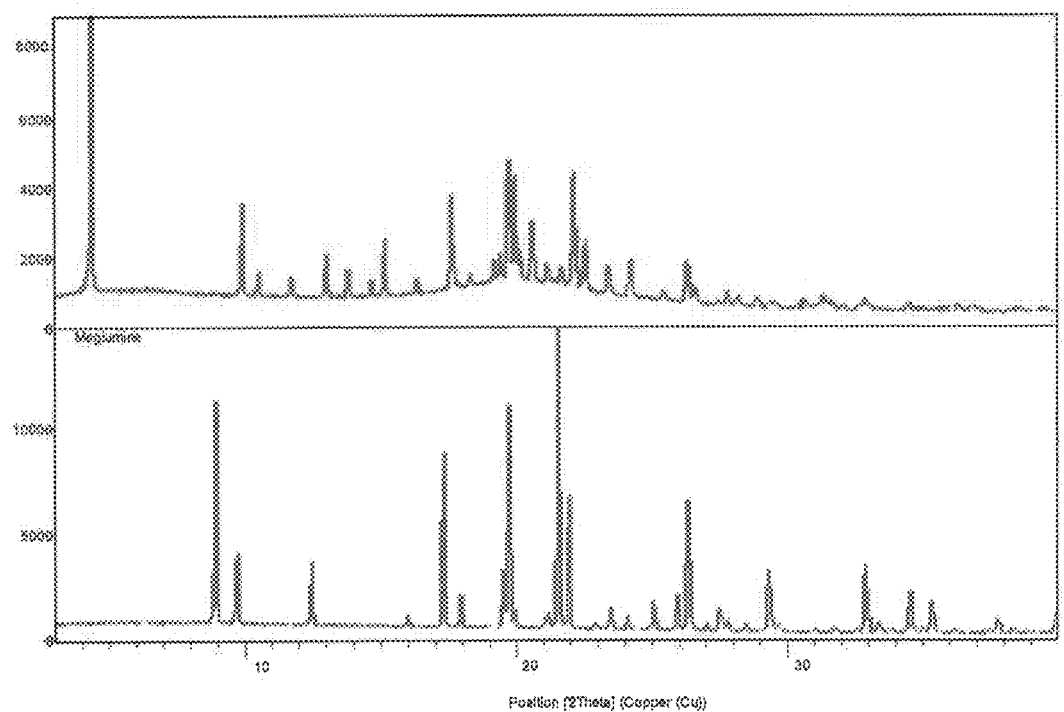
FIG. 29 shows a comparison of X-ray powder diffraction patterns for solids isolated from 15-HETrE and meglumine (top panel) and meglumine (bottom panel).

Example 13: Scale Up and Operability Study of 15-HETrE Sodium Meglumine Salt A sample prepared from 15-HETrE with N-methyl-D-glucamine (meglumine) yielded a gel and was stored under refrigerated conditions to encourage crystallization. After some time, it was noticed that the material had solidified and the XRPD pattern indicated presence of crystallinity, although there was some amorphous content as well (FIG. 29). The XRPD pattern was different to that of meglumine indicating formation of a unique solid form.

Figure 30:
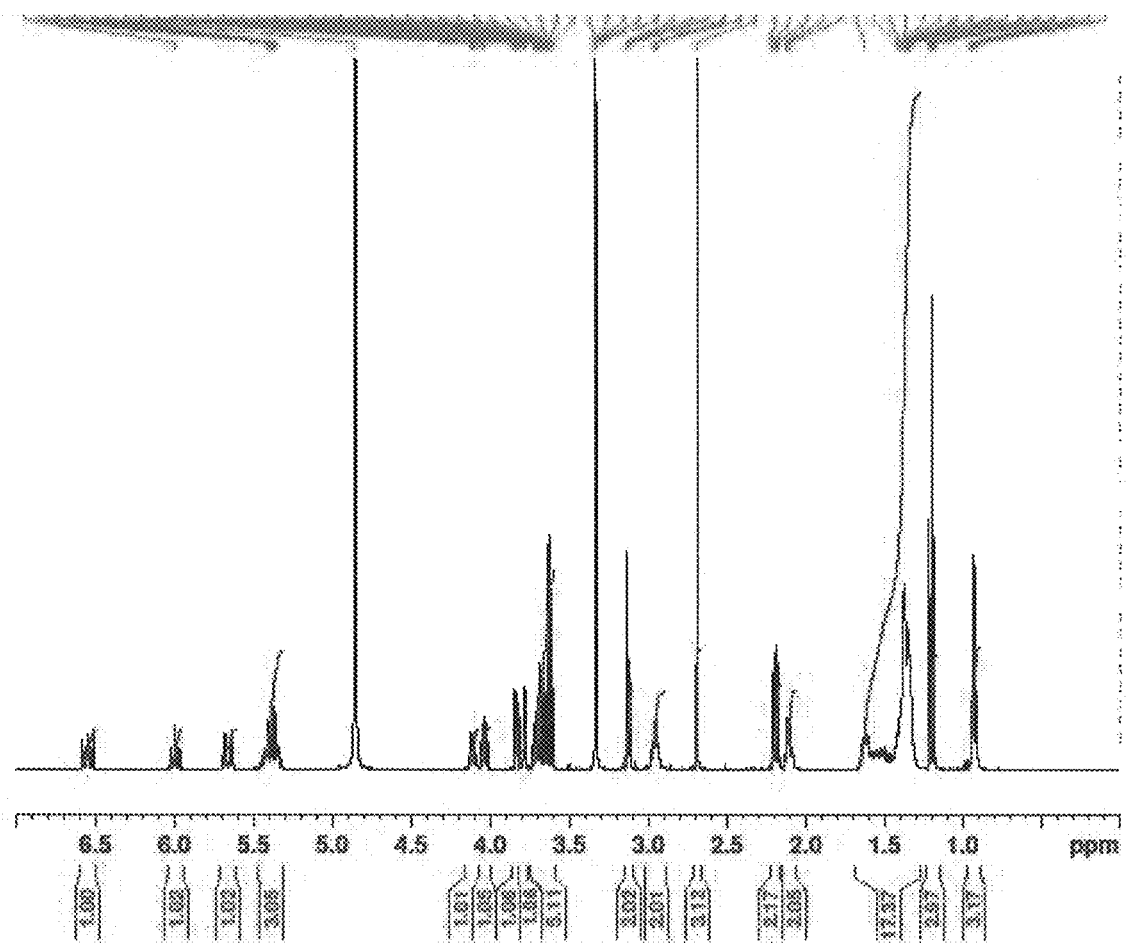
FIG. 30 shows the proton NMR spectrum of solids isolated from 15-HETrE and meglumine.

Proton NMR spectrum of the sample indicated a 1:1 stoichiometry and peak shifting was noted indicating salt formation (FIG. 30). One mole of EtOH was detected, which may indicate solvate formation.

Figures 31A, 31B:
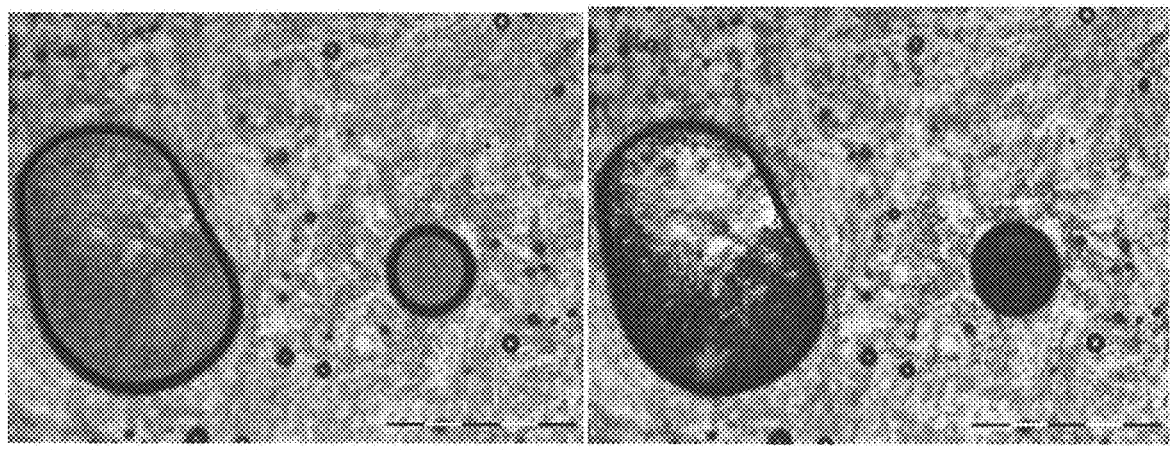
FIGS. 31A-B show 10× photomicrographs of 15-HETrE meglumine salt captured with first order red plate (FIG. 31A) and with crossed-polarized light (FIG. 31B).

Although the XRPD pattern indicated that it was the most crystalline sample generated from the screen, the sample was a sticky solid and flowed when pressed between microscope slides indicating liquid crystalline properties (FIGS. 31A-B). The scale bar in FIGS. 31A-B represents 200 μm. The material was dried overnight under vacuum to remove residual EtOH and the sample was still sticky.

15-HETrE meglumine salt was prepared on a larger scale for the crystallization screen as a viscous oil.

The meglumine salt was then subdivided into multiple vials and subjected to different stress conditions and samples purged with nitrogen (Table 8). Aqueous and non-aqueous conditions were employed and solvents dried using molecular sieves. Solvents were also purged with nitrogen.

Most of the samples remained gels when stressed under different conditions. However, one sample partially crystallized in the fridge from ACN-EtOH. The sample was used for seeding other samples but no further crystallization was noted.

TABLE 8

Crystallization screen for 15-HETrE meglumine salt

| Sample No. | Solvent/antisolvent | Conditions | Observations |
|---|---|---|---|
| 1922-073-01 | EtOH-water | Rotary evap | Large scale prep |
| 1922-081-09 | — | 40° C./75% RH | dark yellow gel |
| 1922-095-06 | — | temp. stress | pale yellow gel |
| 1922-093-01 | EtOAc-EtOH | vapor stress | solution |
| 1922-093-01 | — | vacuum drying | pale yellow gel |
| 1922-093-02 | acetone-EtOH | vapor stress | Solution. |
| 1922-093-02 | — | vacuum drying | pale yellow gel |
| 1922-093-03 | DCM-EtOH | vapor stress | solution |
| 1922-093-03 | — | vacuum drying | pale yellow gel |
| 1922-093-04 | ACN-EtOH | vapor stress | white solid, birefringent needles. Melted when removed from fridge. Used as seeds. Solidified in fridge to white solid, sticky, agglomerates |
| 1922-093-05 | THF-EtOH | vapor stress | solution |
| 1922-093-05 | — | vacuum drying | pale yellow gel |
| 1922-093-10 | water-EtOH | vapor stress | solution |
| 1922-093-10 | — | vacuum drying | pale yellow gel |
| 1922-081-07 | EtOH-water | slurry (RT) | solution |
| 1922-081-08 | EtOH:IPOAc | slurry (RT) | solution |
| 1946-003-01 | water-EtOH | slurry (RT) | solution |
| 1946-003-01 | — | vacuum drying | pale yellow gel |
| 1946-003-02 | IPOAc-EtOH | slurry (RT) | solution |
| 1946-003-02 | — | vacuum drying | pale yellow gel |
| 1946-003-03 | ACN-MTBE | slurry (RT) | solution |
| 1946-003-03 | — | vac drying | pale yellow gel |
| 1946-003-04 | acetone-MTBE | slurry (RT) | gel. Seeded with 1922-093-04 |
| 1946-003-04A | — | seeding | yellow gel with seed |
| 1946-003-05 | cyclohexane-MTBE | slurry (RT) | gel. Seeded with 1922-093-04 |
| 1946-003-05A | — | seeding | yellow gel with seed |
| 1946-003-06 | | | |
| 1946-003-06 | — | vac drying | pale yellow gel |
| 1946-003-07 | dioxane-EtOAc | slurry (RT) | Solution |
| 1946-003-07 | — | vac drying | pale yellow gel |

Based on these results, 15-HETrE lysine and sodium salts still represent the best candidates for further study as they are less sticky than the meglumine salt. However, the properties of the meglumine salt may show improvement with further processing.

Example 14: Preparation of 15-(S)-HETrE from DGLA

Sodium borate buffer (0.1 M) was prepared by charging boric acid (61.8 g, 1 mol) and NaOH (120.0 g, 3 mol) in water (10 L). A 20 L hastealloy vessel was charged with 10.0 L of the sodium borate buffer, followed by cysteine (237.2 g, 1.958 mol, 2.0 equiv). After the buffer and cysteine were fully dissolved with stirring, DGLA (300 g, 9.79 mol) was added and the mixture was cooled to 0-5° C. at pH 9.6. LPX1 enzyme powder (2.66 g, 8.85 mg/g DGLA, 1.8 Munits/g DGLA, 0.88 wt. %) was added and the vessel was pressurized to 2.5 bar with pure oxygen. After stirring for one hour, the oxygen head pressure was slowly released to avoid foaming. An aliquot was removed and acidified to pH 3 with citric acid solution (25% w/v). The aliquot was extracted with deuterated chloroform, dried over sodium sulfate, filtered and analyzed by NMR.

Additional LPX1 enzyme powder (0.503 g, 1.8 mg/g DGLA, 0.36 Munits/g DGLA, 0.18 wt. %) and one additional equivalent of cysteine (117.0 g, 0.979 mol) were added and the mixture was stirred under oxygen for another hour. Analysis of another aliquot as described above indicated that the reaction was complete.

The mixture was purged with nitrogen (2 bar, 2 cycles) and stirred at 900 rpm overnight under a blanket of nitrogen. The mixture was then charged to a nitrogen-blanketed 10 L jerry can. The mixture was then added to a 20 L reactor under a blanket of argon and solid citric acid was added in 50 g portions until the pH dropped to 3.5.

Precipitated solid was collected with a sintered funnel under argon. After transferring the solids back to the reactor, 3 L of methyl t-butyl ether (MtBE) were added and the mixture was stirred at 400 rpm for 10 minutes. These steps were repeated twice more before residual solvent was evaporated at 250 mbar with a 40° C. bath (rotovap) until no more distillate was observed. The rotovap was vented with argon.

Example 15: Purification of Crude 15-(S)-HETrE by Chromatography

Half of the crude 15-(S)-HETrE prepared in Example 14 was dissolved in 130 mL of a MtBE/cyclohexane (20:80 v/v) solvent mixture. The solution was divided into two portions; each portion was purified using a Biotage 75L silica cartridge which had been pre-eluted with cyclohexane. Elution of the 15-(S)-HETrE was accomplished in 5 stages: (1) MtBE/cyclohexane (10:90): 4 L; (2) MtBE/cyclohexane (20:80): 3 L; (3) MtBE/cyclohexane (30:70): 2 L; (4) MtBE/cyclohexane (50:50): 4 L; and (5) MtBE: 2 L. Fractions including 15-(S)-HETrE by TLC analysis (fractions 4-9) were combined and concentrated by rotovap (250 mbar at 40° C.), under argon until no more distillate was observed. Purity was 95.5% (by $^1$H-NMR) or 96.4% (by uHPLC).

Example 16: Preparation of 15-(S)-HETrE L-Lysine Salt

L-Lysine mono-hydrate (399±2 mg) was suspended in alcohol (Table 9) in a 20 mL snap cap vial, 15-(S)-HETrE (803±2 mg) was dissolved in the non-polar solvent (4 mL) and added to the stirring suspension of lysine, further non-polar solvent (2 mL) was used to rinse the HETrE vial and added to the lysine/HETrE suspension. The balance of the non-polar solvent was then added (total volume of solvent added was 8 mL), seed was added at this point for experiment 3 to 10, and stirred at 250 rpm overnight.

TABLE 9

Solvent systems.

| Reaction No. | Solvent (non-polar) | Solvent (polar) | ratio |
|---|---|---|---|
| 2032-001-1 | Ethyl acetate | methanol | 95:5 |
| 2032-001-2 | Ethyl acetate | methanol | 90:10 |
| 2032-001-3 | Ethyl acetate | ethanol | 90:10 |
| 2032-001-4 | Ethyl acetate | Isopropyl alcohol | 80:20 |
| 2032-001-5 | Ethyl acetate | acetone | 80:20 |
| 2032-001-6 | Iso-propyl acetate | methanol | 95:5 |
| 2032-001-7 | Iso-propyl acetate | methanol | 90:10 |
| 2032-001-8 | Iso-propyl acetate | ethanol | 90:10 |
| 2032-001-9 | Iso-propyl acetate | Isopropyl alcohol | 80:20 |
| 2032-001-10 | Iso-propyl acetate | acetone | 80:20 |

Reaction Nos. 1 and 2 were not seeded; Reaction Nos. 3 to 10 were seeded with seeds obtained from the filter cake of Reaction No. 1.

Products of each of the Reactions were white in appearance. Filtration was carried out with a sintered funnel (no. 3, 10 mm diameter) under mild vacuum. Some filter cake products were yellow in appearance. The first ~200 µL of filtrate were transferred into an HPLC vial. Filtration of the remaining reaction mixture (alternating between high and medium vacuum) yielded a filter cake that was transferred to a vacuum chamber and dried overnight before being stored in a freezer. The salt itself is insoluble in chloroform and DMSO, but dissolves readily in water.

NMR analysis in $D_2O$ was used to determine lysine content of the salt (Table 10) by calibrating the alpha proton of lysine to 1.

TABLE 10

Lysine content of 15(S)-HETrE L-lysine salts.

| Reaction No. | Lysine signal | HEtrE at 5.6 ppm | difference | HETrE at 6 ppm | difference |
|---|---|---|---|---|---|
| 2032-001-1 | 1 | 0.9493 | 0.01941 | 0.94 | 0.00698 |
| 2032-001-2 | 1 | 0.9095 | −0.02039 | 0.9164 | −0.01662 |
| 2032-001-3 | 1 | 0.9277 | −0.00219 | 0.9622 | 0.02918 |
| 2032-001-4 | 1 | 0.9283 | −0.00159 | 0.9237 | −0.00932 |
| 2032-001-5 | 1 | 0.9488 | 0.01891 | 0.9371 | 0.00408 |
| 2032-001-6 | 1 | 0.9503 | 0.02041 | 0.9451 | 0.01208 |
| 2032-001-7 | 1 | 0.9247 | −0.00519 | 0.9115 | −0.02152 |
| 2032-001-8 | 1 | 0.9032 | −0.02669 | 0.9434 | 0.01038 |
| 2032-001-9 | 1 | 0.9407 | 0.01081 | 0.9311 | −0.00192 |
| 2032-001-10 | 1 | 0.9164 | −0.01349 | 0.9197 | −0.01332 |
| average = | | 0.92989 | | 0.93302 | |

Observations of the Reactions are summarized in Table 11.

TABLE 11

| Reaction No. | Solvent | ratio | Cake weight (mg) | Cake purity (%) | Filtrate purity (%) | Filtration time approx. (mins) | Filter cake appearance | Slurry mobility | Drainage |
|---|---|---|---|---|---|---|---|---|---|
| 2032-001-1 | Ethyl acetate/methanol | 95:5 | 921 | 97.1 | 83.05 | 35 | Y, H | 4 | 3 |
| 2032-001-2 | Ethyl acetate/methanol | 90:10 | 990 | 97.1 | 82.77 | 30 | W, P | 4 | 3 |
| 2032-001-3 | Ethyl acetate/ethanol | 90:10 | 945 | 97.1 | 82.61 | 25 | Y, H | 4 | 3 |

TABLE 11-continued

| Reaction No. | Solvent | ratio | Cake weight (mg) | Cake purity (%) | Filtrate purity (%) | Filtration time approx. (mins) | Filter cake appearance | Slurry mobility | Drainage |
|---|---|---|---|---|---|---|---|---|---|
| 2032-001-4 | Ethyl acetate/Isopropyl alcohol | 80:20 | 813 | 97.1 | 82.13 | 30 | Y, H | 4 | 3 |
| 2032-001-5 | Ethyl acetate/acetone | 80:20 | 1113 | 96.8 | — | 50 | Y, H | 5 | 4 |
| 2032-001-6 | isopropyl acetate/methanol | 95:5 | 932 | 97.2 | 86.91 | 30 | Y, H | 4 | 3 |
| 2032-001-7 | isopropyl acetate/methanol | 90:10 | 1000 | 96.8 | 81.04 | 35 | W, P | 4 | 3 |
| 2032-001-8 | isopropyl acetate/ethanol | 90:10 | 951 | 97.1 | 83.39 | 35 | Y, H | 4 | 3 |
| 2032-001-9 | isopropyl acetate/Isopropyl alcohol | 80:20 | 932 | 96.9 | 80.24 | 35 | Y, H | 4 | 3 |
| 2032-001-10 | isopropyl acetate/acetone | 80:20 | 910 | 96.8 | 79.64 | 50 | Y, H | 5 | 4 |

Filtration time: time for cake to reach semi dry state, not wet
Filter cake appearance: appearance of cake after drying, w = white, y = yellow (colour of cake), H = hard, P = powdery
Slurry mobility: 1 = thin, very mobile, 2 = medium thick, mobile, 3 = thick but transfer mostly prior to rinsing, 4 = thick not easily transferable, 5 = very thick, no flow without fresh diluent
Drainage (suction filtration): 1 = easily, 2 = medium, 3 = difficult, 4 = none The impurity profile of Reaction Nos. 1 to 10 are shown in Table 12.

TABLE 12

Impurity profiles

| | RRT | retention time | peak area (%) | 001-1 (salt) | 001-1 (liquor) | 001-2 (salt) | 001-2 (liquor) | 001-3 (salt) | 001-3 (liquor) |
|---|---|---|---|---|---|---|---|---|---|
| IMP 1 | 0.62 | 4.35 | 0.13 | 0.03 | 0.35 | 0.02 | 0.25 | 0.02 | 0.31 |
| IMP 2 | 0.64 | 4.44 | 0.19 | 0.05 | 0.5 | 0.04 | 0.36 | 0.04 | 0.47 |
| IMP 3 | 0.69 | 4.81 | 0.31 | 0.07 | 0.78 | 0.05 | 0.56 | 0.06 | 0.71 |
| IMP 4 | 0.91 | 6.34 | 1.22 | 0.95 | 2.9 | 1.01 | 2.61 | 0.99 | 3.23 |
| HETrE | 1 | 6.97 | 97.3 | 97.07 | 83.05 | 97.09 | 82.77 | 97.11 | 82.61 |
| IMP 5 | 1.03 | 7.2 | 0 | 0.11 | 0.8 | 0.1 | 0.89 | 0.12 | 1.09 |
| IMP 6 | 1.1 | 7.7 | 1.5 | 1.48 | 1.54 | 1.45 | 1.54 | 1.48 | 1.57 |
| IMP 7 | 1.75 | 12.25 | unknown | 0.1 | 2.87 | 0.1 | 3.3 | 0.11 | 3.56 |

| | RRT | retention time | peak area (%) | 001-4 (salt) | 001-4 (liquor) | 001-5 (salt) | 001-5 (liquor) | 001-6 (salt) | 001-6 (liquor) |
|---|---|---|---|---|---|---|---|---|---|
| IMP 1 | 0.62 | 4.35 | 0.13 | 0.03 | 0.42 | 0.03 | — | 0.03 | 0.19 |
| IMP 2 | 0.64 | 4.44 | 0.19 | 0.04 | 0.51 | 0.05 | — | 0.04 | 0.27 |
| IMP 3 | 0.69 | 4.81 | 0.31 | 0.06 | 0.86 | 0.07 | — | 0.06 | 0.43 |
| IMP 4 | 0.91 | 6.34 | 1.22 | 0.99 | 3.59 | 0.99 | — | 0.96 | 2.32 |
| HETrE | 1 | 6.97 | 97.3 | 97.07 | 82.13 | 96.77 | — | 97.17 | 86.91 |
| IMP 5 | 1.03 | 7.2 | 0 | 0.12 | 1.17 | 0.12 | — | 0.12 | 0.62 |
| IMP 6 | 1.1 | 7.7 | 1.5 | 1.47 | 1.7 | 1.46 | — | 1.42 | 1.67 |
| IMP 7 | 1.75 | 12.25 | unknown | 0.13 | 3.77 | 0.18 | — | 0.12 | 2.15 |

| | RRT | retention time | peak area (%) | 001-7 (salt) | 001-7 (liquor) | 001-8 (salt) | 001-8 (liquor) | 001-9 (salt) | 001-9 (liquor) |
|---|---|---|---|---|---|---|---|---|---|
| IMP 1 | 0.62 | 4.35 | 0.13 | 0.03 | 0.4 | 0.02 | 0.33 | 0.02 | 0.43 |
| IMP 2 | 0.64 | 4.44 | 0.19 | 0.05 | 0.43 | 0.04 | 0.51 | 0.05 | 0.64 |
| IMP 3 | 0.69 | 4.81 | 0.31 | 0.05 | 0.67 | 0.05 | 0.75 | 0.05 | 0.92 |
| IMP 4 | 0.91 | 6.34 | 1.22 | 1.07 | 2.65 | 0.96 | 2.9 | 1.01 | 3.07 |
| HETrE | 1 | 6.97 | 97.3 | 96.83 | 81.04 | 97.1 | 83.39 | 96.92 | 80.24 |
| IMP 5 | 1.03 | 7.2 | 0 | 0.12 | 1.17 | 0.12 | 0.86 | 0.12 | 1.06 |
| IMP 6 | 1.1 | 7.7 | 1.5 | 1.48 | 1.62 | 1.44 | 1.62 | 1.48 | 1.6 |
| IMP 7 | 1.75 | 12.25 | unknown | 0.13 | 4.08 | 0.11 | 3.36 | 0.13 | 4.08 |

| | RRT | retention time | peak area (%) | 001-10 (salt) | 001-10 (liquor) |
|---|---|---|---|---|---|
| IMP 1 | 0.62 | 4.35 | 0.13 | 0.03 | 0.42 |
| IMP 2 | 0.64 | 4.44 | 0.19 | 0.07 | 0.59 |
| IMP 3 | 0.69 | 4.81 | 0.31 | 0.07 | 0.82 |
| IMP 4 | 0.91 | 6.34 | 1.22 | 0.99 | 3.1 |
| HETrE | 1 | 6.97 | 97.3 | 96.8 | 79.64 |

TABLE 12-continued

| Impurity profiles | | | | | |
|---|---|---|---|---|---|
| IMP 5 | 1.03 | 7.2 | 0 | 0.11 | 1.01 |
| IMP 6 | 1.1 | 7.7 | 1.5 | 1.46 | 1.68 |
| IMP 7 | 1.75 | 12.25 | unknown | 0.18 | 3.43 |

Example 17: Investigation of Methanol as Co-Solvent

Based on the results of Example 16, ratios of methanol with ethyl acetate or isopropyl acetate were investigated to determine effects on 15-(S)-HETrE yield, as shown in Table 13.

TABLE 13

| Exp. No. | Solvent (non-polar) | Solvent (polar) | ratio |
|---|---|---|---|
| 009-1 | Ethyl acetate | methanol | 90:10 |
| 009-2 | Ethyl acetate | methanol | 85:15 |
| 009-3 | Ethyl acetate | methanol | 80:20 |
| 009-4 | Iso-propyl acetate | methanol | 90:10 |
| 009-5 | Iso-propyl acetate | methanol | 85:15 |
| 009-6 | Iso-propyl acetate | methanol | 80:20 |

Results of the reactions are summarized in Table 14.

TABLE 14

| Exp. No. | Cake weight (mgs) | Cake purity (%) | Filtrate purity (%) | Filtration time approx. (mins) | Filter cake appearance | Slurry mobility | Drainage |
|---|---|---|---|---|---|---|---|
| 009-1 | 876* | 96.69 | 78.09 | 30 | W, P | 4 | 3 |
| 009-2 | 996 | 96.73 | 79.28 | 35 | W, P | 4 | 3 |
| 009-3 | 999 | 96.66 | 77.39 | 35 | W, P | 4 | 3 |
| 009-4 | 943 | 96.66 | 79.23 | 30 | W, P | 4 | 3 |
| 009-5 | 1000 | 96.41 | 79.38 | 35 | W, P | 4 | 3 |
| 009-6 | 987 | 96.51 | 76.69 | 30 | W, P# | 4 | 3 |

*reaction filtered through a larger filter initially but transferred to smaller sinter funnel.
= cake had yellow hard characteristics on edge of cake.
Filtration time: time for cake to reach semi dry state, not wet
Filter cake appearance: appearance of cake after drying, w = white, y = yellow (colour of cake), H = hard, P = powdery
Slurry mobility: 1 = thin, very mobile, 2 = medium thick, mobile, 3 = thick but transfer mostly prior to rinsing, 4 = thick not easily transferable, 5 = very thick, no flow without fresh diluent
Drainage (suction filtation): 1 = easily, 2 = medium, 3 = difficult, 4 = none Impurity profiles of the Lysine salt and liquor portions of the experiments are summarized in Table 15.

TABLE 15

| Impurity profiles. | | | | | | | | |
|---|---|---|---|---|---|---|---|---|
| | RRT | retention time | peak area (%) | 009-1 (salt) | 009-1 (liquor) | 009-2 (salt) | 009-2 (liquor) | 009-3 (salt) | 009-3 (liquor) |
| IMP 1 | 0.62 | 4.35 | 0.13 | 0.04 | 0.15 | 0.03 | 0.17 | 0.04 | 0.19 |
| IMP 2 | 0.64 | 4.44 | 0.19 | 0.09 | 0.49 | 0.09 | 0.49 | 0.09 | 0.52 |
| IMP 3 | 0.69 | 4.81 | 0.31 | 0.11 | 1.13 | 0.11 | 1.14 | 0.11 | 1.23 |
| IMP 4 | 0.91 | 6.34 | 1.22 | 1.04 | 2.46 | 0.98 | 2.55 | 1.01 | 2.52 |
| HETrE | 1 | 6.97 | 97.3 | 96.69 | 78.09 | 96.73 | 79.28 | 96.66 | 77.39 |
| IMP 5 | 1.03 | 7.2 | 0 | 0.14 | 0.85 | 0.14 | 0.88 | 0.15 | 0.87 |
| IMP 6 | 1.1 | 7.7 | 1.5 | 1.42 | 1.36 | 1.39 | 1.47 | 1.39 | 1.37 |
| IMP 7 | 1.75 | 12.25 | unknown | 0.23 | 4.44 | 0.25 | 4.24 | 0.26 | 4.45 |
| | RRT | retention time | peak area (%) | 009-4 (salt) | 009-4 (liquor) | 009-5 (salt) | 009-5 (liquor) | 009-6 (salt) | 009-6 (liquor) |
| IMP 1 | 0.62 | 4.35 | 0.13 | 0.04 | 0.22 | 0.05 | 0.23 | 0.03 | 0.32 |
| IMP 2 | 0.64 | 4.44 | 0.19 | 0.13 | 0.49 | 0.13 | 0.51 | 0.04 | 0.52 |
| IMP 3 | 0.69 | 4.81 | 0.31 | 0.14 | 1.1 | 0.07 | 1.17 | 0.14 | 1.18 |
| IMP 4 | 0.91 | 6.34 | 1.22 | 1.01 | 2.54 | 0.99 | 2.57 | 1.06 | 2.61 |
| HETrE | 1 | 6.97 | 97.3 | 96.66 | 79.23 | 96.41 | 79.38 | 96.51 | 76.69 |
| IMP 5 | 1.03 | 7.2 | 0 | 0.14 | 0.89 | 0.12 | 0.84 | 0.14 | 1.14 |
| IMP 6 | 1.1 | 7.7 | 1.5 | 1.39 | 1.56 | 1.46 | 1.5 | 1.39 | 1.46 |
| IMP 7 | 1.75 | 12.25 | unknown | 0.2 | 4.43 | 0.18 | 4.28 | 0.31 | 4.84 |

Example 18. Ratio of Lysine to 15-(S)-HETrE

The effect of the ratio of lysine to 15-(S)-HETrE was investigated using the protocol of Example 16. Initial ratios of lysine and 15-(S)-HETrE used are shown in Table 16.

TABLE 16

| Reaction No. | Solvent (non-polar) | Solvent (polar) | Ratio | Lysine (mol %) |
|---|---|---|---|---|
| 013-1 | Ethyl acetate | Methanol | 85:15 | 97.5 |
| 013-2 | Ethyl acetate | Methanol | 85:15 | 95 |

TABLE 16-continued

| Reaction No. | Solvent (non-polar) | Solvent (polar) | Ratio | Lysine (mol %) |
|---|---|---|---|---|
| 013-3 | Isopropyl acetate | Methanol | 85:15 | 97.5 |
| 013-4 | Isopropyl acetate | Methanol | 85:15 | 95 |
| 013-5 | Ethyl acetate | Methanol | 80:20 | 97.5 |
| 013-6 | Ethyl acetate | Methanol | 80:20 | 95 |

Results of the six reactions are summarized in Table 17.

TABLE 17

| Reaction No. | Cake weight (mg) | Cake purity (%) | Filtrate purity (%) | Filtration time approx. (min) | Filter cake appearance | Slurry mobility | Drainage |
|---|---|---|---|---|---|---|---|
| 013-1 | 972 | 96.43 | 85.66 | 30 | W, P | 4 | 3 |
| 013-2 | 975 | 96.67 | 86.41 | 35 | W, P | 4 | 3 |
| 013-3 | 1011 | 96.83 | 86.73 | 35 | W, P | 4 | 3 |
| 013-4 | 926 | 96.61 | 87.31 | 35 | W, P | 4 | 3 |
| 013-5 | 934 | 96.61 | 86.00 | 30 | W, P | 4 | 3 |
| 013-6 | 827 | 96.47 | 85.85 | 35 | W, P | 4 | 3 |

Filtration time: time for cake to reach semi dry state, not wet
Filter cake appearance: appearance of cake after drying, w = white, y = yellow (colour of cake), H = hard, P = powdery
Slurry mobility: 1 = thin, very mobile, 2 = medium thick, mobile, 3 = thick but transfer mostly prior to rinsing, 4 = thick not easily transferable, 5 = very thick, no flow without fresh diluent The final ratio of lysine to 15-(S)-HETrE was determined by NMR, as shown in Table 18.

TABLE 18

| Reaction No. | lysine peak | peak at 5.6 ppm | difference | peak at 6 ppm | difference |
|---|---|---|---|---|---|
| 013-1 | 1 | 0.9604 | −0.00785 | 0.9435 | −0.00335 |
| 013-2 | 1 | 0.9653 | −0.00295 | 0.9426 | −0.00425 |
| 013-3 | 1 | 0.9726 | 0.00435 | 0.9591 | 0.01225 |
| 013-4 | 1 | 0.9973 | 0.02905 | 0.9528 | 0.00595 |
| 013-5 | 1 | 0.958 | −0.01025 | 0.9478 | 0.00095 |
| 013-6 | 1 | 0.9559 | −0.01235 | 0.9353 | −0.01155 |
| average = | | 0.96825 | | 0.94685 | |

Impurity profiles for the six reactions are shown in Table 19.

TABLE 19

Impurity profiles.

| | RRT | retention time | peak area (%) | 013-1 (salt) | 013-1 (liquor) | 013-2 (salt) | 013-2 (liquor) | 013-3 (salt) | 013-3 (liquor) |
|---|---|---|---|---|---|---|---|---|---|
| IMP 1 | 0.62 | 4.35 | 0.20 | 0.06 | 0.18 | 0.06 | 0.16 | 0.05 | 0.18 |
| IMP 2 | 0.64 | 4.44 | 0.125 | 0.1 | 1.44 | 0.10 | 1.49 | 0.03 | 0.92 |
| IMP 3 | 0.69 | 4.81 | 0.27 | 0.6 | 1.44 | 0.06 | 1.48 | 0.04 | 1.42 |
| IMP 4 | 0.91 | 6.34 | 1.30 | 1.11 | 2.73 | 1.04 | 2.88 | 1.04 | 2.82 |
| HETrE | 1 | 6.97 | 95.67 | 96.43 | 85.66 | 96.67 | 86.41 | 96.83 | 86.73 |
| IMP 5 | 1.03 | 7.2 | 0 | 0.14 | 0.97 | 0.14 | 0.92 | 0.13 | 0.93 |
| IMP 6 | 1.1 | 7.7 | 1.44 | 1.41 | 1.39 | 1.40 | 1.46 | 1.4 | 1.49 |
| IMP 7 | 1.75 | 12.25 | 0.55 | 0.25 | 3.97 | ND | 3.22 | 0.16 | 2.69 |

| | RRT | retention time | peak area (%) | 013-4 (salt) | 013-4 (liquor) | 013-5 (salt) | 013-5 (liquor) | 013-6 (salt) | 013-6 (liquor) |
|---|---|---|---|---|---|---|---|---|---|
| IMP 1 | 0.62 | 4.35 | 0.20 | 0.05 | 0.28 | 0.05 | 0.3 | 0.09 | 0.45 |
| IMP 2 | 0.64 | 4.44 | 0.125 | 0.09 | 0.92 | 0.09 | 0.98 | 0.11 | 1.66 |
| IMP 3 | 0.69 | 4.81 | 0.27 | 0.05 | 1.27 | 0.05 | 1.3 | 0.09 | 1.65 |
| IMP 4 | 0.91 | 6.34 | 1.30 | 1.05 | 2.84 | 1.02 | 2.81 | 1.00 | 2.88 |
| HETrE | 1 | 6.97 | 95.67 | 96.61 | 87.31 | 96.61 | 86.00 | 96.47 | 85.85 |
| IMP 5 | 1.03 | 7.2 | 0 | 0.13 | 0.89 | 0.13 | 0.92 | 0.14 | 0.86 |
| IMP 6 | 1.1 | 7.7 | 1.44 | 1.37 | 1.53 | 1.32 | 1.32 | 1.31 | 1.43 |
| IMP 7 | 1.75 | 12.25 | 0.55 | 0.18 | 2.05 | 0.21 | 3.04 | 0.25 | 2.72 |

Example 19. Removal of DGLA Under 15-(S)-HETrE Salt Formation Conditions

To determine if salt formation conditions could simultaneously purge residual DGLA from the reaction mixture, amounts of DGLA in various solvent systems according to Table 20 were doped into 15-(S)-HETrE before addition of methanolic lysine according to Example 16.

TABLE 20

| Reaction No. | Solvent (non-polar) | Solvent (polar) | Ratio | DGLA (wt. %) |
|---|---|---|---|---|
| 017-1 | Ethyl acetate | Methanol | 85:15 | 1.25 |
| 017-2 | Ethyl acetate | Methanol | 85:15 | 2.5 |
| 017-3 | Ethyl acetate | Methanol | 85:15 | 5 |
| 017-4 | Isopropyl acetate | Methanol | 85:15 | 1.25 |
| 017-5 | Isopropyl acetate | Methanol | 85:15 | 2.5 |
| 017-6 | Isopropyl acetate | Methanol | 85:15 | 5 |

Results of the six reactions are summarized in Table 21.

TABLE 21

| Reaction No. | Cake weight (mg) | Cake purity (%) | Filtrate purity (%) | Filtration time approx. (min) | Filter cake appearance | Slurry mobility | Drainage |
|---|---|---|---|---|---|---|---|
| 017-1 | 868 | 96.26 | 84.49 | 35 | W, P | 4 | 3 |
| 017-2 | 928 | 96.42 | 81.55 | 35 | W, P | 4 | 3 |
| 017-3 | 880 | 96.36 | 85.09 | 35 | W, P | 4 | 3 |
| 017-4 | 957 | 95.70 | 85.79 | 30 | W, P | 4 | 3 |
| 017-5 | 945 | 95.67 | 83.93 | 30 | W, P | 4 | 3 |
| 017-6 | 976 | 95.92 | 83.05 | 35 | W, P | 4 | 3 |

Filtration time: time for cake to reach semi dry state, not wet

Filter cake appearance: appearance of cake after drying, w = white, y = yellow (colour of cake), H = hard, P = powdery Slurry mobility: 1 = thin, very mobile, 2 = medium thick, mobile, 3 = thick but transfer mostly prior to rinsing, 4 = thick not easily transferable, 5 = very thick, no flow without fresh diluent The final ratio of lysine to 15-(S)-HETrE was determined by NMR as shown in Table 22.

TABLE 22

| Reaction No. | lysine peak | peak at 5.6 ppm | difference | peak at 6 ppm | difference |
|---|---|---|---|---|---|
| 017-1 | 1 | 0.9469 | 0.009916667 | 0.9338 | 0.009116667 |
| 017-2 | 1 | 0.9326 | −0.004383333 | 0.9216 | −0.003083333 |
| 017-3 | 1 | 0.9266 | −0.010383333 | 0.9093 | −0.015383333 |
| 017-4 | 1 | 0.9482 | 0.011216667 | 0.9366 | 0.011916667 |
| 017-5 | 1 | 0.9407 | 0.003716667 | 0.9245 | −0.000183333 |
| 017-6 | 1 | 0.9269 | −0.010083333 | 0.9223 | −0.002383333 |
| average = | | 0.936983333 | | 0.924683333 | |

Impurity data for the six reactions are shown in Table 23.

TABLE 23

Impurity data.

| | RRT | retention time | peak area (%) | 017-1 (salt) | 017-1 (liquor) | 017-2 (salt) | 017-2 (liquor) | 017-3 (salt) | 017-3 (liquor) |
|---|---|---|---|---|---|---|---|---|---|
| IMP 1 | 0.62 | 4.35 | 0.20 | 0.04 | 0.18 | 0.05 | 0.22 | 0.04 | 0.18 |
| IMP 2 | 0.64 | 4.44 | 0.12 | 0.15 | 21.4 | 0.16 | 2.55 | 0.13 | 2.20 |
| IMP 3 | 0.69 | 4.81 | 0.27 | 0.22 | 2.07 | 0.22 | 2.44 | 0.21 | 2.14 |
| IMP 4 | 0.91 | 6.34 | 1.30 | 1.07 | 2.78 | 1.08 | 2.89 | 1.01 | 2.86 |
| HETrE | 1 | 6.97 | 95.67 | 96.29 | 84.49 | 96.42 | 81.55 | 96.36 | 85.09 |
| IMP 5 | 1.03 | 7.2 | 0 | 0.09 | 0.84 | 0.07 | 1.07 | 0.07 | 0.78 |
| IMP 6 | 1.1 | 7.7 | 1.44 | 1.49 | 1.65 | 1.62 | 1.63 | 1.62 | 1.65 |
| IMP 7 | 1.75 | 12.25 | 0.55 | 0.21 | 2.95 | 0.17 | 3.51 | 0.17 | 2.32 |

| | RRT | retention time | peak area (%) | 017-4 (salt) | 017-4 (liquor) | 017-5 (salt) | 017-5 (liquor) | 017-6 (salt) | 017-6 (liquor) |
|---|---|---|---|---|---|---|---|---|---|
| IMP 1 | 0.62 | 4.35 | 0.20 | 0.06 | 0.28 | 0.06 | 0.37 | 0.06 | 0.34 |
| IMP 2 | 0.64 | 4.44 | 0.125 | 0.10 | 3.52 | 0.31 | 4.12 | 0.20 | 4.17 |
| IMP 3 | 0.69 | 4.81 | 0.27 | 0.24 | 3.39 | 0.30 | 3.95 | 0.30 | 3.98 |
| IMP 4 | 0.91 | 6.34 | 1.30 | 1.34 | 2.92 | 1.11 | 3.21 | 1.03 | 3.18 |
| HETrE | 1 | 6.97 | 95.67 | 95.70 | 85.79 | 95.67 | 83.93 | 95.92 | 83.01 |
| IMP 5 | 1.03 | 7.2 | 0 | 0.08 | 0.77 | 0.10 | 0.95 | 0.07 | 0.93 |
| IMP 6 | 1.1 | 7.7 | 1.44 | 1.62 | 1.71 | 1.76 | 1.56 | 1.57 | 1.58 |
| IMP 7 | 1.75 | 12.25 | 0.55 | 0.23 | 0.2 | 0.06 | 0.03 | 0.17 | 0.04 |

The DGLA content of the 15-(S)-HETrE lysine salt was determined by CAD, as shown in Table 24.

TABLE 24

DGLA content of 15-(S)-HETrE lysine salt.

| Reaction No. | Spiked DGLA (w/w) | Sample conc. (mg/mL) | Peak area | DGLA in salt (determined) (w/w) |
|---|---|---|---|---|
| DGLA | | 0.1625 | 3449760 | |
| 017-1 | 1.25 | 1.51 | 244710 | 0.76 |
| 017-2 | 2.5 | 1.5 | 448768 | 1.41 |
| 017-3 | 5 | 1.47 | 954206 | 3.06 |
| 017-4 | 1.25 | 1.49 | 233803 | 0.74 |
| 017-5 | 2.5 | 1.63 | 523225 | 1.51 |
| 017-6 | 5 | 1.59 | 1003375 | 2.97 |

Example 20. Reslurry Experiments

An experiment was conducted to determine if the ratio of 15-(S)-HETrE to lysine would change after exposure to ethyl acetate. 15-(S)-HETrE lysine salt (100 mg) was suspended in HPLC grade ethyl acetate (1 mL) and stirred vigorously overnight at room temperature. The suspension was then filtered as described in previous examples. The impurity profiles of the starting 15-(S)-HETrE lysine salt ("before slurry") and the slurried, filtered salt ("after reslurry") are shown in Table 25.

TABLE 25

| | RRT | Retention time | Before reslurry | After reslurry |
|---|---|---|---|---|
| IMP 1 | 0.62 | 4.35 | 0.04 | 0.16 |
| IMP 2 | 0.64 | 4.44 | 0.09 | 0.39 |
| IMP 3 | 0.69 | 4.81 | 0.11 | 0.16 |
| IMP 4 | 0.91 | 6.34 | 1.01 | 1.08 |
| HETrE | 1 | 6.97 | 96.66 | 95.69 |
| IMP 5 | 1.03 | 7.2 | 0.15 | 0.07 |
| IMP 6 | 1.1 | 7.7 | 1.39 | 1.47 |
| IMP 7 | 1.75 | 12.25 | 0.26 | 0.11 |

NMR spectroscopy confirmed no change in the ratio of 15-(S)-HETrE-to-lysine ratio.

Example 21. Solvent-Induced Degradation of 15-(S)-HETrE Lysine Salt

An experiment to determine the degradation of 15-(S)-HETrE lysine salt, if any, when contacted with ethyl acetate or methanol. 15-(S)-HETrE lysine salt (100 mg) was dissolved in solvent (1 mL) and stirred overnight. UPLC analysis of the resulting mixtures, compared to the original 15-(S)-HETrE lysine salt, are shown in Table 26.

TABLE 26

| | RRT | Retention time | Peak area (%) | In methanol | In ethyl acetate |
|---|---|---|---|---|---|
| IMP 1 | 0.62 | 4.35 | 0.20 | 0.03 | 0.05 |
| IMP 2 | 0.64 | 4.44 | 0.12 | 0.24 | 0.86 |
| IMP 3 | 0.69 | 4.81 | 0.27 | 0.45 | 0.96 |
| IMP 4 | 0.91 | 6.34 | 1.30 | 1.16 | 1.30 |
| HETrE | 1 | 6.97 | 95.67 | 95.40 | 94.20 |
| IMP 5 | 1.03 | 7.2 | 0 | 0.13 | 0.29 |
| IMP 6 | 1.1 | 7.7 | 1.44 | 1.34 | 1.35 |
| IMP 7 | 1.75 | 12.25 | 0.55 | 0.31 | 0.14 |

Example 22. Seeding Timing

Experiments to determine timing for efficient addition of seed were performed. Two experiments were set up similar to Example 16. 15-(S)-HETrE dissolved in ethyl acetate was added as a percentage of the total ethyl acetate charge (see Table 27), and was added to a stirring suspension of lysine hydrate (399±2 mg) in methanol (1.2 mL) and observed for a period of time.

TABLE 27

| Experiment | 15-(S)-HETrE (% charge) |
|---|---|
| 1 | 10 |
| 2 | 20 |

In each of Experiments 1 and 2, addition of 15-(S)-HETrE solution to lysine suspension created a viscous non-mobile suspension.

Example 23. Preparation of 15-(S)-HETrE Methyl Ester 15-(S)-HETrE methyl ester was prepared by combining 15-(S)-HETrE (100 mg), potassium carbonate (129 mg, 3 equiv.) and methyl iodide (220 mg, 5 equiv.) in DMF (0.5 mL). The mixture was stirred at room temperature for 18 hours. Following a quench with water (5 mL), the organic phase was extracted with MtBE (2×5 mL) and the combined organic phases were washed with brine (5 mL), dried and concentrated.

Example 24. Preparation of 15-(S)-HETrE Lysine Salt

A series of experiments was performed to determine various process parameters.

Reaction 021-A: L-Lysine Suspended in Methanol

L-Lysine mono-hydrate (798±2 mg) was suspended in degassed methanol (3.2 mL) in a nitrogen filled 50 mL 3-neck round bottom flask (RBF). 15-(S)-HETrE (1606±2 mg) was dissolved in degassed ethyl acetate (12.8 mL) and added to the stirring suspension of lysine. Seed (100 mg) was added subsequently and stirred at 250 rpm overnight. The suspension was filtered under nitrogen through a size 3 sinter glass funnel (40 mm diameter) and washed with ethyl acetate (12 mL, 3×4 mL) portions.

Reaction 021-B: L-Lysine Suspended in Ethyl Acetate

L-Lysine mono-hydrate (798±2 mg) was suspended in degassed ethyl acetate (12.8 mL) in a nitrogen filled 50 mL 3-neck RBF. 15-(S)-HETrE (1606±2 mg) was dissolved in degassed methanol (3.2 mL) and added to the stirring suspension of lysine. Seed (100 mg) was added subsequently and stirred at 250 rpm overnight. The suspension was filtered under nitrogen through a size 3 sinter glass funnel (40 mm diameter) and washed with ethyl acetate (12 mL, 3×4 mL) portions.

Reaction 021-C: Addition of Hot 15-(S)-HETrE

An experiment was performed as above, except the 15-(S)-HETrE solution was heated to 45° C. before addition to the lysine suspension.

Reaction 021-D: Addition of 15-(S)-HETrE to Hot Lysine Suspension

An experiment was performed as above, except the lysine suspension was heated to 45° C. for 15 minutes to equilibrate before the solution of 15-(S)-HETrE was added. The seed (100 mg) was then added, and the mixture was stirred for 5 minutes and left cool to room temperature in the oil bath.

Reaction 021-E: Absence of Seed Addition

An experiment identical to Reaction 021-D was performed except the seed was not added.

Reaction 021-F: Additional Temperature Cycling

Reaction 021-E was repeated with an addition temperature cycle as follows: after the salt formation occurred at 45° C., the mixture was cooled to 20° C., then re-heated to 45° C. and held for 2 hours. Final cool-down to 20° C. occurred overnight.

Reaction 021-G: Additional Stir Time

Reaction 021-E was repeated, except the mixture was cooled from 45° C. to 20° C. and stirred for 6 hours before harvesting the 15-(S)-HETrE lysine salt.

Results of Reactions 021-A to 021-G are shown in Table 28.

TABLE 28

| Reaction No. | Ratio | Cake weight (mgs) | Cake purity (%) | Filtration time approx. (mins) | Filter cake appearance | Slurry mobility | Drainage |
|---|---|---|---|---|---|---|---|
| 021-A | 80:20 | 1672 | 95.34 | 15 | W, P | 4 | 3 |
| 021-B | 80:20 | 1587 | 95.24 | 15 | Y, H (W, P when cake was broken) | 4 | 3 |
| 021-C | 80:20 | 1509 | 94.99 | 15 | Y, H (W, P when cake was broken) | 4 | 3 |
| 021-D | 80:20 | 1678 | 95.06 | 10-12 | W, P | 2 (slurry could be poured from RBF) | 2 |
| 021-E | 80:20 | 1627 | 95.21 | 10-12 | Y, H (W, P when cake was broken) | 2 | 2 |
| 021-F | 80:20 | 1498 | 94.20 | 10-12 | Y, H (W, P when cake was broken) | 2 | 2 |
| 021-G | 80:20 | 1680 | 94.94 | 15 | W, P (yellow crust) | 2 | 2 |

The ratio of lysine to 15-(S)-HETrE was determined by NMR, as shown in Table 29.

TABLE 29

| Reaction No. | lysine peak | peak at 5.6 ppm | difference | peak at 6 ppm | difference |
|---|---|---|---|---|---|
| 021-A | 1 | 0.9454 | 0.0157 | 0.9034 | 0.00054 |
| 021-B | 1 | 0.9581 | 0.0284 | 0.9221 | 0.01924 |
| 021-C | 1 | 0.8764 | −0.0533 | 0.8629 | −0.03996 |
| 021-D | 1 | 0.9249 | −0.0048 | 0.9154 | 0.01254 |
| 021-E | 1 | 0.915 | −0.0147 | 0.8928 | −0.01006 |
| 021-F | 1 | 0.92 | −0.0097 | 0.9016 | −0.00126 |
| 021-G | 1 | 0.9681 | 0.9681 | 0.9218 | 0.92180 |
| average = | | 0.9297 | | 0.902857143 | |

The impurity profiles of each reaction is shown in Table 30.

TABLE 30

Impurity profiles.

| | RRT | Retention time | Peak area (%) | 021-A | 021-B | 021-C | 021-D | 021-E | 021-F | 021-G (salt) | 021-G (liquor) |
|---|---|---|---|---|---|---|---|---|---|---|---|
| IMP 1 | 0.62 | 4.35 | 0.12 | 0.17 | 0.22 | 0.24 | 0.19 | 0.17 | 0.27 | ND | 0.74 |
| IMP 2 | 0.64 | 4.44 | 0.51 | 0.08 | 0.12 | 0.10 | 0.08 | 0.18 | 0.20 | 0.24 | 1.38 |
| IMP 3 | 0.66 | 4.64 | 0.89 | 0.33 | 0.44 | 0.40 | 0.38 | 0.44 | 0.55 | 0.52 | 3.57 |
| IMP 4 | 0.69 | 4.81 | 0.13 | 0.18 | 0.22 | 0.23 | 0.21 | 0.18 | 0.28 | 0.26 | 0.57 |
| IMP 5 | 0.72 | 4.99 | 1.29 | 0.19 | 0.24 | 0.2 | 0.19 | 0.31 | 0.44 | 0.46 | 3.94 |
| IMP 6 | 0.85 | 5.92 | 0.16 | 0.08 | 0.08 | 0.13 | 0.09 | 0.08 | 0.12 | 0.08 | 0.57 |
| IMP 7 | 0.91 | 6.34 | 1.17 | 1.06 | 0.75 | 0.95 | 1.08 | 0.98 | 0.96 | 1.01 | 1.91 |
| IMP 8 | 0.98 | 6.84 | 0.29 | 0.09 | 0.29 | 0.16 | 0.11 | 0.14 | 0.14 | 0.89 | 0.51 |
| HETrE | 1 | 6.97 | 91.38 | 95.34 | 95.24 | 94.99 | 95.06 | 95.21 | 94.20 | 94.94 | 69.51 |
| IMP 9 | 1.03 | 7.32 | 0.18 | 0.15 | 0.13 | 0.14 | 0.16 | 0.16 | 0.15 | 0.16 | 0.85 |

TABLE 30-continued

Impurity profiles.

| | RRT | Retention time | Peak area (%) | 021-A | 021-B | 021-C | 021-D | 021-E | 021-F | 021-G (salt) | 021-G (liquor) |
|---|---|---|---|---|---|---|---|---|---|---|---|
| IMP 10 | 1.1 | 7.41 | 0.23 | 1.41 | 1.32 | 1.26 | 1.39 | 1.24 | 1.30 | 1.36 | 1.00 |
| IMP 11 | 1.75 | 12.25 | 0.88 | 0.18 | 0.11 | 0.23 | 0.25 | 0.25 | 0.38 | 0.31 | 6.63 |

The salt prepared in Reaction 021-D (400 mg) was reslurried in ethyl acetate/methanol (80/20, 2 mL) under the following conditions:

021-D-A: stirred for 6 hours at 20° C.
021-D-B: stirred while ramping temperature from 20° C. to 45° C., then stirred for 2 hours at 45° C. before cooling to 20° C. (total stirring time: 6 hours).

NMR and impurity data are shown in Tables 31 and 32, respectively.

TABLE 31

| Reaction | Lysine peak | Peak at 5.6 ppm | Difference | Peak at 6 ppm | Difference |
|---|---|---|---|---|---|
| 021-D-A | 1 | 1.1043 | 0.03065 | 03.9818 | −0.00765 |
| 021-D-B | 1 | 1.043 | −0.03065 | 0.9971 | 0.00765 |
| Average = | | 1.07365 | | 0.98945 | |

TABLE 32

| | RRT | Retention time | Peak area (%) 021-D | 021-D-A | 021-D-B |
|---|---|---|---|---|---|
| IMP 1 | 0.62 | 4.35 | 0.19 | 0.22 | 0.22 |
| IMP 2 | 0.64 | 4.44 | 0.08 | 0.05 | 0.05 |
| IMP 3 | 0.66 | 4.64 | 0.38 | 0.36 | 0.35 |
| IMP 4 | 0.69 | 4.81 | 0.21 | 0.23 | 0.21 |
| IMP 5 | 0.72 | 4.99 | 0.19 | 0.11 | 0.10 |
| IMP 6 | 0.85 | 5.92 | 0.09 | 0.08 | 0.08 |
| IMP 7 | 0.91 | 6.34 | 1.08 | 1.09 | 1.04 |
| IMP 8 | 0.98 | 6.84 | 0.11 | 0.09 | 0.09 |
| HETrE | 1 | 6.97 | 95.06 | 95.50 | 95.64 |
| IMP 9 | 1.03 | 7.32 | 0.16 | 0.16 | 0.16 |
| IMP 10 | 1.1 | 7.41 | 1.39 | 1.42 | 1.37 |
| IMP 11 | 1.75 | 12.25 | 0.25 | 0.16 | 0.18 |

Reactions 021-D and 021-E were repeated, with filtration of the final salt performed using a pressurized filter. Yield and purity of the salt, NMR data, and impurity profiles are shown in Tables 33-35, respectively.

TABLE 33

| experiment | Cake weight (mgs) | Cake purity (%) | Filtration time approx. (mins) | Filter cake appearance | Slurry mobility | Drainage |
|---|---|---|---|---|---|---|
| 029-A | 1795 | 94.10 | 15 | Y, H (white powder when ground) | 2 | 2 |
| 029-B | 1933 | 93.83 | 15 | Y, H (white powder when ground) | 2 | 2 |

TABLE 34

| experiment | lysine peak | peak at 5.6 ppm | difference | peak at 6 ppm | difference |
|---|---|---|---|---|---|
| 029-A | 1 | 1.0165 | 0.00035 | 0.9869 | −0.00070 |
| 029-B | 1 | 1.0158 | −0.00035 | 0.9883 | 0.00070 |
| average = | | 1.01615 | | 0.9876 | |

TABLE 35

| | RRT | Retention time | Peak area (%) | 029-A (salt) | 029-A (liquor) | 029-B (salt) | 029-B (liquor) |
|---|---|---|---|---|---|---|---|
| IMP 1 | 0.62 | 4.35 | 0.12 | 0.23 | 0.93 | 0.27 | 0.93 |
| IMP 2 | 0.64 | 4.44 | 0.51 | 0.32 | 1.37 | 0.29 | 1.37 |
| IMP 3 | 0.66 | 4.64 | 0.89 | 0.67 | 3.67 | 0.74 | 3.73 |
| IMP 4 | 0.69 | 4.81 | 0.13 | 0.24 | 0.99 | 0.29 | 0.99 |
| IMP 5 | 0.72 | 4.99 | 1.29 | 0.77 | 3.97 | 0.33 | 3.78 |
| IMP 6 | 0.85 | 5.92 | 0.16 | 0.02 | 1.01 | 0.02 | 0.96 |
| IMP 7 | 0.91 | 6.34 | 1.17 | 1.05 | 1.93 | 1.06 | 1.95 |
| IMP 8 | 0.98 | 6.84 | 0.29 | 0.26 | 0.65 | 0.21 | 0.65 |
| HETrE | 1 | 6.97 | 91.38 | 94.10 | 65.65 | 93.83 | 66.17 |
| IMP 9 | 1.03 | 7.32 | 0.18 | 0.19 | 0.13 | 0.18 | 0.13 |
| IMP 10 | 1.1 | 7.41 | 1.41 | 1.42 | 1.26 | 1.34 | 1.36 |
| IMP 11 | 1.75 | 12.25 | 0.88 | 0.36 | 6.99 | 0.01 | 6.92 |

Example 25. Wash Solvents

An experiment was performed to determine the effects of different wash solvents (see Table 36) on the yield and purity of the 15-(S)-HETrE lysine salt.

TABLE 36

| experiment | Wash solvent | Cake weight (mgs) | Cake purity (%) | Filtration time approx. (mins) | Filter cake appearance | Slurry mobility | Drainage |
|---|---|---|---|---|---|---|---|
| 023-A | Ethyl acetate:methanol (80/20) | 777 | 94.32 | 10 | Y, H (white powder when ground) | 2 | 2 |

TABLE 36-continued

| experiment | Wash solvent | Cake weight (mgs) | Cake purity (%) | Filtration time approx. (mins) | Filter cake appearance | Slurry mobility | Drainage |
|---|---|---|---|---|---|---|---|
| 023-B | Ethyl acetate | 826 | 94.10 | 10 | Y, H (white powder when ground) | 2 | 2 |
| 023-C | methanol | 760 | 94.34 | 10 | Y, H (white powder when ground) | 2 | 2 |

NMR and impurity data are shown in Tables 37 and 38, respectively.

TABLE 37

| experiment | lysine peak | peak at 5.6 ppm | difference | peak at 6 ppm | difference |
|---|---|---|---|---|---|
| 023-A | 1 | 1.0124 | 0.000933333 | 0.9814 | −0.00707 |
| 023-B | 1 | 1.0104 | −0.001066667 | 0.9965 | 0.00803 |
| 023-C | 1 | 1.0116 | 0.000133333 | 0.9875 | −0.00097 |
| average = | | 1.011466667 | | 0.988466667 | |

TABLE 38

| | RRT | Retention time | Peak area (%) | 023-A | 023-B | 023-C |
|---|---|---|---|---|---|---|
| IMP 1 | 0.62 | 4.35 | 0.12 | 0.01 | 0.01 | 0.01 |
| IMP 2 | 0.64 | 4.44 | 0.51 | 0.38 | 0.38 | 0.38 |
| IMP 3 | 0.66 | 4.64 | 0.89 | 0.66 | 0.65 | 0.62 |
| IMP 4 | 0.69 | 4.81 | 0.13 | 0.40 | 0.40 | 0.40 |
| IMP 5 | 0.72 | 4.99 | 1.29 | 0.48 | 0.48 | 0.51 |
| IMP 6 | 0.85 | 5.92 | 0.16 | 0.03 | 0.02 | 0.04 |
| IMP 7 | 0.91 | 6.34 | 1.17 | 1.00 | 1.07 | 1.18 |
| IMP 8 | 0.98 | 6.84 | 0.29 | 0.23 | 0.21 | 0.21 |
| HETrE | 1 | 6.97 | 91.38 | 94.32 | 94.10 | 94.34 |
| IMP 9 | 1.03 | 7.32 | 0.18 | 0.18 | 0.18 | 0.19 |
| IMP 10 | 1.1 | 7.41 | 1.41 | 1.4 | 1.40 | 1.49 |
| IMP 11 | 1.75 | 12.25 | 0.88 | 0.33 | 0.47 | 0.52 |

Example 26. Isopropyl Acetate

An experiment was conducted to examine whether any degradation would be observed upon exposure of 15-(S)-HETrE to isopropyl acetate. 15-(S)-HETrE (100 mg) was dissolved in isopropyl acetate (1 mL) and stirred overnight. This was sampled directly for UPLC analysis (Table 39).

TABLE 39

| | RRT | Retention time | Peak area (%) | Example 26 |
|---|---|---|---|---|
| IMP 1 | 0.62 | 4.35 | 0.12 | 0.22 |
| IMP 2 | 0.64 | 4.44 | 0.51 | 1.48 |
| IMP 3 | 0.66 | 4.64 | 0.89 | 1.47 |
| IMP 4 | 0.69 | 4.81 | 0.13 | 0.19 |
| IMP 5 | 0.72 | 4.99 | 1.29 | 3.02 |
| IMP 6 | 0.85 | 5.92 | 0.16 | 0.43 |
| IMP 7 | 0.91 | 6.34 | 1.17 | 1.56 |
| IMP 8 | 0.98 | 6.84 | 0.29 | 0.62 |
| HETrE | 1 | 6.97 | 91.38 | 85.56 |
| IMP 9 | 1.03 | 7.32 | 0.18 | 0.28 |
| IMP 10 | 1.1 | 7.41 | 1.41 | 1.79 |
| IMP 11 | 1.75 | 12.25 | 0.88 | 1.14 |

Example 27. Lysine Salt Formations of Semi-Purified and Crude 15-(S)-HETrE

An experiment to determine the impact of salt formation on the purity of the 15-(S)-HETrE starting material was performed. The amount of lysine used was adjusted based on the purity of the 15-(S)-HETrE as determined by UPLC analysis. 15-(S)-HETrE (10 g) was loaded onto a pre-wet column and eluted with cyclohexane:MtBE (50:50) (350 mL) until the 15-(S)-HETrE spot was no longer evident by TLC. The relevant fractions were concentrated. Yield and purity data are shown in Table 40; NMR and impurity profiles are shown in Tables 41-42, respectively.

TABLE 40

| experiment | 15-(S)-HETrE | Cake weight (mgs) | Cake purity (%) | Filtration time approx. (mins) | Filter cake appearance | Slurry mobility | Drainage |
|---|---|---|---|---|---|---|---|
| 027-A | Crude (91.6% purity) | 1896 | 94.75 | 7 | Y, H (white powder when ground) | 2 | 1 |
| 027-B | Semi-purified (92.3% purity) | 1820 | 95.37 | 15 | Y, H (white powder when ground) | 2 | 2 |

TABLE 41

| experiment | lysine peak | peak at 5.6 ppm | difference | peak at 6 ppm | difference |
|---|---|---|---|---|---|
| 027-A | 1 | 1.0014 | −0.0082 | 0.994 | −0.01140 |
| 027-B | 1 | 1.0178 | 0.0082 | 1.0168 | 0.01140 |
| average = | | 1.0096 | | 1.0054 | |

TABLE 42

| | RRT | Retention time | Peak area (Crude), % | 027-A (salt) | 027-A (liquor) | Peak area (semi-pure), % | 027-B (salt) | 027-B (liquor) |
|---|---|---|---|---|---|---|---|---|
| IMP 1 | 0.62 | 4.35 | 0.05 | 0.07 | 0.52 | 0.09 | 0.03 | 0.26 |
| IMP 2 | 0.64 | 4.44 | 0.05 | 0.05 | 0.34 | 0.10 | 0.05 | 0.2 |
| IMP 3 | 0.66 | 4.64 | 0.55 | 0.57 | 15.68 | 0.63 | 0.24 | 18.84 |
| IMP 4 | 0.69 | 4.81 | 0.13 | 0.17 | 0.63 | 0.14 | 0.12 | 0.62 |
| IMP 5 | 0.72 | 4.99 | 0.15 | 0.15 | 0.84 | 0.1 | 0.27 | 0.14 |
| IMP 6 | 0.85 | 5.92 | 0.84 | 0.14 | 17.40 | 0.08 | 0.09 | 21.78 |
| IMP 7 | 0.91 | 6.34 | 1.18 | 1.09 | 0.95 | 1.09 | 1.14 | 0.56 |
| IMP 8 | 0.98 | 6.84 | 0.05 | 0.01 | 0.98 | 0.01 | 0.01 | 0.02 |
| HETrE | 1 | 6.97 | 91.6 | 94.75 | 28.09 | 92.3 | 95.37 | 20.37 |
| IMP 9 | 1.03 | 7.32 | 0.31 | 0.1 | 5.50 | 0.36 | 0.19 | 6.45 |
| IMP 10 | 1.1 | 7.41 | 1.48 | 1.38 | 7.21 | 1.46 | 1.45 | 8.58 |
| IMP 11 | 1.75 | 12.25 | 0.35 | 0.24 | 4.88 | 0.56 | 0.43 | 5.68 |

Example 28. Salt Formation at 0° C.

L-Lysine mono-hydrate (820 mg) was suspended in ethyl acetate (degassed, 3.2 mL) in a 25-mL RBF and heated to 45° C. 15-(S)-HETrE (1606±2 mg) was dissolved in methanol (12.8 mL) and added to the stirring suspension of lysine. The suspension was allowed to cool to room temperature in the oil bath and the flask was then transferred to a water bath and cooled over a period of time to 0° C., after which it was stirred for a further 2 hours. The salt was collected by pressure filtration and washed with the mother liquor. Yield and filtration performance data are shown in Table 43.

TABLE 43

| Cake weight (mgs) | Cake purity (%) | Filtration time approx. (mins) | Filter cake appearance | Slurry mobility | Drainage |
|---|---|---|---|---|---|
| 2009 | Not specified | 7-10 | W, P (hard and pale yellow when dried further) | 2 | 1 |

Example 29. Salt Formation in Methanol or Ethanol

L-Lysine mono-hydrate (399±2 mg) was suspended in 1.6 mL of either methanol (Reaction 031-A) or ethanol (Reaction 031-B) in a 20 mL snap cap vial, 15-(S)-HETrE (803±2 mg) was dissolved in the same alcohol (6.4 mL) and added to the stirring suspension of lysine, and stirred at 250 rpm overnight. No salt formation was observed in the methanol solvent system. Seeding with salt from a previous experiment did not induce salt formation. The lysine salt formed in the ethanol system. Yield and purity data are shown in Table 44; NMR and impurity profiles are shown in Tables 45-46, respectively.

TABLE 44

| experiment | Solvent | Cake weight (mgs) | Cake purity (%) | Filtration time approx. (mins) | Filter cake appearance | Slurry mobility | Drainage |
|---|---|---|---|---|---|---|---|
| 031-B | ethanol | 833 | 93.13 | 10 | Y, H (white powder when ground) | 2 | 2 |

TABLE 45

| experiment | lysine peak | peak at 5.6 ppm | difference | peak at 6 ppm | difference |
|---|---|---|---|---|---|
| 031-B | 1 | 1.03 | — | 1.002 | — |

TABLE 46

| | RRT | Retention time | Peak area (%) | 031-B (salt) | 031-B (liquor) |
|---|---|---|---|---|---|
| IMP 1 | 0.62 | 4.35 | 0.12 | 0.31 | 1.88 |
| IMP 2 | 0.64 | 4.44 | 0.51 | 0.60 | 1.62 |
| IMP 3 | 0.66 | 4.64 | 0.89 | 0.62 | 4.32 |
| IMP 4 | 0.69 | 4.81 | 0.13 | 0.34 | 1.73 |
| IMP 5 | 0.72 | 4.99 | 1.29 | 0.49 | 3.39 |
| IMP 6 | 0.85 | 5.92 | 0.16 | 0.01 | 0.56 |
| IMP 7 | 0.91 | 6.34 | 1.17 | 1.01 | 1.76 |

TABLE 46-continued

| | RRT | Retention time | Peak area (%) | 031-B (salt) | 031-B (liquor) |
|---|---|---|---|---|---|
| IMP 8 | 0.98 | 6.84 | 0.29 | 0.02 | 0.27 |
| HETrE | 1 | 6.97 | 91.38 | 93.13 | 71.78 |
| IMP 9 | 1.03 | 7.32 | 0.18 | 0.15 | 0.59 |
| IMP 10 | 1.1 | 7.41 | 1.41 | 1.39 | 1.19 |
| IMP 11 | 1.75 | 12.25 | 0.88 | 0.60 | 3.6 |

Example 30. Impurity Profiles From Various 15-(S)-HETrE Starting Materials 15-(S)-HETrE lysine salts were prepared according to a method consistent with Example 16 from 15-(S)-HETrE starting materials (abbreviated "FA" below) having various purity levels. The impurity profiles of the resulting lysine salts (abbreviated "HLS" below) are shown in Table 47 as determined by UPLC.

TABLE 47

Impurity Profiles.

| | Retention time | Purified FA | HLS-1 | Semi-purified FA | HLS-2 | Crude FA | HLS-3 | Notes |
|---|---|---|---|---|---|---|---|---|
| IMP 1 | 4.35 | 0.01 | 0.04 | 0.01 | 0.03 | 0.05 | 0.07 | |
| IMP 2 | 4.44 | 0.10 | 0.06 | 0.09 | 0.06 | 0.06 | 0.05 | |
| IMP 3 | 4.64 | 0.16 | 0.09 | 0.10 | 0.11 | 0.62 | 0.56 | |
| IMP 4 | 4.81 | 0.02 | 0.04 | 0.63 | 0.24 | 0.78 | 0.18 | |
| IMP 5 | 4.89 | 0.01 | 0.03 | 0.01 | 0.02 | 0.14 | 0.17 | |
| IMP 6 | 4.99 | 0.29 | 0.11 | 0.13 | 0.07 | 0.16 | 0.11 | |
| IMP 7 | 5.44 | — | — | 0.02 | 0.04 | 0.06 | 0.01 | (1) |
| IMP 8 | 5.53 | — | — | 0.06 | 0.03 | 0.07 | 0.05 | (1) |
| IMP 9 | 5.92 | 0.14 | 0.02 | 0.79 | 0.27 | 0.84 | 0.14 | (2) |
| IMP 10 | 6.34 | 0.03 | 0.03 | 0.03 | 0.03 | 0.04 | 0.04 | |
| IMP 11 | 6.46 | 1.3 | 1.04 | 1.14 | 1.13 | 1.22 | 1.09 | |
| HETrE | 6.97 | 95.37 | 96.69 | 92.28 | 94.27 | 91.63 | 94.61 | |
| IMP 12 | 7.32 | 0.10 | 0.14 | 0.17 | 0.19 | 0.20 | 0.09 | |
| IMP 13 | 7.41 | 0.10 | 0.05 | 0.37 | 0.15 | 0.42 | 0.10 | (2) |
| IMP 14 | 7.78 | 1.43 | 1.42 | 1.48 | 1.44 | 1.49 | 1.38 | |
| IMP 15 | 7.98 | — | — | 0.34 | 0.02 | 0.55 | 0.02 | (1) |
| IMP 16 | 8.311 | — | — | 0.04 | — | 0.04 | 0.04 | (1) |
| IMP 17 | 8.57 | — | — | 0.1 | 0.08 | 0.10 | 0.07 | (1) |
| IMP 18 | 9.57 | — | — | 0.07 | 0.07 | 0.06 | 0.04 | (1) |
| IMP 19 | 9.67 | — | — | 0.09 | 0.07 | 0.09 | 0.09 | (1) |
| IMP 20 | 9.77 | — | — | 0.35 | 0.29 | 0.35 | 0.16 | (1) |
| IMP 21 | 9.93 | — | — | 0.09 | 0.06 | 0.09 | 0.01 | (1) |
| IMP 22 | 10.31 | — | — | 0.24 | 0.17 | 0.24 | 0.19 | (1) |
| IMP 23 | 12.11 | 0.56 | 0.23 | 0.56 | 0.43 | 0.34 | 0.24 | |

Table 47 Notes:
(1) Impurity that is purged during column chromatography.
(2) Impurity that decreased in concentration upon salt formation.

FURTHER EXAMPLES

Further Example 1

A salt of a 15-lipoxygenase product.

Further Example 2

The salt of Further Example 1, wherein the salt is a pharmaceutically acceptable salt.

Further Example 3

The salt of Further Example 1 or Further Example 2, wherein the salt comprises a lysine salt of the 15-lipoxygenase product.

Further Example 4

The salt of any one of Further Examples 1-3, wherein the salt comprises a sodium salt of the 15-lipoxygenase product.

Further Example 5

The salt of any one of Further Examples 1-4, wherein the salt comprises an ornithine salt of the 15-lipoxygenase product.

Further Example 6

The salt of any one of Further Examples 1-5, wherein the salt comprises a piperazine salt of the 15-lipoxygenase product.

Further Example 7

The salt of any one of Further Examples 1-6, wherein the salt comprises a meglumine salt of the 15-lipoxygenase product.

Further Example 8

The salt of any one of Further Examples 1-7 further comprising the 15-lipoxygenase product in free acid form.

Further Example 9

The salt of any one of Further Examples 1-8, wherein the salt is selected from the group consisting of: sodium, lysine, ornithine, piperazine, meglumine, and combinations thereof.

Further Example 10

The salt of any one of Further Examples 1-9, wherein the salt is sodium.

Further Example 11

The salt of any one of Further Examples 1-9, wherein the salt is lysine.

Further Example 12

The salt of any one of Further Examples 1-9, wherein the salt is ornithine.

Further Example 13

The salt of any one of Further Examples 1-9, wherein the salt is piperazine.

Further Example 14

The salt of any one of Further Examples 1-9, wherein the salt is meglumine.

Further Example 15

The salt of any one of Further Examples 1-14, wherein the 15-lipoxygenase product is selected from the group consisting of: 13-HODE, 15-HETrE, 15-OHEPA, 15-HETE, and combinations thereof.

Further Example 16

The salt of any one of Further Examples 1-15, wherein the 15-lipoxygenase product is 13-HODE.

Further Example 17

The salt of any one of Further Examples 1-15, wherein the 15-lipoxygenase product is 15-HETrE.

Further Example 18

The salt of any one of Further Examples 1-15, wherein the 15-lipoxygenase product is 15-OHEPA.

Further Example 19

The salt of any one of Further Examples 1-15, wherein the 15-lipoxygenase product is 15-HETE.

Further Example 20

13-Hydroperoxyoctadeca-9Z,11E-dienoic acid sodium salt.

Further Example 21

13-Hydroperoxyoctadeca-9Z,11E-dienoic acid lysine salt.

Further Example 22

13-Hydroperoxyoctadeca-9Z,11E-dienoic acid ornithine salt.

Further Example 23

13-Hydroperoxyoctadeca-9Z,11E-dienoic acid piperazine salt.

Further Example 24

13-Hydroperoxyoctadeca-9Z,11E-dienoic acid meglumine salt.

Further Example 25

15-Hydroperoxy-eicosa-8(Z),11(Z),13(E)-trienoic acid sodium salt.

Further Example 26

15-Hydroperoxy-eicosa-8(Z),11(Z),13(E)-trienoic acid lysine salt.

Further Example 27

15-Hydroperoxy-eicosa-8(Z),11(Z),13(E)-trienoic acid ornithine salt.

Further Example 28

15-Hydroperoxy-eicosa-8(Z),11(Z),13(E)-trienoic acid piperazine salt.

Further Example 29

15-Hydroperoxy-eicosa-8(Z),11(Z),13(E)-trienoic acid meglumine salt.

Further Example 30

15-Hydroperoxy-eicosa-5(Z),8(Z),11(Z),13(E),17(Z)-pentaenoic acid sodium salt.

Further Example 31

15-Hydroperoxy-eicosa-5(Z),8(Z),11(Z),13(E),17(Z)-pentaenoic acid lysine salt.

Further Example 32

15-Hydroperoxy-eicosa-5(Z),8(Z),11(Z),13(E),17(Z)-pentaenoic acid ornithine salt.

Further Example 33

15-Hydroperoxy-eicosa-5(Z),8(Z),11(Z),13(E),17(Z)-pentaenoic acid piperazine salt.

Further Example 34

15-Hydroperoxy-eicosa-5(Z),8(Z),11(Z),13(E),17(Z)-pentaenoic acid meglumine salt.

Further Example 35

15-Hydroperoxy-5,8,11,13-eicosatetraenoic acid sodium salt.

Further Example 36

15-Hydroperoxy-5,8,11,13-eicosatetraenoic acid lysine salt.

Further Example 37

15-Hydroperoxy-5,8,11,13-eicosatetraenoic acid ornithine salt.

Further Example 38

15-Hydroperoxy-5,8,11,13-eicosatetraenoic acid piperazine salt.

Further Example 39

15-Hydroperoxy-5,8,11,13-eicosatetraenoic acid meglumine salt.

Further Example 40

13-Hydroperoxyoctadeca-9Z,11E-dienoic acid sodium salt.

Further Example 41

13-Hydroxyoctadeca-9Z,11E-dienoic acid lysine salt.

Further Example 42

13-Hydroxyoctadeca-9Z,11E-dienoic acid ornithine salt.

Further Example 43

13-Hydroxyoctadeca-9Z,11E-dienoic acid piperazine salt.

Further Example 44

13-Hydroxyoctadeca-9Z,11E-dienoic acid meglumine salt.

Further Example 45

15-Hydroxy-eicosa-8(Z),11(Z),13(E)-trienoic acid sodium salt.

Further Example 46

15-Hydroxy-eicosa-8(Z),11(Z),13(E)-trienoic acid lysine salt.

Further Example 47

15-Hydroxy-eicosa-8(Z),11(Z),13(E)-trienoic acid ornithine salt.

Further Example 48

15-Hydroxy-eicosa-8(Z),11(Z),13(E)-trienoic acid piperazine salt.

Further Example 49

15-Hydroxy-eicosa-8(Z),11(Z),13(E)-trienoic acid meglumine salt.

Further Example 50

15-Hydroxy-eicosa-5(Z),8(Z),11(Z),13(E),17(Z)-pentaenoic acid sodium salt.

Further Example 51

15-Hydroxy-eicosa-5(Z),8(Z),11(Z),13(E),17(Z)-pentaenoic acid lysine salt.

Further Example 52

15-Hydroxy-eicosa-5(Z),8(Z),11(Z),13(E),17(Z)-pentaenoic acid ornithine salt.

Further Example 53

15-Hydroxy-eicosa-5(Z),8(Z),11(Z),13(E),17(Z)-pentaenoic acid piperazine salt.

Further Example 54

15-Hydroxy-eicosa-5(Z),8(Z),11(Z),13(E),17(Z)-pentaenoic acid meglumine salt.

Further Example 55

15-Hydroxy-5,8,11,13-eicosatetraenoic acid sodium salt.

Further Example 56

15-Hydroxy-5,8,11,13-eicosatetraenoic acid lysine salt.

Further Example 57

15-Hydroxy-5,8,11,13-eicosatetraenoic acid ornithine salt.

Further Example 58

15-Hydroxy-5,8,11,13-eicosatetraenoic acid piperazine salt.

Further Example 59

15-Hydroxy-5,8,11,13-eicosatetraenoic acid meglumine salt.

Further Example 60

A composition comprising the salt of any one of Further Examples 1-59.

Further Example 61

A pharmaceutical composition comprising a salt form of a 15-lipoxygenase product.

Further Example 62

The pharmaceutical composition of Further Example 61, wherein the salt form of the 15-lipoxygenase product comprises the salt of any one of Further Examples 1-59.

Further Example 63

The pharmaceutical composition of Further Example 61 or Further Example 62 further comprising an excipient.

Further Example 64

The pharmaceutical composition of any one of Further Examples 61-63, wherein after storage for at least about 4 weeks, the pharmaceutical composition comprises at least about 98%, at least about 99%, or about 100% of an initial amount of the salt form of the 15-lipoxygenase product.

Further Example 65

The pharmaceutical composition of any one of Further Examples 61-64, wherein after storage for at least about 10 weeks, the pharmaceutical composition comprises at least about 90%, at least about 91%, at least about 92%, at least about 93%, at least about 94%, at least about 95%, at least about 96%, at least about 97%, at least about 98%, at least about 99%, or about 100% of an initial amount of the salt form of the 15-lipoxygenase product.

Further Example 66

The pharmaceutical composition of any one of Further Examples 61-65, wherein after storage for at least about 24 weeks, the pharmaceutical composition comprises at least about 86%, at least about 87%, at least about 88%, at least about 89%, at least about 90%, at least about 91%, at least about 92%, at least about 93%, at least about 94%, at least about 95%, at least about 96%, at least about 97%, at least about 98%, at least about 99%, or about 100% of an initial amount of the salt form of the 15-lipoxygenase product.

Further Example 67

The pharmaceutical composition of any one of Further Examples 64-66, wherein the pharmaceutical composition is stored at 2-8° C., at 20° C., at 25° C., or at 40° C.

Further Example 68

The pharmaceutical composition of any one of Further Examples 64-67, wherein the pharmaceutical composition is stored at 60% RH or at 75% RH.

Further Example 69

The pharmaceutical composition of any one of Further Examples 61-68, wherein the pharmaceutical composition comprises a therapeutically effective amount of the salt of the 15-lipoxygenase product.

Further Example 70

The pharmaceutical composition of Further Example 69, wherein the therapeutically effective amount of the salt form of the 15-lipoxygenase product is about 0.1 wt. % to about 20 wt. %.

Further Example 71

The pharmaceutical composition of any one of Further Examples 61-70, wherein the pharmaceutical composition is in a form suitable for topical administration.

Further Example 72

The pharmaceutical composition of any one of Further Examples 61-71, wherein the salt form of the 15-lipoxygenase product is the sole significant active ingredient or the sole active ingredient in the pharmaceutical composition.

Further Example 73

The pharmaceutical composition of any one of Further Examples 61-71 further comprising an additional active agent.

Further Example 74

The pharmaceutical composition of Further Example 73, wherein the salt form of the 15-lipoxygenase product and the additional active agent are co-formulated as a single dosage unit.

Further Example 75

The pharmaceutical composition of Further Example 73, wherein the salt form of the 15-lipoxygenase product and the additional active agent are formulated as at least two dosage units for coordinated, combined or concomitant administration.

Further Example 76

A method of treating a disease or disorder in subject in need thereof, the method comprising administering to the subject the pharmaceutical composition of any one of Further Examples 61-75.

Further Example 77

The method of Further Example 76, wherein the disease or disorder is selected from the group consisting of: acne, erythema, infection, fatty liver, neuropathy, and skin inflammation.

Further Example 78

The method of Further Example 76 or Further Example 77, wherein the pharmaceutical composition is administered to the subject in an amount sufficient to provide a therapeutically effective amount of the salt form of the 15-lipoxygenase product.

Further Example 79

The method of Further Example 78, wherein the therapeutically effective amount is about 0.001 mg/kg/day to about 100 mg/kg/day.

What is claimed is:
1. A method of treating a skin inflammation, acne or erythema in a subject in need thereof, the method comprising administering to the subject a pharmaceutical composition comprising a lysine salt form of 15-hydroxy-8(Z),11(Z),13(E)-eicosatrienoic acid (15-HETrE).
2. The method of claim 1, wherein the pharmaceutical composition further comprises an excipient.
3. The method of claim 1, wherein the pharmaceutical composition is administered topically.

* * * * *